US007001761B2

(12) United States Patent
Xiao

(10) Patent No.: US 7,001,761 B2
(45) Date of Patent: Feb. 21, 2006

(54) DNA SEQUENCES COMPRISING DYSTROPHIN MINIGENES AND METHODS OF USE THEREOF

(75) Inventor: Xiao Xiao, Wexford, PA (US)

(73) Assignee: Asklêpios Biopharmaceutical, Inc., Chapel Hill, NC (US)

( * ) Notice: Subject to any disclaimer, the term of this patent is extended or adjusted under 35 U.S.C. 154(b) by 495 days.

(21) Appl. No.: 09/845,416

(22) Filed: Apr. 30, 2001

(65) Prior Publication Data

US 2003/0171312 A1 Sep. 11, 2003

Related U.S. Application Data

(60) Provisional application No. 60/200,777, filed on Apr. 28, 2000.

(51) Int. Cl.
*C12N 15/00* (2006.01)
*C12N 15/09* (2006.01)
*C12N 15/63* (2006.01)
*C12N 15/70* (2006.01)
*C12N 15/74* (2006.01)

(52) U.S. Cl. .................. 435/320.1; 536/23.1; 536/23.5

(58) Field of Classification Search .............. 435/320.1, 435/455; 536/23.1, 23.5; 514/74; 424/99.2
See application file for complete search history.

(56) References Cited

U.S. PATENT DOCUMENTS

| 4,868,116 A | 9/1989 | Morgan et al. |
|---|---|---|
| 5,173,414 A | 12/1992 | Lebkowski et al. |
| 5,399,346 A | 3/1995 | Anderson et al. |
| 5,449,614 A | 9/1995 | Danos et al. |
| 5,661,033 A | 8/1997 | Ho et al. |
| 5,985,846 A | 11/1999 | Kochanek et al. |
| 6,083,750 A | 7/2000 | Chamberlain et al. |
| 6,207,455 B1 | 3/2001 | Chang |
| 2003/0216332 A1 * | 11/2003 | Chamberlain et al. ........ 514/44 |

FOREIGN PATENT DOCUMENTS

| JP | 1999318467 A | * 11/1999 |
|---|---|---|
| WO | WO 89/06286 | 7/1989 |

OTHER PUBLICATIONS

Provisional Application 60/238,848.*
T–L Chiu et al., Folding and Design," Optimizing energy potentials for success in protein tertiary structure prediction," May 1998, 3:223–228.*
JT Ngo et al., The Protein Folding Problem and Tertiary Structure Prediction, "Computational Complexity, Protein Structure Prediction, and the Levinthal Paradox," 1994, pp. 433 and 492–495.*

Roberts, et.al., Determination of the Exon Structure of the Distal Portion of the Dystrophin Gene by Vectorette PCR. Genomics. 1992, vol. 13, pp. 942–950, especially 947 and 949.

Rosenthal, et.al., Two Human cDNA Molecules Coding for the Duchenne Muscular Dystrophy (DMD) Locus are Highly Homologous. Nucleic Acid Research. 1989, vol. 17, No. 13, p. 5391.

Koenig, et.al., The Complete Sequence of Dystrophin Predicts a Rod–Shaped Cytoskeletal Protein. Cell. Apr. 1998, vol. 53, pp. 219–228, especially pp. 220–221 and 223.

Anderson, W.F. Human Gene Therapy. Apr. 1998, vol. 392, pp. 25–30.

Wang, et.al. Adeno–Associated Virus Vector Carrying Human Minidystrophin Genes Effectively Ameliorates Muscular Dystrophy in mdx Mouse Model. Dec. 2000, vol. 97, No. 25, pp. 13714–13719.

Kunkel, et.al. Analysis of Deletions in DNA From Patients with Becker and Duchenne Muscular Dystrophy. Nature Jul. 1986, vol. 322, No. 3, pp. 73–77.

Watkins, et.al. Immunoelectron Microscopic Localization of Dystrophin in Myofibres. Nature Jun. 1988, vol. 333, No. 30, pp. 863–866.

Koenig, et.al. Detailed Analysis of the Repeat Domain of Dystrophin Reveals Four Potential Hinge Segments That May Confer Flexibility. J. of Biological Chemistry. Mar. 1990, vol. 265, No. 8, pp. 4560–4566.

Monaco, et.al. An Explanation for the Phenotypic Differences Between Patients Bearing Partial Deletions of the DMD Locus. Genomics2, 1988, pp. 90–95.

Hoffman, et.al. Characterization of Dystrophin in Muscle––Biopsy Specimens From Patients with Duchenne's or Becker's Muscular Dystrophy. New England J. Medicine. May 26, 1988, vol. 318, No. 21, pp. 1363–1368.

Bulfield, et.al. X Chromosome–Linked Muscular Dystrophy (mdx) in the Mouse. Proc. Natl. Acad. Sci. USA. Feb. 1984, vol. 81, pp. 1189–1192.

(Continued)

*Primary Examiner*—Scott D. Priebe
*Assistant Examiner*—Brian Whiteman
(74) *Attorney, Agent, or Firm*—Steven J. Hultquist; Marianne Fuierer; Tristan Fuierer

(57) ABSTRACT

The present invention provides a series of novel dystrophin minigenes that retain the essential biological functions. The expression of the dystrophin minigenes may be controlled by a regulatory element along with a small polyadenylation signal. The entire gene expression cassettes may be readily packaged into a viral vector, preferably an AAV vector. The present invention further defines the minimal functional domains of dystrophin and provides ways to optimize and create new versions of dystrophin minigenes. Finally, the present invention provides a method of treatment for Duchenne muscular dystrophy (DMD) and Becker muscular dystrophy (BMD).

15 Claims, 8 Drawing Sheets-

OTHER PUBLICATIONS

Gussoni, et.al. The Fate of Individual MyoblastsAfter Transplantation Into Muscles of DMD Patients. Nature Medicine. Sep. 1997, vol. 3, No. 9, pp. 970–977.

Barton–Davis, et.al. Aminoglycoside Antibiotics Restore Dystrophin Function to Skeletal Muscles of mdx Mice, J. Clinical Investigation. Aug. 1999, vol. 104, No. 4, pp. 375–381.

Curiel, et.al. Strategies to Adapt Adenoviral Vectors for Targeted Delivery. Annals New York Acad. Sci. 1999, vol. 886, pp. 158–171.

Haj–Ahmad, et.al. Development of a Helper–Independent Human Adenovirus Vector and its Use in the Transfer of the Herpes Simplex Virus Thymidine Kinase Gene. J. of Virology. Jan. 1986, vol. 57, No. 1, pp. 267–273.

Ragot, et.al. Efficient Adenovirus–Mediated Transfer of a Human Minidystrophin Gene to Skeletal Muscle of mdx Mice. Nature. Feb. 18, 1993, vol. 361, pp. 647–650.

Howell, et.al. High–Level Dystrophin Expression after Adeno–Virus Mediated Dystrophin Minigene Transfer to Skeletal Muscle of Dystrophic Dogs: Prolongation of Expression With Immunosuppression. Human Gene Therapy. Mar. 1998, vol. 9, pp. 629–634.

Fink, et.al. Gene Transfer to Neurons Using Herpes Simplex Virus–Based Vectors. Annu. Rev. Neuroscience 1986, pp. 265–287.

Miller, A.Dusty Progress Toward Human Gene Therapy. Blood, J. of the American Soc. of Hematology, vol. 76, No. 2, pp. 271–278.

Naldini, et.al. In Vivo Gene Delivery and Stable Transduction of Nondividing Cells by a Lentiviral Vector. Science. Apr. 12, 1996, vol. 272, pp. 263–267.

Flotte, et.al. Gene Expression from Adeno–Associated Virus Vectors in Airway Epithelial Cells. Am J. Respiratory Cell and Molecular Biology. 1992, vol. 7, pp. 349–356.

Samulski, et.al. Helper–Free Stocks of Recombinant Adeno–Associated Viruses: Normal Integration Does Not Require Viral Gene Expression. J. of Virology. Sep. 1989, vol. 63, No. 9, pp. 3822–3828.

Xiao, et.al. Efficient Long–Term Gene Transfer into Muscle Tissue of Immunocompetent Mice by Adeno–Associated Virus Vector. J. of Virology. Nov. 1996, vol. 70, No. 11, pp. 8098–8108.

Kessler, et.al. Gene Delivery to Skeletal Muscle Results in Sustained Expression and Systemic Delivery of a Therapeutic Protein. Proc. Natl. Acad. Sci. USA. Nov. 1996, vol. 93, pp. 14082–14087.

Xiao, et.al. Adeno–Associated Virus as a Vector for Liver–Directed Gene Therapy. J. of Virology, Dec. 1998, vol. 72, No. 12, pp. 10222–10226.

Pruchnic, et.al. The Use of Adeno–Associated Virus to Circumvent the Maturation–Dependent Viral Transduction of Muscle Fibers. Human Gene Therapy. Mar. 1, 2000, vol. 11, pp. 521–536.

Greelish, et.al. Stable Restoration fo the Sarcoglycan Complex in Dystrophic Muscle Perfused With Histamine and a Recombinant Adeno–Associated Viral Vector. Nature Medicine. Apr. 1999, vol. 5, No. 4, pp. 439–443.

Song, et.al. Sustained Secretion of Human Alpha–1–Antitrypsin From Murine Muscle Transduced With Adeno–Associated Virus Vectors. Proc. Natl. Acad. Sci. USA. Nov. 1998, vol. 95, pp. 14384–14388.

Kay, et.al. Evidence for Gene Transfer and Expression of Factor IX in Haemophilia B Patients Treated with an AAV Vector. Nature Genetics. Mar. 2000, vol. 24, pp. 257–261.

Chen, et.al. Low–Dose Vaccinia Virus–Mediated Cytokine Gene Therapy of Glioma. J. of Immunotherapy. 2001, pp. 46–57.

Bledsoe, et.al. Cytokine Production in Motor Neurons by Poliovirus Replicon Vector Gene Therapy. Nature Biotechnology. Sep. 18, 2000, vol. 18, pp. 964–969.

Wahlfors, et.al. Evaluation of Recombinant Alphaviruses as Vectors in Gene Therapy. Gene Therapy. 2000, vol. 7, pp. 472–480.

Romano, et.al. Latest Developments in Gene Transfer Technology: Achievements, Perspectives, and Controversies over Therapeutic Applications. Stem Cells. 2000, vol. 18, pp. 19–39.

Lee, , et.al. Lipidic Vector Systems for Gene Transfer. Critical Reviews in Therapeutic Drug Carrier Systems. 1997, vol. 14, No. 2, pp. 173–206.

Zhang, et.al. Long–Term Expression of Human Alpha 1–Antitrypsin Gene in Mouse Liver Achieved by Intravenous Administration of Plasmid DNA Using a Hydrodynamics–Based Procedure. Gene Therapy. 2000, vol. 7, pp. 1344–1349.

Yamashita, et.al. Electroporation–Mediated Interleukin–12 Gene Therapy for Hepatocelular Carcinoma in the Mice Model. Cancer Research. Feb. 1, 2001, vol. 61, pp. 1005–1012.

Acsadi, et.al. Human Dystrophin Expression in mdx Mice After Intramuscular Injection of DNA Constructs. Nature. Aug. 29, 1991. vol. 352, pp. 815–818.

Rando, et.al. Rescue of Dystrophin Expression in mdx Mouse Muscle by RNA/DNA Oligonucleotides. Proc. Natl. Acad. Sci. US.A. May 9, 2000, vol. 97, No. 10, pp. 5363–5368.

Cox, et.al. Dp71 Can Restore the Dystrophin–Associated Glycoprotein Complex in Muscle but Fails to Prevent Dystrophy. Nature Genetics. Dec. 1994, vol. 8, pp. 333–339.

Greenberg, et.al. Exogenous Dp71 Restores the Levels of Dystrophin Associated Proteins but Does Not Alleviate Muscle Damage in mdx Mice. Nature Genetics. Dec. 1994, vol. 8, pp. 340–344.

Yuasa, et.al. Effective Restoration of Dystrophin–Associated Proteins in Vivo by Adenovirus–Mediated Transfer of Truncated Dystrophin CDNAs. FEBS. 1998, vol. 425, pp. 329–336.

Yamamoto, et.al. Immune Response to Adenovirus–Delivered Antigens Upregulates Utrophin and Results in Mitigation of Muscle Pathology in mdx Mice. Human Gene Therapy. Mar. 20, 2000, vol. 11, pp. 669–680.

Wu, et.al. Mutational Analysis of the Adeno–Associated Virus Type 2 (AAV2) Capsid Gene and Construction of AAV2 Vectors with Altered Tropism. J. of Virology. Sep. 2000, vol. 74, No. 18, pp. 8635–8647.

Girod, et.al. Genetic Capsid Modifications Allow Efficient Re–Targeting of Adeno–Associated Virus Type 2. Nature Medicine. Sep. 1999, vol. 5, No. 9, pp. 1052–1056.

Lebkowski, et.al. Adeno–Associated Virus: a Vector System for Efficient Introduction and Integration of DNA into a Variety of Mammalian Cell Types. Molecular and Cellular Biology. Oct. 1988, vol. 8, NO. 10, pp. 3988–3996.

Zhou, et.al. Adeno–Associated Virus 2–Mediated HIgh Efficiency Gene Transfer Into Immature and Mature Subsets of Hermatopoietic Progenitor Cells in Human Umbilical Cord Blood. J. Exp. Med., Jun. 1994, vol. 179, pp. 1867–1875.

England, et.al. Very Mild Muscular Dystrophy Associated with the Deletion of 46% of Dystrophin. Nature. Jan. 11, 1990, vol. 343, pp. 180–182.

Li, et.al. Synthetic Muscle Promoters: Activities Exceeding Naturally Occurring Regulatory Sequences. Nature Viotechnology. Mar. 1999, vol. 17, pp. 241–245.

Tinsley, et.al. Primary Structure of Dystrophin–Related Protein. Nature. Dec. 10, 1992, vol. 360, pp. 591–593.

Tinsley, et.al. Amelioration of the Dystrophic Phenotype of mdx Mice Using a Truncated Utrophin Transgene. Nov. 28, 1996, vol. 384, pp. 349–353.

Rafael, et.al. Skeletal Muscle–Specific Expression of a Utrophin Transgene Rescues Utrophin–Dystrophin Deficient Mice. Nature Genetics. May 19, 1998, vol. 19, pp. 79–82.

Li, et.al. rAAV Vector–mediated Sarcoglycan Gene Transfer in a Hamster Model for Limb Girdle Muscular Dystrophy. Gene Therapy. 1999, vol. 6, pp. 74–82.

Matsuda, et.al. Visualization of Dystrophic Muscle Fibers in Mdx Mouse by Vital Staining with Evans Blue: Evidence of Apoptosis in Dystrophin–Deficient Muscle. J. Biochem. 1995, vol. 118, pp. 959–964.

Shield, et.al. E–Box Sites and a Proximal Regulatory Region of the Muscle Creatine Kinase Gene Differentially Regulate Expression in Diverse Skeletal Muscles and Cardiac Muscle of Transgenic Mice. Moleuclar and Cellular Biology. Sep. 1996, vol. 16, No. 9, pp. 5058–5068.

Xiao, et. al. Production of High–Titer Recombinant Adeno–Associated Virus Vectors in the Absence of Helper Adenovirus J. of Virology. Mar. 1998, vol. 72, No. 3, pp. 2224–2232.

Chapter 12 Vectors for Gene Therapy, by Snyder, et.al. in Current Protocols in Human Genetics, eds. Dracopoli, et.al. [copyright 1996 John Wiley & Sons, Inc.], pp. 12.0.1–12.1.23.

Martin, et.al. Regeneration of Dystrophic Muscle Following Multiple Injections of Bupivacaine. Muscle & Nerve. Jun. 1998, vol. 11, pp. 588–596.

Muzyczka, N. Use of Adeno–Associated Virus as a General Transduction Vector for Mammalian Cells. Curr. Topics in Micro. and Immunol. 1992, vol. 158, pp. 97–129.

Deconinck, et.al. Expression of Truncated Utrophin Leads to Major Functional Improvements in Dystrophin–Deficient Muscles of Mice. Nature Medicine. Nov., 1997, vol. 3, No. 11, pp. 1216–1221.

Schwarze, et.al. In Vivo Protein Transduction: Delivery of a Biologically Active Protein into the Mouse. Science. Sep. 3, 1999, vol. 285, pp. 1569–1572.

Koenig, et.al. Complete Cloning of the Duchenne Muscular Dystrophy (DMD) cDNA and Preliminary Genomic Organization of the DMD Gene in Normal and Affected Individuals. Cell. Jul. 31, 1997, vol. 50, pp. 509–517.

"Modular flexibility of dystrophin: Implications for gene therapy of Duchenne muscular dystrophy"; Scott Q. Harper, et al.; Nature Medicine, vol. 8, No. 3, Mar. 2002; pp. 253–261.

Gene Therapy In Duchenne Muscular Dystropy, Koji Inui et al., Brain Dev. 1996, 18: 357–361.

Muscular Dystrophy, Eric P. Hoffman, Identification and Use of Genes for Diagnostics and Therapeutics, pp. 1050–1052, Arch Pathol Lab Med–vol. 123, Nov. 1999.

Developments in Gene Therapy for Muscular Dystrophy, Dennis Hartigan–O'Connor et al., Microscopy Research and Technique 48:223–238 (2000); 2000 Wiley–Liss, Inc.

Coiled–coil regions in the carboxy–terminal domains of dystrophin and related proteins: potentials for protein–protein interactions; Blake DJ et al, 20: 133–135; 1995, Elsevier Science Ltd 0968–0004/95/.

Function and Genetics of Dystrophin and Dystrophin–Related Proteins in Muscle; Derek J. Blake, et al., Physiol Rev 82: 291–329, 2002.

Dp71 can restore the dystrophin–associated glycoprotein complex in muscle but fails to prevent dystrophy, Gregor A. Cox et al., Nature Genetics, vol. 8, Dec. 1994.

Interleukin 6 Induces Overexpression of the Sarcolemmal Utrophin in Neonatal mdx Skeletal Muscle, Human Gene Therapy 13:509–518, Mar. 1, 2002, Keita Fujimore, et al.

Adeno–associated virus vector gene transfer and sarcolemmal expression of a 144 kDa micro–dystrophin . . . , Stewart A. Fabb, et al., Human Molecular Genetics 2002, vol. 11, No. 7, pp. 733–741.

Modular flexibility of dystrophin: Implications for gene therapy of Duchenne muscular dystrophy; Scott Q. Harper, et al., Nature Medicine, vol. 8, #3, Mar. 2002, pp. 253–261.

Structure of a WW domain containing fragment of dystrophin in complex with B–dystroglycan; nature structural biology, vol. 7, #8, Aug. 2000, pp. 634–638, Xin Huang, et al.

Conformation and Phasing of Dystrophin Structural Repeats, J. Mol. Biol. (1994) 235, 1271–1277, Edith Kahana, et al.

Physical Properties of Dystrophin Rod Domain, Cell Motility and the Cytoskeleton 36:246–252 (1997); Edith Kahana, et al.

The 2.0 A structure of the Second Calponin Homology Domain from the Actin–binding Region of the Dystrophin Homologue Utrophin, Nicholas H. Keep, et al.

Crystal Structure of the actin–binding region of utrophin reveals a head–to–tail dimer; Nicholas H Keep, et al., Research article, pp. 1539–1546.

Structure of the Utrophin Actin–binding Domain Bound to F–actin Reveals Binding by an Induced Fit Mechanism, J.Mol.Biol. (2000) 297, 465–480; Carolyn A. Moores, et al.

The structure of the N–terminal actin–binding domain of human dystrophin and how mutations in this domain may cause Duchenne or Becker muscular dystrophy; Fiona LM Norwood et al., Research article, pp. 481–491.

Proceedings of the National Academy of Sciences of the U.S.A., Wang et al., Dec. 5, 2000, vol. 97, #25, pp. 13461–14016.

Immune Response to Adenovirus–Delivered Antigens Upregulates Utrophin and Results in Mitigation of muscle pathology in mdx Mice; Kanji Yamamoto, et al., Human Gene Therapy, 11:669–680, Mar. 20, 2000, pp. 669–680.

Effective restoration of dystrophin–associated proteins in vivo by adenovirus–mediated transfer of truncated dystrophin cDNAs; Katsutoshi Yuasa, et al., FEBS Letters 425 (1998) 329–336.

* cited by examiner

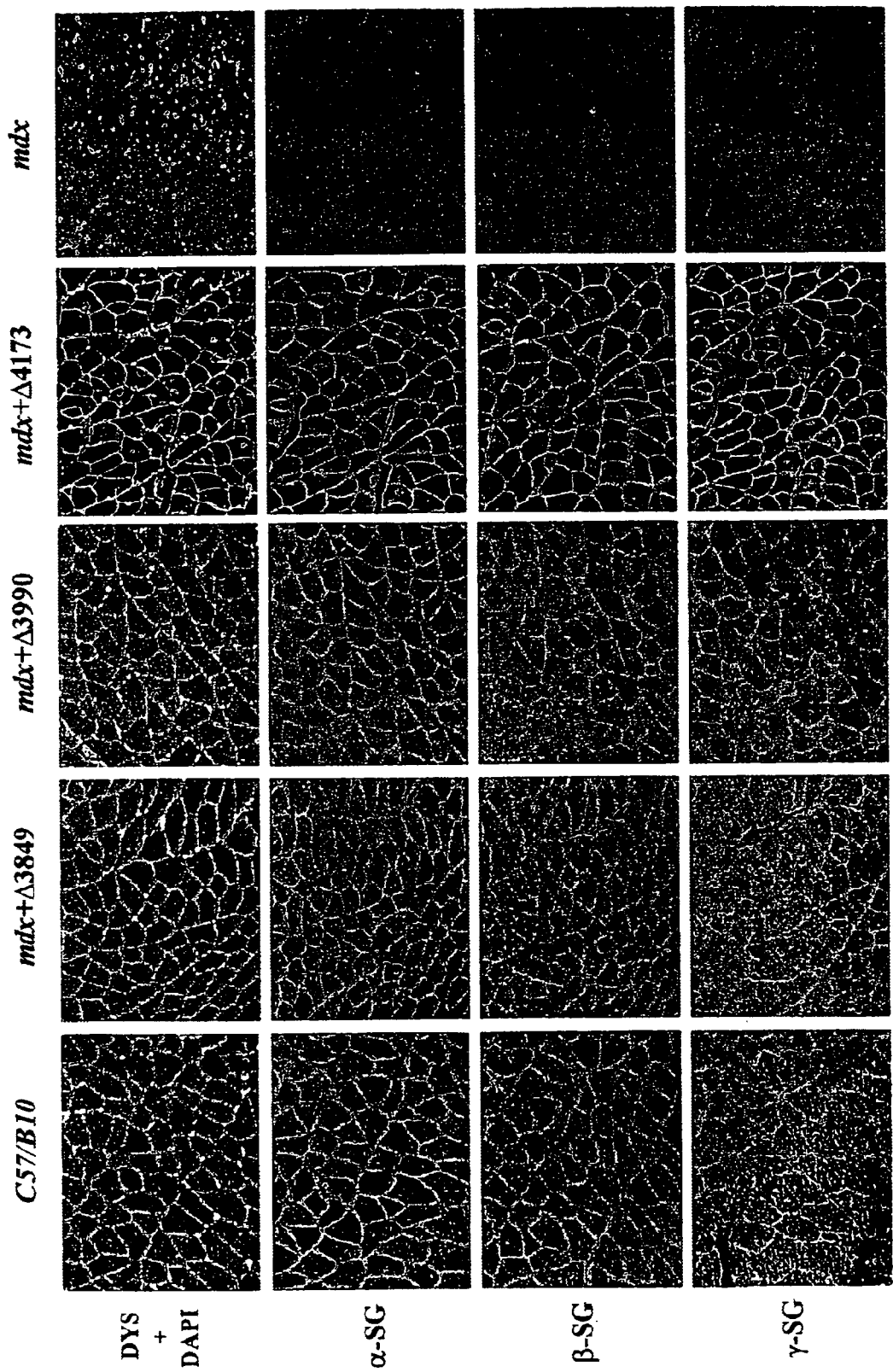

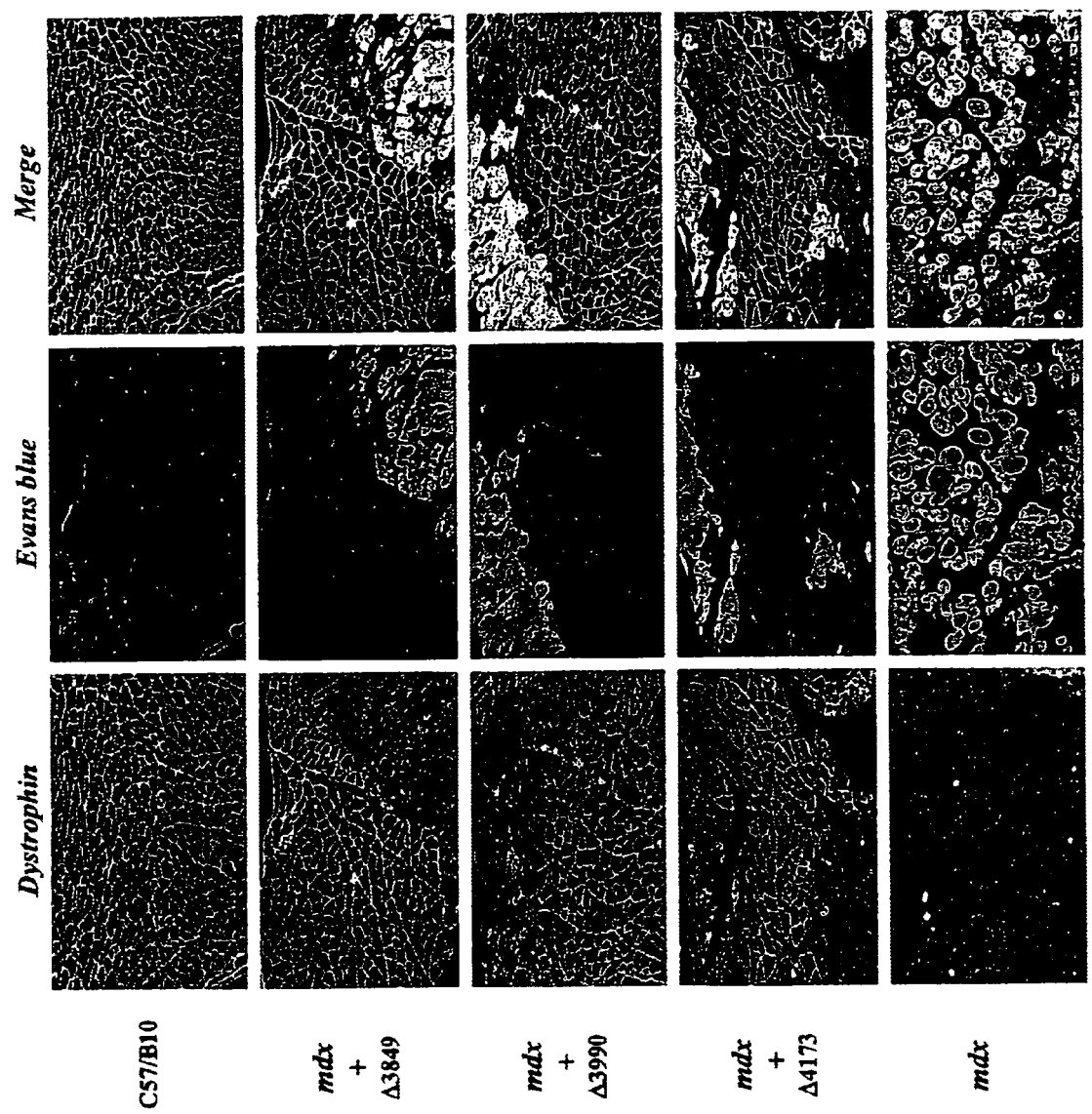

Mdx + Δ2796

Mdx + DysM3

SEQUENCE LISTING

<160> NUMBER OF SEQ ID NOS: 36

<210> SEQ ID NO 1
<211> LENGTH: 11058
<212> TYPE: DNA
<213> ORGANISM: Homo sapiens

<400> SEQUENCE: 1

| | | | | | |
|---|---|---|---|---|---|
| atgctttggt | gggaagaagt | agaggactgt | tatgaaagag | aagatgttca | aaagaaaaca | 60 |
| ttcacaaaat | gggtaaatgc | acaattttct | aagtttggga | agcagcatat | tgagaacctc | 120 |
| ttcagtgacc | tacaggatgg | gaggcgcctc | ctagacctcc | tcgaaggcct | gacagggcaa | 180 |
| aaactgccaa | agaaaaagg | atccacaaga | gttcatgccc | tgaacaatgt | caacaaggca | 240 |
| ctgcgggttt | tgcagaacaa | taatgttgat | ttagtgaata | ttggaagtac | tgacatcgta | 300 |
| gatggaaatc | ataaactgac | tcttggtttg | atttggaata | taatcctcca | ctggcaggtc | 360 |
| aaaaatgtaa | tgaaaaatat | catggctgga | ttgcaaccaa | ccaacagtga | aaagattctc | 420 |
| ctgagctggg | tccgacaatc | aactcgtaat | tatccacagg | ttaatgtaat | caacttcacc | 480 |
| accagctggt | ctgatggcct | ggctttgaat | gctctcatcc | atagtcatag | gccagaccta | 540 |
| tttgactgga | atagtgtggt | ttgccagcag | tcagccacac | aacgactgga | acatgcattc | 600 |
| aacatcgcca | gatatcaatt | aggcatagag | aaactactcg | atcctgaaga | tgttgatacc | 660 |
| acctatccag | ataagaagtc | catcttaatg | tacatcacat | cactcttcca | agttttgcct | 720 |
| caacaagtga | gcattgaagc | catccaggaa | gtggaaatgt | tgccaaggcc | acctaaagtg | 780 |
| actaaagaag | aacattttca | gttacatcat | caaatgcact | attctcaaca | gatcacggtc | 840 |
| agtctagcac | agggatatga | gagaacttct | tcccctaagc | ctcgattcaa | gagctatgcc | 900 |
| tacacacagg | ctgcttatgt | caccacctct | gaccctacac | ggagcccatt | tccttcacag | 960 |
| catttggaag | ctcctgaaga | caagtcattt | ggcagttcat | tgatggagag | tgaagtaaac | 1020 |
| ctggaccgtt | atcaaacagc | tttagaagaa | gtattatcgt | ggcttcttc | tgctgaggac | 1080 |
| acattgcaag | cacaaggaga | gatttctaat | gatgtggaag | tggtgaaaga | ccagtttcat | 1140 |
| actcatgagg | ggtacatgat | ggatttgaca | gcccatcagg | gccgggttgg | taatattcta | 1200 |
| caattgggaa | gtaagctgat | tggaacagga | aaattatcag | aagatgaaga | aactgaagta | 1260 |
| caagagcaga | tgaatctcct | aaattcaaga | tgggaatgcc | tcagggtagc | tagcatggaa | 1320 |
| aaacaaagca | atttacatag | agttttaatg | gatctccaga | atcagaaact | gaaagagttg | 1380 |
| aatgactggc | taacaaaaac | agaagaaaga | acaggaaaa | tggaggaaga | gcctcttgga | 1440 |
| cctgatcttg | aagacctaaa | acgccaagta | caacaacata | aggtgcttca | agaagatcta | 1500 |
| gaacaagaac | aagtcagggt | caattctctc | actcacatgg | tggtggtagt | tgatgaatct | 1560 |
| agtggagatc | acgcaactgc | tgctttggaa | gaacaactta | aggtattggg | agatcgatgg | 1620 |
| gcaaacatct | gtagatggac | agaagaccgc | tgggttcttt | tacaagacat | cctgctcaaa | 1680 |
| tggcaacgtc | ttactgaaga | acagtgcctt | tttagtgcat | ggcttttcaga | aaagaagat | 1740 |
| gcagtgaaca | agattcacac | aactggcttt | aaagatcaaa | atgaaatgtt | atcaagtctt | 1800 |
| caaaaactgg | ccgttttaaa | agcggatcta | gaaaagaaaa | agcaatccat | gggcaaactg | 1860 |
| tattcaatca | aacaagatct | tctttcaaca | ctgaagaata | agtcagtgac | ccagaagacg | 1920 |
| gaagcatggc | tggataactt | tgcccggtgt | tgggataatt | tagtccaaaa | acttgaaaag | 1980 |
| agtacagcac | agatttcaca | ggctgtcacc | accactcagc | catcactaac | acagacaact | 2040 |

-continued

| | |
|---|---|
| gtaatggaaa cagtaactac ggtgaccaca agggaacaga tcctggtaaa gcatgctcaa | 2100 |
| gaggaacttc caccaccacc tccccaaaag aagaggcaga ttactgtgga ttctgaaatt | 2160 |
| aggaaaaggt tggatgttga tataactgaa cttcacagct ggattactcg ctcagaagct | 2220 |
| gtgttgcaga gtcctgaatt tgcaatcttt cggaaggaag gcaacttctc agacttaaaa | 2280 |
| gaaaagtca atgccataga gcgagaaaaa gctgagaagt tcagaaaact gcaagatgcc | 2340 |
| agcagatcag gtcaggccct ggtggaacag atggtgaatg agggtgttaa tgcagatagc | 2400 |
| atcaaacaag cctcagaaca actgaacagc cggtggatcg aattctgcca gttgctaagt | 2460 |
| gagagactta actggctgga gtatcagaac aacatcatcg ctttctataa tcagctacaa | 2520 |
| caattggagc agatgacaac tactgctgaa aactggttga aaatccaacc caccacccca | 2580 |
| tcagagccaa cagcaattaa aagtcagtta aaaatttgta aggatgaagt caaccggcta | 2640 |
| tcaggtcttc aacctcaaat tgaacgatta aaaattcaaa gcatagccct gaaagagaaa | 2700 |
| ggacaaggac ccatgttcct ggatgcagac tttgtggcct ttacaaatca ttttaagcaa | 2760 |
| gtcttttctg atgtgcaggc cagagagaaa gagctacaga caattttttga cactttgcca | 2820 |
| ccaatgcgct atcaggagac catgagtgcc atcaggacat gggtccagca gtcagaaacc | 2880 |
| aaactctcca tacctcaact tagtgtcacc gactatgaaa tcatggagca gagactcggg | 2940 |
| gaattgcagg ctttacaaag ttctctgcaa gagcaacaaa gtggcctata ctatctcagc | 3000 |
| accactgtga agagatgtc gaagaaagcg ccctctgaaa ttagccggaa atatcaatca | 3060 |
| gaatttgaag aaattgaggg acgctggaag aagctctcct cccagctggt tgagcattgt | 3120 |
| caaaagctag aggagcaaat gaataaactc cgaaaaattc agaatcacat acaaaccctg | 3180 |
| aagaaatgga tggctgaagt tgatgttttt ctgaaggagg aatggcctgc ccttggggat | 3240 |
| tcagaaattc taaaaaagca gctgaaacag tgcagacttt tagtcagtga tattcagaca | 3300 |
| attcagccca gtctaaacag tgtcaatgaa ggtgggcaga agataaagaa tgaagcagag | 3360 |
| ccagagtttg cttcgagact tgagacagaa ctcaaagaac ttaacactca gtgggatcac | 3420 |
| atgtgccaac aggtctatgc cagaaaggag gccttgaagg gaggtttgga gaaaactgta | 3480 |
| agcctccaga aagatctatc agagatgcac gaatggatga cacaagctga agaagagtat | 3540 |
| cttgagagag atttttgaata taaaactcca gatgaattac agaaagcatt tgaagagatg | 3600 |
| aagagagcta agaagaggc ccaacaaaaa gaagcgaaag tgaaactcct tactgagtct | 3660 |
| gtaaatagtg tcatagctca agctccacct gtagcacaag aggcctttaaa aaaggaactt | 3720 |
| gaaactctaa ccaccaacta ccagtggctc tgcactaggc tgaatgggaa atgcaagact | 3780 |
| ttggaagaag tttgggcatg ttggcatgag ttattgtcat acttggagaa agcaaacaag | 3840 |
| tggctaaatg aagtagaatt taaacttaaa accactgaaa acattcctgg cggagctgag | 3900 |
| gaaatctctg aggtgctaga ttcacttgaa aatttgatgc acattcaga ggataaccca | 3960 |
| aatcagattc gcatattggc acagacccta acagatggcg gagtcatgga tgagctaatc | 4020 |
| aatgaggaac ttgagacatt taattctcgt tggagggaac tacatgaaga ggctgtaagg | 4080 |
| aggcaaaagt tgcttgaaca gagcatccag tctgcccagg agactgaaaa ttccttacac | 4140 |
| ttaatccagg agtccctcac attcattgac aagcagttgg cagcttatat tgcagacaag | 4200 |
| gtggacgcag ctcaaatgcc tcaggaagcc cagaaaatcc aatctgattt gacaagtcat | 4260 |
| gagatcagtt tagaagaaat gaagaaacat aatcagggga aggaggctgc ccaaagagtc | 4320 |
| ctgtctcaga ttgatgttgc acagaaaaaa ttacaagatg tctccatgaa gtttcgatta | 4380 |

-continued

```
ttccagaaac cagccaattt tgagcagcgt ctacaagaaa gtaagatgat tttagatgaa      4440
gtgaagatgc acttgcctgc attggaaaca aagagtgtgg aacaggaagt agtacagtca      4500
cagctaaatc attgtgtgaa cttgtataaa agtctgagtg aagtgaagtc tgaagtggaa      4560
atggtgataa agactggacg tcagattgta cagaaaaagc agacggaaaa tcccaaagaa      4620
cttgatgaaa gagtaacagc tttgaaattg cattataatg agctgggagc aaaggtaaca      4680
gaaagaaagc aacagttgga gaaatgcttg aaattgtccc gtaagatgcg aaaggaaatg      4740
aatgtcttga cagaatggct ggcagctaca gatatggaat tgacaaagag atcagcagtt      4800
gaaggaatgc ctagtaattt ggattctgaa gttgcctggg aaaggctac  tcaaaaagag      4860 attgagaaac agaaggtgca cctgaagagt atcacagagg taggagaggc cttgaaaaca      4920
gttttgggca agaaggagac gttggtgaaa gataaactca gtcttctgaa tagtaattgg      4980
atagctgtca cctcccgagc agaagagtgg ttaaatcttt tgttggaata ccagaaacac      5040
atggaaactt tgaccagaa  tgtggaccac atcacaaagt ggatcattca ggctgacaca      5100
cttttggatg aatcagagaa aaagaaaccc cagcaaaaag aagacgtgct taagcgttta      5160
aaggcagaac tgaatgacat acgcccaaag gtggactcta cacgtgacca agcagcaaac      5220
ttgatggcaa accacggtga ccactgcagg aaattagtag agccccaaat ctcagagctc      5280
aaccatcgat ttgcagccat ttcacacaga attaagactg aaaaggcctc cattcctttg      5340
aaggaattgg agcagtttaa ctcagatata caaaaattgc ttgaaccact ggaggctgaa      5400
attcagcagg gggtgaatct gaaagaggaa gacttcaata agatatgaa  tgaagacaat      5460 gagggtactg taaagaatt  gttgcaaaga ggagacaact acaacaaag  aatcacagat      5520 gagagaaaga gcgaggaaat aaagataaaa cagcagctgt tacagacaaa acataatgct      5580
ctcaaggatt tgaggtctca aagaagaaaa aaggctctag aaatttctca tcagtggtat      5640
cagtacaaga ggcaggctga tgatctcctg aaatgcttgg atgacattga aaaaaaatta      5700
gccagcctac ctgagcccag agatgaaagg aaaataaagg aaattgatcg ggaattgcag      5760
aagaagaaag aggagctgaa tgcagtgcgt aggcaagctg agggcttgtc tgaggatggg      5820
gccgcaatgg cagtggagcc aactcagatc cagctcagca gcgctggcg  ggaaattgag      5880 agcaaatttg ctcagtttcg aagactcaac tttgcacaaa ttcacactgt ccgtgaagaa      5940
acgatgatgg tgatgactga agacatgcct ttggaaattt cttatgtgcc ttctacttat      6000
ttgactgaaa tcactcatgt ctcacaagcc ctattagaag tggaacaact tctcaatgct      6060
cctgacctct gtgctaagga ctttgaagat ctctttaagc aagaggagtc tctgaagaat      6120 ataaagata  gtctacaaca aagctcaggt cggattgaca ttattcatag caagaagaca      6180
gcagcattgc aaagtgcaac gcctgtggaa agggtgaagc tacaggaagc tctctcccag      6240
cttgatttcc aatgggaaaa agttaacaaa atgtacaagg accgacaagg gcgatttgac      6300
agatctgttg agaaatggcg gcgttttcat tatgatataa agatatttaa tcagtggcta      6360
acagaagctg aacagtttct cagaaagaca caaattcctg agaattggga acatgctaaa      6420
tacaaatggt atcttaagga actccaggat ggcattgggc agcggcaaac tgttgtcaga      6480
acattgaatg caactgggga agaaataatt cagcaatcct caaaaacaga tgccagtatt      6540
ctacaggaaa aattgggaag cctgaatctg cggtggcagg aggtctgcaa acagctgtca      6600
gacagaaaaa agaggctaga gaacaaaag  aatatcttgt cagaatttca aagagattta      6660
aatgaatttg ttttatggtt ggaggaagca gataacattg ctagtatccc acttgaacct      6720
ggaaaagagc agcaactaaa agaaaagctt gagcaagtca agttactggt ggaagagttg      6780
```

-continued

```
cccctgcgcc agggaattct caaacaatta aatgaaactg gaggacccgt gcttgtaagt    6840
gctcccataa gcccagaaga gcaagataaa cttgaaaata agctcaagca gacaaatctc    6900
cagtggataa aggtttccag agctttacct gagaaacaag gagaaattga agctcaaata    6960
aaagaccttg ggcagcttga aaaaagctt gaagaccttg aagagcagtt aaatcatctg    7020
ctgctgtggt tatctcctat taggaatcag ttggaaattt ataaccaacc aaaccaagaa    7080
ggaccatttg acgttaagga aactgaaata gcagttcaag ctaaacaacc ggatgtggaa    7140
gagattttgt ctaaagggca gcatttgtac aaggaaaaac cagccactca gccagtgaag    7200
aggaagttag aagatctgag ctctgagtgg aaggcggtaa accgtttact tcaagagctg    7260
agggcaaagc agcctgacct agctcctgga ctgaccacta ttggagcctc tcctactcag    7320
actgttactc tggtgacaca acctgtggtt actaaggaaa ctgccatctc caaactagaa    7380
atgccatctt ccttgatgtt ggaggtacct gctctggcag atttcaaccg ggcttggaca    7440
gaacttaccg actggctttc tctgcttgat caagttataa aatcacagag ggtgatggtg    7500
ggtgaccttg aggatatcaa cgagatgatc atcaagcaga aggcaacaat gcaggatttg    7560
gaacagaggc gtccccagtt ggaagaactc attaccgctg cccaaaattt gaaaaacaag    7620
accagcaatc aagaggctag aacaatcatt acgatcgaa ttgaaagaat tcagaatcag    7680
tgggatgaag tacaagaaca ccttcagaac cggaggcaac agttgaatga aatgttaaag    7740
gattcaacac aatggctgga agctaaggaa gaagctgagc aggtcttagg acaggccaga    7800
gccaagcttg agtcatggaa ggagggtccc tatacagtag atgcaatcca aaagaaaatc    7860
acagaaacca agcagttggc caaagaccct cgccagtggc agacaaatgt agatgtggca    7920
aatgacttgg ccctgaaact tctccgggat tattctgcag atgataccag aaaagtccac    7980
atgataacag agaatatcaa tgcctcttgg agaagcattc ataaaagggt gagtgagcga    8040
gaggctgctt tggaagaaac tcatagatta ctgcaacagt tccccctgga cctgaaaaag    8100
tttcttgcct ggcttacaga agctgaaaca actgccaatg tcctacagga tgctacccgt    8160
aaggaaaggc tcctagaaga ctccaaggga gtaaaagagc tgatgaaaca atggcaagac    8220
ctccaaggtg aaattgaagc tcacacagat gtttatcaca acctggatga aaacagccaa    8280
aaaatcctga gatccctgga aggttccgat gatgcagtcc tgttacaaag acgtttggat    8340
aacatgaact tcaagtggag tgaacttcgg aaaaagtctc tcaacattag gtcccatttg    8400
gaagccagtt ctgaccagtg gaagcgtctg cacctttctc tgcaggaact tctggtgtgg    8460
ctacagctga agatgatga attaagccgg caggcaccta ttggaggcga ctttccagca    8520
gttcagaagc agaacgatgt acatagggcc ttcaagaggg aattgaaaac taaagaacct    8580
gtaatcatga gtactcttga gactgtacga atatttctga cagagcagcc tttggaagga    8640
ctagagaaac tctaccagga gcccagagag ctgcctcctg aggagagagc ccagaatgtc    8700
actcggcttc tacgaaagca ggctgaggag gtcaatactg agtgggaaaa attgaacctg    8760
cactccgctg actggcagag aaaaatagat gagacccttg aaagactcca ggaacttcaa    8820
gaggccacgg atgagctgga cctcaagctg cgccaagctg aggtgatcaa gggatcctgg    8880
cagcccgtgg gcgatctcct cattgactct ctccaagatc acctcgagaa agtcaaggca    8940
cttcgaggag aaattgcgcc tctgaaagag aacgtgagcc acgtcaatga ccttgctcgc    9000
cagcttacca ctttgggcat tcagctctca ccgtataacc tcagcactct ggaagacctg    9060
aacaccagat ggaagcttct gcaggtgcc gtcgaggacc gagtcaggca gctgcatgaa    9120
```

```
gcccacaggg actttggtcc agcatctcag cactttcttt ccacgtctgt ccagggtccc    9180
tgggagagag ccatctcgcc aaacaaagtg ccctactata tcaaccacga gactcaaaca    9240
acttgctggg accatcccaa aatgacagag ctctaccagt ctttagctga cctgaataat    9300
gtcagattct cagcttatag gactgccatg aaactccgaa gactgcagaa ggcccttttgc   9360 ttggatctct tgagcctgtc agctgcatgt gatgccttgg accagcacaa cctcaagcaa    9420
aatgaccagc ccatggatat cctgcagatt attaattgtt tgaccactat ttatgaccgc    9480
ctggagcaag agcacaacaa tttggtcaac gtccctctct gcgtggatat gtgtctgaac    9540
tggctgctga atgtttatga tacgggacga acagggagga tccgtgtcct gtcttttaaa    9600
actggcatca tttccctgtg taaagcacat ttggaagaca agtacagata ccttttcaag    9660
caagtggcaa gttcaacagg attttgtgac cagcgcaggc tgggcctcct tctgcatgat    9720
tctatccaaa ttccaagaca gttgggtgaa gttgcatcct ttgggggcag taacattgag    9780
ccaagtgtcc ggagctgctt ccaatttgct aataataagc cagagatcga agcggccctc    9840
ttcctagact ggatgagact ggaaccccag tccatggtgt ggctgcccgt cctgcacaga    9900
gtggctgctg cagaaactgc caagcatcag gccaaatgta acatctgcaa agagtgtcca    9960
atcattggat tcaggtacag gagtctaaag cactttaatt atgacatctg ccaaagctgc   10020 ttttttttctg gtcgagttgc aaaaggccat aaaatgcact atcccatggt ggaatattgc   10080
actccgacta catcaggaga agatgttcga gactttgcca aggtactaaa aaacaaattt   10140
cgaaccaaaa ggtattttgc gaagcatccc cgaatgggct acctgccagt gcagactgtc   10200 ttagagggg acaacatgga aactcccgtt actctgatca acttctggcc agtagattct   10260
gcgcctgcct cgtcccctca gctttcacac gatgatactc attcacgcat tgaacattat   10320
gctagcaggc tagcagaaat ggaaaacagc aatggatctt atctaaatga tagcatctct   10380
cctaatgaga gcatagatga tgaacatttg ttaatccagc attactgcca aagtttgaac   10440
caggactccc ccctgagcca gcctcgtagt cctgcccaga tcttgatttc cttagagagt   10500
gaggaaagag gggagctaga gagaatccta gcagatcttg aggaagaaaa caggaatctg   10560
caagcagaat atgaccgtct aaagcagcag cacgaacata aaggcctgtc cccactgccg   10620 tccccctcctg aaatgatgcc cacctctccc cagagtcccc gggatgctga gctcattgct   10680
gaggccaagc tactgcgtca acacaaaggc cgcctggaag ccaggatgca aatcctggaa   10740
gaccacaata aacagctgga gtcacagtta cacaggctaa ggcagctgct ggagcaaccc   10800
caggcagagg ccaaagtgaa tggcacaacg gtgtcctctc cttctacctc tctacagagg   10860
tccgacagca gtcagcctat gctgctccga gtggttggca gtcaaacttc ggactccatg   10920
ggtgaggaag atcttctcag tcctccccag gacacaagca cagggttaga ggaggtgatg   10980
gagcaactca caactccctt ccctagttca agaggaagaa ataccccctgg aaagccaatg   11040 agagaggaca caatgtag                                                  11058

<210> SEQ ID NO 2
<211> LENGTH: 4182
<212> TYPE: DNA
<213> ORGANISM: Homo sapiens

<400> SEQUENCE: 2
attttcacca tggtttggtg ggaagaagta gaggactgtt atgaaagaga agatgttcaa      60
aagaaaacat tcacaaaatg ggtaaatgca caatttttcta agtttgggaa gcagcatatt     120
gagaacctct tcagtgacct acaggatggg aggcgcctcc tagacctcct cgaaggcctg     180
```

-continued

```
acagggcaaa aactgccaaa agaaaaagga tccacaagag ttcatgccct gaacaatgtc    240
aacaaggcac tgcgggtttt gcagaacaat aatgttgatt tagtgaatat tggaagtact    300
gacatcgtag atggaaatca taaactgact cttggtttga tttggaatat aatcctccac    360
tggcaggtca aaaatgtaat gaaaaatatc atggctggat tgcaacaaac caacagtgaa    420
aagattctcc tgagctgggt ccgacaatca actcgtaatt atccacaggt taatgtaatc    480
aacttcacca ccagctggtc tgatggcctg gctttgaatg ctctcatcca tagtcatagg    540
ccagacctat ttgactggaa tagtgtggtt tgccagcagt cagccacaca acgactggaa    600
catgcattca acatcgccag atatcaatta ggcatagaga aactactcga tcctgaagat    660
gttgatacca cctatccaga taagaagtcc atcttaatgt acatcacatc actcttccaa    720
gttttgcctc aacaagtgag cattgaagcc atccaggaag tggaaatgtt gccaaggcca    780
cctaaagtga ctaaagaaga acattttcag ttacatcatc aaatgcacta ttctcaacag    840
atcacggtca gtctagcaca gggatatgag agaacttctt cccctaagcc tcgattcaag    900
agctatgcct acacacaggc tgcttatgtc accacctctg accctacacg agcccattt     960 ccttcacagc atttggaagc tcctgaagac aagtcatttg gcagttcatt gatggagagt   1020
gaagtaaacc tggaccgtta tcaaacagct ttagaagaag tattatcgtg gcttcttttct  1080 gctgaggaca cattgcaagc acaaggagag atttctaatg atgtggaagt ggtgaaagac   1140
cagtttcata ctcatgaggg gtacatgatg gatttgacag cccatcaggg ccgggttggt   1200
aatattctac aattgggaag taagctgatt ggaacaggaa aattatcaga agatgaagaa   1260
actgaagtac aagagcagat gaatctccta aattcaagat gggaatgcct cagggtagct   1320
agcatggaaa acaaagcaa tttacataga gttttaatgg atctccagaa tcagaaactg    1380
aaagagttga atgactggct aacaaaaaca gaagaaagaa caaggaaaat ggaggaagag   1440
cctcttggac ctgatcttga agacctaaaa cgccaagtac aacaacataa ggtgcttcaa   1500
gaagatctag aacaagaaca agtcagggtc aattctctca ctcacatggt ggtggtagtt   1560
gatgaatcta gtggagatca cgcaactgct gctttggaag aacaacttaa ggtattggga   1620
gatcgatggg caaacatctg tagatggaca gaagaccgct gggttctttt acaagacatc   1680
cttctcaaat ggcaacgtct tactgaagaa cagtgccttt ttagtgcatg gctttcagaa   1740
aaagaagatg cagtgaacaa gattcacaca actggcttta aagatcaaaa tgaaatgtta   1800
tcaagtcttc aaaaactggc cgttttaaaa gcggatctag aaaagaaaaa gcaatccatg   1860
ggcaaactgt attcactcaa acaagatctt cttttcaacac tgaagaataa gtcagtgacc   1920
cagaagacgg aagcatggct ggataacttt gcccggtgtt gggataattt agtccaaaaa   1980
cttgaaaaga gtacagcaca gactcataga ttactgcaac agttcccccct ggacctggaa   2040 aagtttcttg cctggcttac agaagctgaa acaactgcca atgtcctaca ggatgctacc   2100
cgtaaggaaa ggctcctaga agactccaag ggagtaaaag agctgatgaa acaatggcaa   2160
gacctccaag gtgaaattga agctcacaca gatgtttatc acaacctgga tgaaaacagc   2220
caaaaaatcc tgagatccct ggaaggttcc gatgatgcag tcctgttaca aagacgtttg   2280
gataacatga acttcaagtg gagtgaactt cggaaaaagt ctctcaacat taggtcccat   2340
ttggaagcca gttctgacca gtggaagcgt ctgcaccttt ctctgcagga acttctggtg   2400
tggctacagc tgaaagatga tgaattaagc cggcaggcac ctattggagg cgactttcca   2460
gcagttcaga agcagaacga tgtacatagg gccttcaaga gggaattgaa aactaaagaa   2520
```

-continued

| | |
|---|---|
| cctgtaatca tgagtactct tgagactgta cgaatatttc tgacagagca gcctttggaa | 2580 |
| ggactagaga aactctacca ggagcccaga gagctgcctc ctgaggagag agcccagaat | 2640 |
| gtcactcggc ttctacgaaa gcaggctgag gaggtcaata ctgagtggga aaaattgaac | 2700 |
| ctgcactccg ctgactggca gagaaaaata gatgagaccc ttgaaagact ccaggaactt | 2760 |
| caagaggcca cggatgagct ggacctcaag ctgcgccaag ctgaggtgat caagggatcc | 2820 |
| tggcagcccg tgggcgatct cctcattgac tctctccaag atcacctcga gaaagtcaag | 2880 |
| gcacttcgag gagaaattgc gcctctgaaa gagaacgtga gccacgtcaa tgaccttgct | 2940 |
| cgccagctta ccactttggg cattcagctc tcaccgtata acctcagcac tctggaagac | 3000 |
| ctgaacacca gatggaagct tctgcaggtg gccgtcgagg accgagtcag gcagctgcat | 3060 |
| gaagcccaca gggactttgg tccagcatct cagcactttt tttccacgtc tgtccagggt | 3120 |
| ccctgggaga gagccatctc gccaaacaaa gtgccctact atatcaacca cgagactcaa | 3180 |
| acaacttgct gggaccatcc caaaatgaca gagctctacc agtctttagc tgacctgaat | 3240 |
| aatgtcagat tctcagctta taggactgcc atgaaactcc gaagactgca gaaggccctt | 3300 |
| tgcttggatc tcttgagcct gtcagctgca tgtgatgcct tggaccagca caacctcaag | 3360 |
| caaaatgacc agcccatgga tatcctgcag attattaatt gtttgaccac tatttatgac | 3420 |
| cgcctggagc aagagcacaa caatttggtc aacgtccctc tctgcgtgga tatgtgtctg | 3480 |
| aactggctgc tgaatgttta tgatacggga cgaacaggga ggatccgtgt cctgtctttt | 3540 |
| aaaactggca tcatttccct gtgtaaagca catttggaag acaagtacag ataccttttc | 3600 |
| aagcaagtgg caagttcaac aggatttttgt gaccagcgca ggctgggcct ccttctgcat | 3660 |
| gattctatcc aaattccaag acagttgggt gaagttgcat cctttggggg cagtaacatt | 3720 |
| gagccaagtg tccggagctg cttccaattt gctaataata agccagagat cgaagcggcc | 3780 |
| ctcttcctag actggatgag actggaaccc cagtccatgg tgtggctgcc cgtcctgcac | 3840 |
| agagtggctg ctgcagaaac tgccaagcat caggccaaat gtaacatctg caaagagtgt | 3900 |
| ccaatcattg gattcaggta caggagtcta aagcacttta attatgacat ctgccaaagc | 3960 |
| tgctttttt ctggtcgagt tgcaaaaggc cataaaatgc actatcccat ggtggaatat | 4020 |
| tgcactccga ctacatcagg agaagatgtt cgagactttg ccaaggtact aaaaaacaaa | 4080 |
| tttcgaacca aaggtatttt tgcgaagcat ccccgaatgg gctacctgcc agtgcagact | 4140 |
| gtcttagagg gggacaacat ggaaactccc gacacaatgt ag | 4182 |

<210> SEQ ID NO 3
<211> LENGTH: 1991
<212> TYPE: DNA
<213> ORGANISM: Homo sapiens

<400> SEQUENCE: 3

| | |
|---|---|
| atgctttggt gggaagaagt agaggactgt tatgaaagag aagatgttca aagaaaaca | 60 |
| ttcacaaaat gggtaaatgc acaattttct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata atcctccaa ctggcaggtc | 360 |
| aaaaatgtaa tgaaaatat catggctgga ttgcaaccaa ccaacagtga aaagattctc | 420 |
| ctgagctggg tccgacaatc aactcgtaat tatccacagg ttaatgtaat caacttcacc | 480 |

-continued

```
accagctggt ctgatggcct ggcttttgaat gctctcatcc atagtcatag gccagaccta    540
tttgactgga atagtgtggt ttgccagcag tcagccacac aacgactgga acatgcattc    600
aacatcgcca gatatcaatt aggcatagag aaactactcg atcctgaaga tgttgatacc    660
acctatccag ataagaagtc catcttaatg tacatcacat cactcttcca agttttgcct    720
caacaagtga gcattgaagc catccaggaa gtggaaatgt tgccaaggcc acctaaagtg    780
actaagaag aacattttca gttacatcat caaatgcact attctcaaca gatcacggtc    840
agtctagcac agggatatga gagaacttct tcccctaagc ctcgattcaa gagctatgcc    900
tacacacagg ctgcttatgt caccaccctct gaccctacac ggagcccatt tccttcacag    960
catttggaag ctcctgaaga caagtcattt ggcagttcat tgatggagag tgaagtaaac   1020
ctggaccgtt atcaaacagc tttagaagaa gtattatcgt ggcttctttc tgctgaggac   1080
acattgcaag cacaaggaga gatttctaat gatgtggaag tggtgaaaga ccagtttcat   1140
actcatgagg ggtacatgat ggatttgaca gcccatcagg gccgggttgg taatattcta   1200
caattgggaa gtaagctgat tggaacagga aaattatcag aagatgaaga aactgaagta   1260
caagagcaga tgaatctcct aaattcaaga tgggaatgcc tcagggtagc tagcatggaa   1320
aaacaaagca atttacatag agttttaatg gatctccaga atcagaaact gaaagagttg   1380
aatgactggc taacaaaaac agaagaaaga acaaggaaaa tggaggaaga gcctcttgga   1440
cctgatcttg aagacctaaa acgccaagta caacaacata aggtgcttca agaagatcta   1500
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacat cctgctcaaa   1680
tggcaacgtc ttactgaaga acagtgcctt tttagtgcat ggctttcaga aaaagaagat   1740
gcagtgaaca agattcacac aactggcttt aaagatcaaa atgaaatgtt atcaagtctt   1800
caaaaactgg ccgttttaaa agcggatcta gaaaagaaaa agcaatccat gggcaaactg   1860
tattcaatca aacaagatct tctttcaaca ctgaagaata agtcagtgac ccagaagacg   1920
gaagcatggc tggataactt tgcccggtgt tgggataatt tagtccaaaa acttgaaaag   1980
agtacagcac a                                                        1991
```

<210> SEQ ID NO 4
<211> LENGTH: 2169
<212> TYPE: DNA
<213> ORGANISM: Homo sapiens
<400> SEQUENCE: 4

```
aactcataga ttactgcaac agttcccccct ggacctggaa aagtttcttg cctggcttac     60
agaagctgaa acaactgcca atgtcctaca ggatgctacc cgtaaggaaa ggctcctaga    120
agactccaag ggagtaaaag agctgatgaa acaatggcaa gacctccaag gtgaaattga    180
agctcacaca gatgttttatc acaacctgga tgaaaacagc caaaaaatcc tgagatccct    240
ggaaggttcc gatgatgcag tcctgttaca aagacgtttg gataacatga acttcaagtg    300
gagtgaactt cggaaaaagt ctctcaacat taggtcccat ttggaagcca gttctgacca    360
gtggaagcgt ctgcaccttt tctctgcagga acttctggtg tggctacagc tgaaagatga    420
tgaattaagc cggcaggcac ctattggagg cgactttcca gcagttcaga agcagaacga    480
tgtacatagg gccttcaaga gggaattgaa aactaaagaa cctgtaatca tgagtactct    540
```

-continued

```
tgagactgta cgaatatttc tgacagagca gcctttggaa ggactagaga aactctacca        600
ggagcccaga gagctgcctc ctgaggagag agcccagaat gtcactcggc ttctacgaaa        660
gcaggctgag gaggtcaata ctgagtggga aaaattgaac ctgcactccg ctgactggca        720
gagaaaaata gatgagaccc ttgaaagact ccaggaactt caagaggcca cggatgagct        780
ggacctcaag ctgcgccaag ctgaggtgat caagggatcc tggcagcccg tgggcgatct        840
cctcattgac tctctccaag atcacctcga gaaagtcaag gcacttcgag agaaaattgc        900
gcctctgaaa gagaacgtga gccacgtcaa tgaccttgct cgccagctta ccactttggg        960
cattcagctc tcaccgtata acctcagcac tctggaagca ctgaacacca gatggaagct       1020
tctgcaggtg gccgtcgagg accgagtcag gcagctgcat gaagcccaca gggactttgg       1080
tccagcatct cagcactttc tttccacgtc tgtccaggt ccctgggaga gagccatctc        1140
gccaaacaaa gtgccctact atatcaacca cgagactcaa acaacttgct gggaccatcc       1200
caaaatgaca gagctctacc agtctttagc tgacctgaat aatgtcagat ctcagctta        1260 taggactgcc atgaaactcc gaagactgca gaaggccctt tgcttggatc tcttgagcct       1320
gtcagctgca tgtgatgcct tggaccagca caacctcaag caaaatgacc agcccatgga       1380
tatcctgcag attattaatt gtttgaccac tatttatgac cgcctggagc aagagcacaa       1440
caatttggtc aacgtccctc tctgcgtgga tatgtgtctg aactggctgc tgaatgttta       1500
tgatacggga cgaacaggga ggatccgtgt cctgtctttt aaaactggca tcatttccct       1560
gtgtaaagca catttggaag acaagtacag ataccttttc aagcaagtgg caagttcaac       1620
aggattttgt gaccagcgca ggctgggcct ccttctgcat gattctatcc aaattccaag       1680
acagttgggt gaagttgcat cctttggggg cagtaacatt gagccaagtg tccggagctg       1740
cttccaattt gctaataata agccagagat cgaagcggcc ctcttcctag actggatgag       1800
actggaaccc cagtccatgg tgtggctgcc cgtcctgcac agagtggctg ctgcagaaac       1860
tgccaagcat caggccaaat gtaacatctg caaagagtgt ccaatcattg gattcaggta       1920
caggagtcta aagcacttta attatgacat ctgccaaagc tgcttttttt ctggtcgagt       1980
tgcaaaaggc cataaaatgc actatcccat ggtggaatat tgcactccga ctacatcagg       2040
agaagatgtt cgagacttg ccaaggtact aaaaaacaaa tttcgaacca aaaggtatt         2100 tgcgaagcat ccccgaatgg gctacctgcc agtgcagact gtcttagagg gggacaacat       2160
ggaaactcc                                                                2169
```

<210> SEQ ID NO 5
<211> LENGTH: 12
<212> TYPE: DNA
<213> ORGANISM: Homo sapiens

<400> SEQUENCE: 5

```
ggacacaatg ta                                                              12
```

<210> SEQ ID NO 6
<211> LENGTH: 3999
<212> TYPE: DNA
<213> ORGANISM: Homo sapiens

<400> SEQUENCE: 6

```
attttcacca tggtttggtg ggaagaagta gaggactgtt atgaaagaga agatgttcaa         60
aagaaaacat tcacaaaatg ggtaaatgca caatttttcta agtttgggaa gcagcatatt       120
gagaacctct tcagtgacct acaggatggg aggcgcctcc tagacctcct cgaaggcctg       180
```

```
acagggcaaa aactgccaaa agaaaaagga tccacaagag ttcatgccct gaacaatgtc    240
aacaaggcac tgcgggtttt gcagaacaat aatgttgatt tagtgaatat tggaagtact    300
gacatcgtag atggaaatca taaactgact cttggtttga tttggaatat aatcctccac    360
tggcaggtca aaatgtaat gaaaaatatc atggctggat tgcaacaaac caacagtgaa    420
aagattctcc tgagctgggt ccgacaatca actcgtaatt atccacaggt taatgtaatc    480
aacttcacca ccagctggtc tgatggcctg gctttgaatg ctctcatcca tagtcatagg    540
ccagacctat ttgactggaa tagtgtggtt tgccagcagt cagccacaca acgactggaa    600
catgcattca acatcgccag atatcaatta ggcatagaga aactactcga tcctgaagat    660
gttgatacca cctatccaga taagaagtcc atcttaatgt acatcacatc actcttccaa    720
gttttgcctc aacaagtgag cattgaagcc atccaggaag tggaaatgtt gccaaggcca    780
cctaaagtga ctaaagaaga acattttcag ttacatcatc aaatgcacta ttctcaacag    840
atcacggtca gtctagcaca gggatatgag agaacttctt cccctaagcc tcgattcaag    900
agctatgcct acacacaggc tgcttatgtc accacctctg accctacacg gagcccattt    960
ccttcacagc atttggaagc tcctgaagac aagtcatttg gcagttcatt gatggagagt   1020
gaagtaaacc tggaccgtta tcaaacagct ttagaagaag tattatcgtg gcttctttct   1080
gctgaggaca cattgcaagc acaaggagag atttctaatg atgtggaagt ggtgaaagac   1140
cagtttcata tctcatgaggg gtacatgatg gatttgacag cccatcaggg ccgggttggt   1200
aatattctac aattgggaag taagctgatt ggaacaggaa aattatcaga agatgaagaa   1260
actgaagtac aagagcagat gaatctccta aattcaagat gggaatgcct cagggtagct   1320
agcatggaaa acaaagcaa tttacataga gttttaatgg atctccagaa tcagaaactg   1380
aaagagttga atgactggct aacaaaaaca gaagaaagaa caaggaaaat ggaggaagag   1440
cctcttggac ctgatcttga agacctaaaa cgccaagtac aacaacataa ggtgcttcaa   1500
gaagatctag aacaagaaca agtcagggtc aattctctca ctcacatggt ggtggtagtt   1560
gatgaatcta gtggagatca cgcaactgct gctttggaag aacaacttaa ggtattggga   1620
gatcgatggg caaacatctg tagatggaca gaagaccgct gggttctttt acaagaccag   1680
cctgacctag ctcctggact gaccactatt ggagcctctc ctactcagac tgttactctg   1740
gtgacacaac ctgtggttac taaggaaact gccatctcca aactagaaat gccatcttcc   1800
ttgatgttgg aggtacctac tcatagatta ctgcaacagt tcccccctgga cctggaaaag   1860 tttcttgcct ggcttacaga agctgaaaca actgccaatg tcctacagga tgctacccgt   1920
aaggaaaggc tcctagaaga ctccaaggga gtaaaagagc tgatgaaaca atggcaagac   1980
ctccaaggtg aaattgaagc tcacacagat gtttatcaca acctggatga aacagccaa   2040 aaaatcctga gatccctgga aggttccgat gatgcagtcc tgttacaaag acgtttggat   2100
aacatgaact tcaagtggag tgaacttcgg aaaaagtctc tcaacattag gtcccatttg   2160
gaagccagtt ctgaccagtg gaagcgtctg caccttttctc tgcaggaact tctggtgtgg   2220
ctacagctga aagatgatga attaagccgg caggcaccta ttggaggcga ctttccagca   2280
gttcagaagc agaacgatgt acatagggcc ttcaagaggg aattgaaaac taaagaacct   2340
gtaatcatga gtactcttga gactgtacga atatttctga cagagcagcc tttggaagga   2400
ctagagaaac tctaccagga gcccagagag ctgcctcctg aggagagagc ccagaatgtc   2460
actcggcttc tacgaaagca ggctgaggag gtcaatactg agtgggaaaa attgaacctg   2520
```

-continued

| | |
|---|---|
| cactccgctg actggcagag aaaaatagat gagacccttg aaagactcca ggaacttcaa | 2580 |
| gaggccacgg atgagctgga cctcaagctg cgccaagctg aggtgatcaa gggatcctgg | 2640 |
| cagcccgtgg gcgatctcct cattgactct ctccaagatc acctcgagaa agtcaaggca | 2700 |
| cttcgaggag aaattgcgcc tctgaaagag aacgtgagcc acgtcaatga ccttgctcgc | 2760 |
| cagcttacca ctttgggcat tcagctctca ccgtataacc tcagcactct ggaagacctg | 2820 |
| aacaccagat ggaagcttct gcaggtggcc gtcgaggacc gagtcaggca gctgcatgaa | 2880 |
| gcccacaggg actttggtcc agcatctcag cactttcttt ccacgtctgt ccagggtccc | 2940 |
| tgggagagag ccatctcgcc aaacaaagtg ccctactata tcaaccacga gactcaaaca | 3000 |
| acttgctggg accatcccaa aatgacagag ctctaccagt ctttagctga cctgaataat | 3060 |
| gtcagattct cagcttatag gactgccatg aaactccgaa gactgcagaa ggcccttttgc | 3120 |
| ttggatctct tgagcctgtc agctgcatgt gatgccttgg accagcacaa cctcaagcaa | 3180 |
| aatgaccagc ccatggatat cctgcagatt attaattgtt tgaccactat ttatgaccgc | 3240 |
| ctggagcaag agcacaacaa tttggtcaac gtccctctct gcgtggatat gtgtctgaac | 3300 |
| tggctgctga atgtttatga tacgggacga acagggagga tccgtgtcct gtcttttaaa | 3360 |
| actggcatca tttccctgtg taaagcacat ttggaagaca agtacagata ccttttcaag | 3420 |
| caagtggcaa gttcaacagg attttgtgac cagcgcaggc tgggcctcct tctgcatgat | 3480 |
| tctatccaaa ttccaagaca gttgggtgaa gttgcatcct tgggggcag taacattgag | 3540 |
| ccaagtgtcc ggagctgctt ccaatttgct aataataagc cagagatcga agcggccctc | 3600 |
| ttcctagact ggatgagact ggaaccccag tccatggtgt ggctgcccgt cctgcacaga | 3660 |
| gtggctgctg cagaaactgc caagcatcag gccaaatgta acatctgcaa agagtgtcca | 3720 |
| atcattggat tcaggtacag gagtctaaag cactttaatt atgacatctg ccaaagctgc | 3780 |
| tttttttctg gtcgagttgc aaaaggccat aaaatgcact atcccatggt ggaatattgc | 3840 |
| actccgacta catcaggaga agatgttcga gactttgcca aggtactaaa aaacaaattt | 3900 |
| cgaaccaaaa ggtattttgc gaagcatccc cgaatgggct acctgccagt gcagactgtc | 3960 |
| ttagagggg acaacatgga aactcccgac acaatgtag | 3999 |

<210> SEQ ID NO 7
<211> LENGTH: 1667
<212> TYPE: DNA
<213> ORGANISM: Homo sapiens

<400> SEQUENCE: 7

| | |
|---|---|
| atgctttggt gggaagaagt agaggactgt tatgaaagag aagatgttca aaagaaaaca | 60 |
| ttcacaaaat gggtaaatgc acaattttct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata taatcctcca ctggcaggtc | 360 |
| aaaaatgtaa tgaaaaatat catggctgga ttgcaaccaa ccaacagtga aagattctc | 420 |
| ctgagctggg tccgacaatc aactcgtaat tatccacagg ttaatgtaat caacttcacc | 480 |
| accagctggt ctgatggcct ggctttgaat gctctcatcc atagtcatag gccagaccta | 540 |
| tttgactgga atagtgtggt ttgccagcag tcagccacac aacgactgga acatgcattc | 600 |
| aacatcgcca gatatcaatt aggcatagag aaactactcg atcctgaaga tgttgatacc | 660 |

-continued acctatccag ataagaagtc catcttaatg tacatcacat cactcttcca agttttgcct 720
caacaagtga gcattgaagc catccaggaa gtggaaatgt tgccaaggcc acctaaagtg 780
actaaagaag aacattttca gttacatcat caaatgcact attctcaaca gatcacggtc 840
agtctagcac agggatatga gagaacttct tcccctaagc ctcgattcaa gagctatgcc 900
tacacacagg ctgcttatgt caccacctct gaccctacac ggagcccatt tccttcacag 960
catttggaag ctcctgaaga caagtcattt ggcagttcat tgatggagag tgaagtaaac 1020
ctggaccgtt atcaaacagc tttagaagaa gtattatcgt ggcttctttc tgctgaggac 1080
acattgcaag cacaaggaga gatttctaat gatgtggaag tggtgaaaga ccagtttcat 1140
actcatgagg ggtacatgat ggatttgaca gcccatcagg gccgggttgg taatattcta 1200
caattgggaa gtaagctgat tggaacagga aaattatcag aagatgaaga aactgaagta 1260
caagagcaga tgaatctcct aaattcaaga tgggaatgcc tcagggtagc tagcatggaa 1320
aaacaaagca atttacatag agttttaatg gatctccaga atcagaaact gaaagagttg 1380
aatgactggc taacaaaaac agaagaaaga acaaggaaaa tggaggaaga gcctcttgga 1440
cctgatcttg aagacctaaa acgccaagta caacaacata aggtgcttca agaagatcta 1500
gaacaagaac aagtcagggt caattctctc actcacatgg tggtggtagt tgatgaatct 1560
agtggagatc acgcaactgc tgctttggaa gaacaactta aggtattggg agatcgatgg 1620
gcaaacatct gtagatggac agaagaccgc tgggttcttt tacaaga 1667


<210> SEQ ID NO 8
<211> LENGTH: 147
<212> TYPE: DNA
<213> ORGANISM: Homo sapiens

<400> SEQUENCE: 8
ggcaaagcag cctgacctag ctcctggact gaccactatt ggagcctctc ctactcagac 60
tgttactctg gtgacacaac ctgtggttac taaggaaact gccatctcca aactagaaat 120
gccatcttcc ttgatgttgg aggtacc 147


<210> SEQ ID NO 9
<211> LENGTH: 3858
<212> TYPE: DNA
<213> ORGANISM: Homo sapiens

<400> SEQUENCE: 9
attttcacca tggtttggtg ggaagaagta gaggactgtt atgaaagaga agatgttcaa 60
aagaaaacat tcacaaaatg ggtaaatgca caattttcta agtttgggaa gcagcatatt 120
gagaacctct tcagtgacct acaggatggg aggcgcctcc tagacctcct cgaaggcctg 180
acagggcaaa aactgccaaa agaaaaagga tccacaagag ttcatgccct gaacaatgtc 240
aacaaggcac tgcgggtttt gcagaacaat aatgttgatt tagtgaatat tggaagtact 300
gacatcgtag atggaaatca taaactgact cttggtttga tttggaatat aatcctccac 360
tggcaggtca aaaatgtaat gaaaaatatc atggctggat tgcaacaaac caacagtgaa 420
aagattctcc tgagctgggt ccgacaatca actcgtaatt atccacaggt taatgtaatc 480
aacttcacca ccagctggtc tgatggcctg gctttgaatg ctctcatcca tagtcatagg 540
ccagacctat ttgactggaa tagtgtggtt tgccagcagt cagccacaca acgactggaa 600
catgcattca acatcgccag atatcaatta ggcatagaga aactactcga tcctgaagat 660


```
gttgatacca cctatccaga taagaagtcc atcttaatgt acatcacatc actcttccaa      720
gttttgcctc aacaagtgag cattgaagcc atccaggaag tggaaatgtt gccaaggcca      780
cctaaagtga ctaaagaaga acattttcag ttacatcatc aaatgcacta ttctcaacag      840
atcacggtca gtctagcaca gggatatgag agaacttctt cccctaagcc tcgattcaag      900
agctatgcct acacacaggc tgcttatgtc accacctctg accctacacg gagcccattt      960
ccttcacagc atttggaagc tcctgaagac aagtcatttg gcagttcatt gatggagagt     1020
gaagtaaacc tggaccgtta tcaaacagct ttagaagaag tattatcgtg gcttctttct     1080
gctgaggaca cattgcaagc acaaggagag atttctaatg atgtggaagt ggtgaaagac     1140
cagtttcata ctcatgaggg gtacatgatg gatttgacag cccatcaggg ccgggttggt     1200
aatattctac aattgggaag taagctgatt ggaacaggaa aattatcaga agatgaagaa     1260
actgaagtac aagagcagat gaatctccta aattcaagat gggaatgcct cagggtagct     1320
agcatggaaa acaaagcaa tttacataga gttttaatgg atctccagaa tcagaaactg     1380
aaagagttga atgactggct aacaaaaaca gaagaaagaa caggaaaat ggaggaagag     1440
cctcttggac ctgatcttga agacctaaaa cgccaagtac aacaacataa ggtgcttcaa     1500
gaagatctag aacaagaaca agtcagggtc aattctctca ctcacatggt ggtggtagtt     1560
gatgaatcta gtggagatca cgcaactgct gctttggaag aacaacttaa ggtattggga     1620
gatcgatggg caaacatctg tagatggaca gaagaccgct gggttctttt acaagacact     1680
catagattac tgcaacagtt cccccctgac ctggaaaagt ttcttgcctg gcttacagaa     1740
gctgaaacaa ctgccaatgt cctacaggat gctacccgta aggaaaggct cctagaagac     1800
tccaagggag taaagagct gatgaaacaa tggcaagacc tccaaggtga aattgaagct     1860
cacacagatg tttatcacaa cctggatgaa acagccaaa aaatcctgag atccctggaa     1920
ggttccgatg atgcagtcct gttacaaaga cgttttggata acatgaactt caagtggagt     1980
gaacttcgga aaaagtctct caacattagg tcccatttgg aagccagttc tgaccagtgg     2040
aagcgtctgc acctttctct gcaggaactt ctggtgtggc tacagctgaa agatgatgaa     2100
ttaagccggc aggcacctat tggaggcgac tttccagcag ttcagaagca gaacgatgta     2160
catagggcct tcaagaggga attgaaaact aaagaacctg taatcatgag tactcttgag     2220
actgtacgaa tatttctgac agagcagcct ttggaaggac tagagaaact ctaccaggag     2280
cccagagagc tgcctcctga ggagagagcc cagaatgtca ctcggcttct acgaaagcag     2340
gctgaggagg tcaatactga gtgggaaaaa ttgaacctgc actccgctga ctggcagaga     2400
aaaatagatg agacccttga agactccag gaacttcaag aggccacgga tgagctggac     2460
ctcaagctgc gccaagctga ggtgatcaag ggatcctggc agcccgtggg cgatctcctc     2520
attgactctc tccaagatca cctcgagaaa gtcaaggcac ttcgaggaga aattgcgcct     2580
ctgaaagaga acgtgagcca cgtcaatgac cttgctcgcc agcttaccac tttgggcatt     2640
cagctctcac cgtataacct cagcactctg gaagacctga acaccagatg gaagcttctg     2700
caggtggccg tcgaggaccg agtcaggcag ctgcatgaag cccacaggga ctttggtcca     2760
gcatctcagc actttctttc cacgtctgtc cagggtccct gggagagagc catctcgcca     2820
aacaaagtgc cctactatat caaccacgag actcaaacaa cttgctggga ccatcccaaa     2880
atgacagagc tctaccagtc tttagctgac ctgaataatg tcagattctc agcttatagg     2940
actgccatga aactccgaag actgcagaag gccctttgct tggatctctt gagcctgtca     3000
```

-continued

```
gctgcatgtg atgccttgga ccagcacaac ctcaagcaaa atgaccagcc catggatatc    3060
ctgcagatta ttaattgttt gaccactatt tatgaccgcc tggagcaaga gcacaacaat    3120
ttggtcaacg tccctctctg cgtggatatg tgtctgaact ggctgctgaa tgtttatgat    3180
acgggacgaa cagggaggat ccgtgtcctg tcttttaaaa ctggcatcat ttccctgtgt    3240
aaagcacatt tggaagacaa gtacagatac cttttcaagc aagtggcaag ttcaacagga    3300
ttttgtgacc agcgcaggct gggcctcctt ctgcatgatt ctatccaaat tccaagacag    3360
ttgggtgaag ttgcatcctt tgggggcagt aacattgagc caagtgtccg gagctgcttc    3420
caatttgcta ataataagcc agagatcgaa gcggccctct tcctagactg gatgagactg    3480 gaacccagt ccatggtgtg gctgcccgtc ctgcacagag tggctgctgc agaaactgcc    3540
aagcatcagg ccaaatgtaa catctgcaaa gagtgtccaa tcattggatt caggtacagg    3600
agtctaaagc actttaatta tgacatctgc caaagctgct tttttctgg tcgagttgca    3660 aaaggccata aaatgcacta tcccatggtg gaatattgca ctccgactac atcaggagaa    3720
gatgttcgag actttgccaa ggtactaaaa aacaaatttc gaaccaaaag gtattttgcg    3780
aagcatcccc gaatgggcta cctgccagtg cagactgtct tagagggga caacatggaa    3840 actcccgaca caatgtag                                                   3858

<210> SEQ ID NO 10
<211> LENGTH: 3531
<212> TYPE: DNA
<213> ORGANISM: Homo sapiens

<400> SEQUENCE: 10
attttcacca tggtttggtg ggaagaagta gaggactgtt atgaaagaga agatgttcaa      60
aagaaaacat tcacaaaatg ggtaaatgca caatttttcta agtttgggaa gcagcatatt    120 gagaaccctct tcagtgacct acaggatggg aggcgcctcc tagacctcct cgaaggcctg    180
acagggcaaa aactgccaaa agaaaaagga tccacaagag ttcatgccct gaacaatgtc    240
aacaaggcac tgcgggtttt gcagaacaat aatgttgatt tagtgaatat tggaagtact    300
gacatcgtag atggaaatca taactgact cttggtttga tttggaatat aatcctccac    360
tggcaggtca aaaatgtaat gaaaatatc atggctggat tgcaacaaac caacagtgaa    420
aagattctcc tgagctgggt ccgacaatca actcgtaatt atccacaggt taatgtaatc    480
aacttcacca ccagctggtc tgatggcctg gctttgaatg ctctcatcca tagtcatagg    540
ccagacctat ttgactggaa tagtgtggtt tgccagcagt cagccacaca acgactggaa    600
catgcattca acatcgccag atatcaatta ggcatagaga aactactcga tcctgaagat    660
gttgatacca cctatccaga taagaagtcc atcttaatgt acatcacatc actcttccaa    720
gttttgcctc aacaagtgag cattgaagcc atccaggaag tggaaatgtt gccaaggcca    780
cctaaagtga ctaaagaaga acattttcag ttacatcatc aaatgcacta ttctcaacag    840
atcacggtca gtctagcaca gggatatgag agaacttctt cccctaagcc tcgattcaag    900
agctatgcct acacacaggc tgcttatgtc accacctctg accctacacg agcccattt    960 ccttcacagc atttggaagc tcctgaagac aagtcatttg gcagttcatt gatggagagt   1020
gaagtaaacc tggaccgtta tcaaacagct ttagaagaag tattatcgtg gcttctttct   1080
gctgaggaca cattgcaagc acaaggagag atttctaatg atgtggaagt ggtgaaagac   1140
cagtttcata ctcatgaggg gtacatgatg gatttgacag cccatcaggg ccgggttggt   1200
aatattctac aattgggaag taagctgatt ggaacaggaa aattatcaga agatgaagaa   1260
```

-continued

```
actgaagtac aagagcagat gaatctccta aattcaagat gggaatgcct cagggtagct    1320
agcatggaaa aacaaagcaa tttacataga actcatagat tactgcaaca gttcccctg    1380 gacctggaaa agtttcttgc ctggcttaca gaagctgaaa caactgccaa tgtcctacag    1440
gatgctaccc gtaaggaaag gctcctagaa gactccaagg gagtaaaaga gctgatgaaa    1500
caatggcaag acctccaagg tgaaattgaa gctcacacag atgtttatca caacctggat    1560
gaaaacagcc aaaaaatcct gagatccctg gaaggttccg atgatgcagt cctgttacaa    1620
agacgtttgg ataacatgaa cttcaagtgg agtgaacttc ggaaaaagtc tctcaacatt    1680
aggtcccatt tggaagccag ttctgaccag tggaagcgtc tgcacctttc tctgcaggaa    1740
cttctggtgt ggctacagct gaaagatgat gaattaagcc ggcaggcacc tattggaggc    1800
gactttccag cagttcagaa gcagaacgat gtacataggg ccttcaagag ggaattgaaa    1860
actaaagaac ctgtaatcat gagtactctt gagactgtac gaatatttct gacagagcag    1920
cctttggaag gactagagaa actctaccag gagcccagag agctgcctcc tgaggagaga    1980
gcccagaatg tcactcggct tctacgaaag caggctgagg aggtcaatac tgagtgggaa    2040
aaattgaacc tgcactccgc tgactggcag agaaaaatag atgagaccct tgaaagactc    2100
caggaacttc aagaggccac ggatgagctg gacctcaagc tgcgccaagc tgaggtgatc    2160
aagggatcct ggcagcccgt gggcgatctc ctcattgact ctctccaaga tcacctcgag    2220
aaagtcaagg cacttcgagg agaaattgcg cctctgaaag agaacgtgag ccacgtcaat    2280
gaccttgctc gccagcttac cactttgggc attcagctct caccgtataa cctcagcact    2340
ctggaagacc tgaacaccag atggaagctt ctgcaggtgg ccgtcgagga ccgagtcagg    2400
cagctgcatg aagcccacag ggactttggt ccagcatctc agcactttct ttccacgtct    2460
gtccagggtc cctgggagag agccatctcg ccaaacaaag tgccctacta tatcaaccac    2520
gagactcaaa caacttgctg ggaccatccc aaaatgacag agctctacca gtctttagct    2580
gacctgaata atgtcagatt ctcagcttat aggactgcca tgaaactccg aagactgcag    2640
aaggcccttt gcttggatct cttgagcctg tcagctgcat gtgatgcctt ggaccagcac    2700
aacctcaagc aaaatgacca gcccatggat atcctgcaga ttattaattg tttgaccact    2760
atttatgacc gcctggagca agagcacaac aatttggtca acgtccctct ctgcgtggat    2820
atgtgtctga actggctgct gaatgtttat gatacgggac gaacagggag gatccgtgtc    2880
ctgtctttta aaactggcat catttccctg tgtaaagcac atttggaaga caagtacaga    2940
taccttttca gcaagtggc aagttcaaca ggattttgtg accagcgcag gctgggcctc    3000
cttctgcatg attctatcca aattccaaga cagttgggtg aagttgcatc ctttgggggc    3060
agtaacattg agccaagtgt ccggagctgc ttccaatttg ctaataataa gccagagatc    3120
gaagcggccc tcttcctaga ctggatgaga ctggaacccc agtccatggt gtggctgccc    3180
gtcctgcaca gagtggctgc tgcagaaact gccaagcatc aggccaaatg taacatctgc    3240
aaagagtgtc caatcattgg attcaggtac aggagtctaa agcactttaa ttatgacatc    3300
tgccaaagct gcttttttc tggtcgagtt gcaaaaggcc ataaaatgca ctatcccatg    3360
gtggaatatt gcactccgac tacatcagga gaagatgttc gagactttgc caaggtacta    3420
aaaaacaaat ttcgaaccaa aaggtatttt gcgaagcatc cccgaatggg ctacctgcca    3480
gtgcagactg tcttagaggg ggacaacatg gaaactcccg acacaatgta g            3531
```

<210> SEQ ID NO 11

<211> LENGTH: 1340
<212> TYPE: DNA
<213> ORGANISM: Homo sapiens

<400> SEQUENCE: 11

| | | |
|---|---|---|
| atgctttggt gggaagaagt agaggactgt tatgaaagag aagatgttca aaagaaaaca | 60 |
| ttcacaaaat gggtaaatgc acaattttct aagtttggga agcagcatat tgagaacctc | 120 |
| ttcagtgacc tacaggatgg gaggcgcctc ctagacctcc tcgaaggcct gacagggcaa | 180 |
| aaactgccaa agaaaaagg atccacaaga gttcatgccc tgaacaatgt caacaaggca | 240 |
| ctgcgggttt tgcagaacaa taatgttgat ttagtgaata ttggaagtac tgacatcgta | 300 |
| gatggaaatc ataaactgac tcttggtttg atttggaata taatcctcca ctggcaggtc | 360 |
| aaaaatgtaa tgaaaatat catggctgga ttgcaaccaa ccaacagtga aaagattctc | 420 |
| ctgagctggg tccgacaatc aactcgtaat tatccacagg ttaatgtaat caacttcacc | 480 |
| accagctggt ctgatggcct ggctttgaat gctctcatcc atagtcatag gccagaccta | 540 |
| tttgactgga atagtgtggt tgccagcag tcagccacac aacgactgga acatgcattc | 600 |
| aacatcgcca gatatcaatt aggcatagag aaactactcg atcctgaaga tgttgatacc | 660 |
| acctatccag ataagaagtc catcttaatg tacatcacat cactcttcca gttttgcct | 720 |
| caacaagtga gcattgaagc catccaggaa gtggaaatgt tgccaaggcc acctaaagtg | 780 |
| actaagaag aacattttca gttacatcat caaatgcact attctcaaca gatcacggtc | 840 |
| agtctagcac agggatatga gagaacttct tcccctaagc ctcgattcaa gagctatgcc | 900 |
| tacacacagg ctgcttatgt caccacctct gaccctacac ggagcccatt tccttcacag | 960 |
| catttggaag ctcctgaaga caagtcattt ggcagttcat tgatggagag tgaagtaaac | 1020 |
| ctggaccgtt atcaaacagc tttagaagaa gtattatcgt ggcttctttc tgctgaggac | 1080 |
| acattgcaag cacaaggaga gatttctaat gatgtggaag tggtgaaaga ccagtttcat | 1140 |
| actcatgagg ggtacatgat ggatttgaca gcccatcagg gccgggttgg taatattcta | 1200 |
| caattgggaa gtaagctgat tggaacagga aaattatcag aagatgaaga aactgaagta | 1260 |
| caagagcaga tgaatctcct aaattcaaga tgggaatgcc tcagggtagc tagcatggaa | 1320 |
| aaacaaagca atttacatag | 1340 |

<210> SEQ ID NO 12
<211> LENGTH: 3510
<212> TYPE: DNA
<213> ORGANISM: Homo sapiens

<400> SEQUENCE: 12

| | | |
|---|---|---|
| attttcacca tggtttggtg ggaagaagta gaggactgtt atgaaagaga agatgttcaa | 60 |
| aagaaaacat tcacaaaatg ggtaaatgca caattttcta agtttgggaa gcagcatatt | 120 |
| gagaacctct tcagtgacct acaggatggg aggcgcctcc tagacctcct cgaaggcctg | 180 |
| acagggcaaa aactgccaaa agaaaaagga tccacaagag ttcatgccct gaacaatgtc | 240 |
| aacaaggcac tgcgggtttt gcagaacaat aatgttgatt tagtgaatat tggaagtact | 300 |
| gacatcgtag atggaaatca taaactgact cttggtttga tttggaatat aatcctccac | 360 |
| tggcaggtca aaaatgtaat gaaaatatc atggctggat tgcaacaaac caacagtgaa | 420 |
| aagattctcc tgagctgggt ccgacaatca actcgtaatt atccacaggt taatgtaatc | 480 |
| aacttcacca ccagctggtc tgatggcctg gctttgaatg ctctcatcca tagtcatagg | 540 |
| ccagacctat ttgactggaa tagtgtggtt gccagcagt cagccacaca acgactggaa | 600 |

-continued

```
catgcattca acatcgccag atatcaatta ggcatagaga aactactcga tcctgaagat    660
gttgatacca cctatccaga taagaagtcc atcttaatgt acatcacatc actcttccaa    720
gttttgcctc aacaagtgag cattgaagcc atccaggaag tggaaatgtt gccaaggcca    780
cctaaagtga ctaaagaaga acattttcag ttacatcatc aaatgcacta ttctcaacag    840
atcacggtca gtctagcaca gggatatgag agaacttctt cccctaagcc tcgattcaag    900
agctatgcct acacacaggc tgcttatgtc accacctctg accctacacg gagcccattt    960
ccttcacagc atttggaagc tcctgaagac aagtcatttg gcagttcatt gatggagagt    1020
gaagtaaacc tggaccgtta tcaaacagct ttagaagaag tattatcgtg gcttctttct    1080
gctgaggaca cattgcaagc acaaggagag atttctaatg atgtggaagt ggtgaaagac    1140
cagtttcata ctcatgaggg gtacatgatg gatttgacag cccatcaggg ccgggttggt    1200
aatattctac aattgggaag taagctgatt ggaacaggaa aattatcaga agatgaagaa    1260
actgaagtac aagagcagat gaatctccta aattcaagat gggaatgcct cagggtagct    1320
agcatggaaa aacaaagcaa tttacataga gttttaatgg atctccagaa tcagaaactg    1380
aaagagttga atgactggct aacaaaaaca gaagaaagaa caaggaaaat ggaggaagag    1440
cctcttggac ctgatcttga agacctaaaa cgccaagtac aacaacataa ggtgcttcaa    1500
gaagatctag aacaagaaca agtcagggtc aattctctca ctcacatggt ggtggtagtt    1560
gatgaatcta gtggagatca cgcaactgct gctttggaag aacaacttaa ggtattggga    1620
gatcgatggg caaacatctg tagatggaca gaagaccgct gggttctttt acaagacagt    1680
tctgaccagt ggaagcgtct gcacctttct ctgcaggaac ttctggtgtg gctacagctg    1740
aaagatgatg aattaagccg gcaggcacct attggaggcg actttccagc agttcagaag    1800
cagaacgatg tacatagggc cttcaagagg gaattgaaaa ctaaagaacc tgtaatcatg    1860
agtactcttg agactgtacg aatatttctg acagagcagc ctttggaagg actagagaaa    1920
ctctaccagg agcccagaga gctgcctcct gaggagagag cccagaatgt cactcggctt    1980
ctacgaaagc aggctgagga ggtcaatact gagtgggaaa aattgaacct gcactccgct    2040
gactggcaga gaaaaataga tgagacccttt gaaagactcc aggaacttca agaggccacg    2100
gatgagctgg acctcaagct cgccaagct gaggtgatca agggatcctg gcagcccgtg    2160
ggcgatctcc tcattgactc tctccaagat cacctcgaga aagtcaaggc acttcgagga    2220
gaaattgcgc ctctgaaaga aacgtgagc cacgtcaatg accttgctcg ccagcttacc    2280
actttgggca ttcagctctc accgtataac ctcagcactc tggaagacct gaacaccaga    2340
tggaagcttc tgcaggtggc cgtcgaggac cgagtcaggc agctgcatga agcccacagg    2400
gactttggtc cagcatctca gcactttctt tccacgtctg tccagggtcc ctgggagaga    2460
gccatctcgc caaacaaagt gccctactat atcaaccacg agactcaaac aacttgctgg    2520
gaccatccca aaatgacaga gctctaccag tctttagctg acctgaataa tgtcagattc    2580
tcagcttata ggactgccat gaaactccga agactgcaga aggcccttg cttggatctc    2640 ttgagcctgt cagctgcatg tgatgccttg gaccagcaca acctcaagca aaatgaccag    2700
cccatggata tcctgcagat tattaattgt ttgaccacta tttatgaccg cctggagcaa    2760
gagcacaaca atttggtcaa cgtccctctc tgcgtggata tgtgtctgaa ctggctgctg    2820
aatgtttatg atacgggacg aacagggagg atccgtgtcc tgtcttttaa aactggcatc    2880
atttccctgt gtaaagcaca tttggaagac aagtacagat accttttcaa gcaagtggca    2940
```

```
agttcaacag gattttgtga ccagcgcagg ctgggcctcc ttctgcatga ttctatccaa    3000
attccaagac agttgggtga agttgcatcc tttgggggca gtaacattga gccaagtgtc    3060
cggagctgct tccaatttgc taataataag ccagagatcg aagcggccct cttcctagac    3120
tggatgagac tggaacccca gtccatggtg tggctgcccg tcctgcacag agtggctgct    3180
gcagaaactg ccaagcatca ggccaaatgt aacatctgca aagagtgtcc aatcattgga    3240
ttcaggtaca ggagtctaaa gcactttaat tatgacatct gccaaagctg cttttttct     3300 ggtcgagttg caaaggcca taaaatgcac tatcccatgg tggaatattg cactccgact     3360
acatcaggag aagatgttcg agactttgcc aaggtactaa aaaacaaatt tcgaaccaaa    3420
aggtattttg cgaagcatcc ccgaatgggc tacctgccag tgcagactgt cttagagggg    3480
gacaacatgg aaactcccga cacaatgtag                                     3510

<210> SEQ ID NO 13
<211> LENGTH: 1821
<212> TYPE: DNA
<213> ORGANISM: Homo sapiens

<400> SEQUENCE: 13
cagttctgac cagtggaagc gtctgcacct ttctctgcag gaacttctgg tgtggctaca      60
gctgaaagat gatgaattaa gccggcaggc acctattgga ggcgactttc agcagttca     120 gaagcagaac gatgtacata gggccttcaa gagggaattg aaaactaaag aacctgtaat    180
catgagtact cttgagactg tacgaatatt tctgacagag cagcctttgg aaggactaga    240
gaaactctac caggagccca gagagctgcc tcctgaggag agagcccaga atgtcactcg    300
gcttctacga aagcaggctg aggaggtcaa tactgagtgg gaaaaattga acctgcactc    360
cgctgactgg cagagaaaaa tagatgagac ccttgaaaga ctccaggaac ttcaagaggc    420
cacggatgag ctggacctca gctgcgccaa agctgaggtg atcaagggat cctggcagcc    480
cgtgggcgat ctcctcattg actctctcca agatcacctc gagaaagtca aggcacttcg    540
aggagaaatt gcgcctctga agagaacgt gagccacgtc aatgaccttg ctcgccagct    600
taccactttg ggcattcagc tctcaccgta taacctcagc actctggaag acctgaacac    660
cagatggaag cttctgcagg tggccgtcga ggaccgagtc aggcagctgc atgaagccca    720
cagggacttt ggtccagcat ctcagcactt tctttccacg tctgtccagg gtccctggga    780
gagagccatc tcgccaaaca aagtgcccta ctatatcaac cacgagactc aaacaacttg    840
ctgggaccat cccaaaatga cagagctcta ccagtcttta gctgacctga ataatgtcag    900
attctcagct tataggactg ccatgaaact ccgaagactg cagaaggccc tttgcttgga    960
tctcttgagc ctgtcagctg catgtgatgc cttggaccag cacaacctca gcaaaatga    1020 ccagcccatg gatatcctgc agattattaa ttgtttgacc actatttatg accgcctgga   1080
gcaagagcac aacaatttgg tcaacgtccc tctctgcgtg gatatgtgtc tgaactggct   1140
gctgaatgtt tatgatacgg gacgaacagg aggatccgt gtcctgtctt ttaaaactgg    1200
catcatttcc ctgtgtaaag cacatttgga agacaagtac agataccttt tcaagcaagt   1260
ggcaagttca acaggatttt gtgaccagcg caggctgggc ctccttctgc atgattctat   1320
ccaaattcca agacagttgg gtgaagttgc atcctttggg ggcagtaaca ttgagccaag   1380
tgtccggagc tgcttccaat ttgctaataa taagccagag atcgaagcgg ccctcttcct   1440
agactggatg agactggaac cccagtccat ggtgtggctg cccgtcctgc acagagtggc   1500
tgctgcagaa actgccaagc atcaggccaa atgtaacatc tgcaaagagt gtccaatcat   1560
```

```
tggattcagg tacaggagtc taaagcactt taattatgac atctgccaaa gctgctttt      1620 ttctggtcga gttgcaaaag gccataaaat gcactatccc atggtggaat attgcactcc    1680
gactacatca ggagaagatg ttcgagactt tgccaaggta ctaaaaaaca aatttcgaac    1740
caaaaggtat tttgcgaagc atccccgaat gggctacctg ccagtgcaga ctgtcttaga   1800
gggggacaac atggaaactc c                                               1821

<210> SEQ ID NO 14
<211> LENGTH: 3446
<212> TYPE: DNA
<213> ORGANISM: Homo sapiens

<400> SEQUENCE: 14
attttcacca tggtttggtg ggaagaagta gaggactgtt atgaaagaga agatgttcaa      60
aagaaaacat tcacaaaatg ggtaaatgca caattttcta agtttgggaa gcagcatatt    120
gagaacctct tcagtgacct acaggatggg aggcgcctcc tagacctcct cgaaggcctg    180
acagggcaaa aactgccaaa agaaaaagga tccacaagag ttcatgccct gaacaatgtc    240
aacaaggcac tgcgggtttt gcagaacaat aatgttgatt tagtgaatat tggaagtact    300
gacatcgtag atgaaaatca taactgact cttggtttga tttggaatat aatcctccac     360
tggcaggtca aaaatgtaat gaaaaatatc atggctggat tgcaacaaac caacagtgaa    420 agattctcc tgagctgggt ccgacaatca actcgtaatt atccacaggt taatgtaatc     480
aacttcacca ccagctggtc tgatggcctg gctttgaatg ctctcatcca tagtcatagg   540
ccagacctat ttgactggaa tagtgtggtt tgccagcagt cagccacaca acgactggaa   600
catgcattca acatcgccag atatcaatta ggcatagaga aactactcga tcctgaagat   660
gttgatacca cctatccaga taagaagtcc atcttaatgt acatcacatc actcttccaa   720
gttttgcctc aacaagtgag cattgaagcc atccaggaag tggaaatgtt gccaaggcca   780
cctaaagtga ctaaagaaga acattttcag ttacatcatc aaatgcacta ttctcaacag   840
atcacggtca gtctagcaca gggatatgag agaacttctt ccctaagcc tcgattcaag    900 agctatgcct acacacaggc tgcttatgtc accacctctg accctacacg gagcccattt   960
ccttcacagc atttggaagc tcctgaagac aagtcatttg gcagttcatt gatggagagt  1020
gaagtaaacc tggaccgtta tcaaacagct ttagaagaag tattatcgtg gcttctttct  1080
gctgaggaca cattgcaagc acaaggagag atttctaatg atgtggaagt ggtgaaagac  1140
cagtttcata ctcatgaggg gtacatgatg gatttgacag cccatcaggg ccgggttggt  1200
aatattctac aattgggaag taagctgatt ggaacaggaa aattatcaga agatgaagaa  1260
actgaagtac aagagcagat gaatctccta aattcaagat gggaatgcct cagggtagct  1320
agcatggaaa acaaagcaa tttacataga gttttaatgg atctccagaa tcgaaactga   1380
aagagttgaa tgactggcta acaaaaacag aagaagaac aaggaaaatg gaggaagagc   1440
ctcttggacc tgatcttgaa gacctaaaac gccaagtaca caacataag gtgcttcaag   1500 aagatctaga acaagaacaa gtcagggtca attctctcac tcacatggtg gtggtagttg  1560
atgaatctag tggagatcac gcaactgctg ctttggaaga caacttaag gtattgggag   1620 atcgatgggc aaacatctgt agatggacag aagaccgctg ggttctttta caagacatcc  1680
ttctcaaatg gcaacgtctt actgaagaac agtgcctttt tagtgcatgg ctttcagaaa  1740
aagaagatgc agtgaacaag attcacacaa ctggctttaa agatcaaaat gaatgttat   1800
```

-continued

```
caagtcttca aaaactggcc gttttaaaag cggatctaga aaagaaaaag caatccatgg    1860
gcaaactgta ttcactcaaa caagatcttc tttcaacact gaagaataag tcagtgaccc    1920
agaagacgga agcatggctg ataactttg cccggtgttg ggataattta gtccaaaaac    1980
ttgaaaagag tacagcacag acccttgaaa gactccagga acttcaagag gccacggatg    2040
agctggacct caagctgcgc caagctgagg tgatcaaggg atcctggcag cccgtgggcg    2100
atctcctcat tgactctctc caagatcacc tcgagaaagt caaggcactt cgaggagaaa    2160
ttgcgcctct gaaagagaac gtgagccacg tcaatgacct tgctcgccag cttaccactt    2220
tgggcattca gctctcaccg tataacctca gcactctgga agacctgaac accagatgga    2280
agcttctgca ggtggccgtc gaggaccgag tcaggcagct gcatgaagcc cacagggact    2340
ttggtccagc atctcagcac tttctttcca cgtctgtcca gggtccctgg agagagccaa    2400
tctcgccaaa caaagtgccc tactatatca accacgagac tcaaacaact tgctgggacc    2460
atcccaaaat gacagagctc taccagtctt tagctgacct gaataatgtc agattctcag    2520
cttataggac tgccatgaaa ctccgaagac tgcagaaggc cctttgcttg gatctcttga    2580
gcctgtcagc tgcatgtgat gccttggacc agcacaacct caagcaaaat gaccagccca    2640
tggatatcct gcagattatt aattgtttga ccactattta tgaccgcctg gagcaagagc    2700
acaacaattt ggtcaacgtc cctctctgcg tggatatgtg tctgaactgg ctgctgaatg    2760
tttatgatac gggacgaaca gggaggatcc gtgtcctgtc ttttaaaact ggcatcattt    2820
ccctgtgtaa agcacatttg gaagacaagt acagatacct tttcaagcaa gtggcaagtt    2880
caacaggatt ttgtgaccag cgcaggctgg gcctccttct gcatgattct atccaaattc    2940
caagacagtt gggtgaagtt gcatcctttg ggggcagtaa cattgagcca agtgtccgga    3000
gctgcttcca atttgctaat aataagccag agatcgaagc ggccctcttc ctagactgga    3060
tgagactgga accccagtcc atggtgtggc tgcccgtcct gcacagagtg gctgctgcag    3120
aaactgccaa gcatcaggcc aaatgtaaca tctgcaaaga gtgtccaatc attggattca    3180
ggtacaggag tctaaagcac tttaattatg acatctgcca aagctgcttt ttttctggtc    3240
gagttgcaaa aggccataaa atgcactatc ccatggtgga atattgcact ccgactacat    3300
caggagaaga tgttcgagac tttgccaagg tactaaaaaa caaatttcga accaaaaggt    3360
attttgcgaa gcatccccga atgggctacc tgccagtgca gactgtctta gagggggaca    3420
acatggaaac tcccgacaca atgtag                                         3446
```

<210> SEQ ID NO 15
<211> LENGTH: 1434
<212> TYPE: DNA
<213> ORGANISM: Homo sapiens

<400> SEQUENCE: 15

```
gacccttgaa agactccagg aacttcaaga ggccacggat gagctggacc tcaagctgcg     60
ccaagctgag gtgatcaagg gatcctggca gcccgtgggc gatctcctca ttgactctct    120
ccaagatcac ctcgagaaag tcaaggcact tcgaggagaa attgcgcctc tgaaagagaa    180
cgtgagccac gtcaatgacc ttgctcgcca gcttaccact ttgggcattc agctctcacc    240
gtataacctc agcactctgg aagacctgaa caccagatgg aagcttctgc aggtggccgt    300
cgaggaccga gtcaggcagc tgcatgaagc ccacagggac tttggtccag catctcagca    360
ctttctttcc acgtctgtcc agggtccctg gagagagcca atctcgccaa acaaagtgcc    420
ctactatatc aaccacgaga ctcaaacaac ttgctgggac catcccaaaa tgacagagct    480
```

```
ctaccagtct ttagctgacc tgaataatgt cagattctca gcttatagga ctgccatgaa      540
actccgaaga ctgcagaagg ccctttgctt ggatctcttg agcctgtcag ctgcatgtga      600
tgccttggac cagcacaacc tcaagcaaaa tgaccagccc atggatatcc tgcagattat      660
taattgtttg accactattt atgaccgcct ggagcaagag cacaacaatt tggtcaacgt      720
ccctctctgc gtggatatgt gtctgaactg gctgctgaat gtttatgata cgggacgaac      780
agggaggatc cgtgtcctgt cttttaaaac tggcatcatt tccctgtgta aagcacattt      840
ggaagacaag tacagatacc ttttcaagca agtggcaagt tcaacaggat tttgtgacca      900
gcgcaggctg ggcctccttc tgcatgattc tatccaaatt ccaagacagt tgggtgaagt      960
tgcatccttt gggggcagta acattgagcc aagtgtccgg agctgcttcc aatttgctaa     1020
taataagcca gagatcgaag cggccctctt cctagactgg atgagactgg aaccccagtc     1080
catggtgtgg ctgcccgtcc tgcacagagt ggctgctgca gaaactgcca agcatcaggc     1140
caaatgtaac atctgcaaag agtgtccaat cattggattc aggtacagga gtctaaagca     1200
ctttaattat gacatctgcc aaagctgctt tttttctggt cgagttgcaa aaggccataa     1260
aatgcactat cccatggtgg aatattgcac tccgactaca tcaggagaag atgttcgaga     1320 cttttgccaag gtactaaaaa acaaatttcg aaccaaaagg tattttgcga agcatccccg     1380
aatgggctac ctgccagtgc agactgtctt agaggggac aacatggaaa ctcc             1434
```

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 16
attttcacca tggtttggtg ggaagaag                                          28

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17
cagcctgacc tagctcctgg actga                                             25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 18
actcatagat tactgcaaca gttcc                                             25

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
agttctgacc agtggaagcg                                                   20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 20
acccttgaaa gactccagga ac                                                22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
tctatgtaaa ttgctttgtt                                                   20

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 22
gtcttgtaaa agaacccagc ggtct                                             25

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 23
ctgtgctgta ctcttttcaa gtttt                                             25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 24
aggtacctcc aacatcaagg aagat                                             25

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 25
ctacattgtg tcgggagttt ccatgttgtc                                        30

<210> SEQ ID NO 26
<211> LENGTH: 955
<212> TYPE: DNA
<213> ORGANISM: Homo sapiens

```
<400> SEQUENCE: 26
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctagatc agcttgcatg cccactacgg gtctaggctg     180
cccatgtaag gaggcaaggc ctggggacac ccgagatgcc tggttataat taacccagac     240
atgtggctgc ccccccccc ccaacacctg ctgcctgagc ctcaccccca ccccggtgcc     300
tgggtcttag gctctgtaca ccatggagga gaagctcgct ctaaaaataa ccctgtccct     360
ggtggatccc ctgcatgccc aatcaaggct gtgggggact gagggcaggc tgtaacaggc     420
ttggggggcca gggcttatac gtgcctggga ctcccaaagt attactgttc catgttcccg     480
gcgaagggcc agctgtcccc cgccagctag actcagcact tagtttagga accagtgagc     540
aagtcagccc ttggggcagc ccatacaagg ccatggggct gggcaagctg cacgcctggg     600
tccggggtgg gcacggtgcc cgggcaacga gctgaaagct catctgctct caggggcccc     660
tccctgggga cagcccctcc tggctagtca cacctgtag gctcctctat ataacccagg     720
ggcacagggg ctgcccccgg gtcactcgag aggcctaata aagagctcag atgcatcgat     780
cagagtgtgt tggttttttg tgtgagatct aggaacccct agtgatggag ttggccactc     840
cctctctgcg cgctcgctcg ctcactgagg ccgcccgggc aaagcccggg cgtcgggcga     900
cctttggtcg cccggcctca gtgagcgagc gagcgcgcag agagggagtg gccaa          955

<210> SEQ ID NO 27
<211> LENGTH: 5149
<212> TYPE: DNA
<213> ORGANISM: Homo sapiens

<400> SEQUENCE: 27
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctagatc tgaattcgag cttgcatgcc cactacgggt     180
ctaggctgcc catgtaagga ggcaaggcct ggggacaccc gagatgcctg gttataatta     240
acccagacat gtggctgccc ccccccccc aacacctgct gcctgagcct caccccacc     300
ccggtgcctg ggtcttaggc tctgtacacc atggaggaga agctcgctct aaaaataacc     360
ctgtccctgg tggatcccct gcatgcccaa tcaaggctgt gggggactga gggcaggctg     420
taacaggctt gggggccagg gcttatacgt gcctggact cccaaagtat tactgttcca     480
tgttcccggc gaagggccag ctgtccccg ccagctagac tcagcactta gtttaggaac     540
cagtgagcaa gtcagccctt ggggcagccc atacaaggcc atgggctgg gcaagctgca     600
cgcctgggtc cggggtgggc acggtgcccg gcaacgagc tgaaagctca tctgctctca     660
ggggcccctc cctggggaca gcccctcctg gctagtcaca ccctgtaggc tcctctatat     720
aacccagggg cacaggggct gccccgggt cactcgaatt ttcaccatgg tttggtggga     780
agaagtagag gactgttatg aaagagaaga tgttcaaaag aaaacattca caaaatgggt     840
aaatgcacaa ttttctaagt ttgggaagca gcatattgag aacctcttca gtgacctaca     900
ggatgggagg cgcctcctag acctcctcga aggcctgaca gggcaaaaac tgccaaaaga     960
aaaaggatcc acaagagttc atgccctgaa caatgtcaac aaggcactgc gggttttgca    1020
gaacaataat gttgatttag tgaatattgg aagtactgac atcgtagatg gaaatcataa    1080
```

-continued

```
actgactctt ggtttgattt ggaatataat cctccactgg caggtcaaaa atgtaatgaa    1140
aaatatcatg gctggattgc aacaaaccaa cagtgaaaag attctcctga gctgggtccg    1200
acaatcaact cgtaattatc cacaggttaa tgtaatcaac ttcaccacca gctggtctga    1260
tggcctggct ttgaatgctc tcatccatag tcataggcca gacctatttg actggaatag    1320
tgtggtttgc cagcagtcag ccacacaacg actggaacat gcattcaaca tcgccagata    1380
tcaattaggc atagagaaac tactcgatcc tgaagatgtt gataccacct atccagataa    1440
gaagtccatc ttaatgtaca tcacatcact cttccaagtt ttgcctcaac aagtgagcat    1500
tgaagccatc caggaagtgg aaatgttgcc aaggccacct aaagtgacta agaagaaca    1560 ttttcagtta catcatcaaa tgcactattc tcaacagatc acggtcagtc tagcacaggg    1620
atatgagaga acttcttccc ctaagcctcg attcaagagc tatgcctaca cacaggctgc    1680
ttatgtcacc acctctgacc ctacacggag cccatttcct tcacagcatt tggaagctcc    1740
tgaagacaag tcatttggca gttcattgat ggagagtgaa gtaaacctgg accgttatca    1800
aacagcttta gaagaagtat tatcgtggct tctttctgct gaggacacat gcaagcaca    1860 aggagagatt tctaatgatg tggaagtggt gaaagaccag tttcatactc atgagggta    1920 catgatggat ttgacagccc atcagggccg ggttggtaat attctacaat gggaagtaa    1980 gctgattgga acaggaaaat tatcagaaga tgaagaaact gaagtacaag agcagatgaa    2040
tctcctaaat tcaagatggg aatgcctcag ggtagctagc atggaaaaac aaagcaattt    2100
acatagagtt ttaatggatc tccagaatca gaaactgaaa gagttgaatg actggctaac    2160
aaaaacagaa gaaagaacaa ggaaaatgga ggaagagcct cttggacctg atcttgaaga    2220
cctaaaacgc caagtacaac aacataaggt gcttcaagaa gatctagaac aagaacaagt    2280
cagggtcaat tctctcactc acatggtggt ggtagttgat gaatctagtg gagatcacgc    2340
aactgctgct ttggaagaac aacttaaggt attgggagat cgatgggcaa acatctgtag    2400
atggacagaa gaccgctggg ttcttttaca agacatcctt ctcaaatggc aacgtcttac    2460
tgaagaacag tgccttttta gtgcatggct ttcagaaaaa aagatgcag tgaacaagat    2520 tcacacaact ggctttaaag atcaaaatga aatgttatca agtcttcaaa aactggccgt    2580
tttaaaagcg gatctagaaa agaaaaagca atccatgggc aaactgtatt cactcaaaca    2640
agatcttctt tcaacactga gaataagtc agtgacccag aagacggaag catggctgga    2700
taactttgcc cggtgttggg ataatttagt ccaaaaactt gaaaagagta cagcacagac    2760
tcatagatta ctgcaacagt tccccctgga cctgaaaag tttcttgcct ggcttacaga    2820
agctgaaaca actgccaatg tcctacagga tgctacccgt aaggaaaggc tcctagaaga    2880
ctccaaggga gtaaaagagc tgatgaaaca atggcaagac ctccaaggtg aaattgaagc    2940
tcacacagat gtttatcaca acctggatga aaacagccaa aaaatcctga gatccctgga    3000
aggttccgat gatgcagtcc tgttacaag acgtttggat aacatgaact tcaagtggag    3060
tgaacttcgg aaaagtctc tcaacattag gtcccatttg aagccagtt ctgaccagtg    3120 gaagcgtctg cacctttctc tgcaggaact tctggtgtgg ctacagctga agatgatga    3180 attaagccgg caggcaccta ttggaggcga cttccagca gttcagaagc agaacgatgt    3240 acataggcc ttcaagaggg aattgaaaac taaagaacct gtaatcatga gtactcttga    3300
gactgtacga atatttctga cagagcagcc tttggaagga ctagagaaac tctaccagga    3360
gcccagagag ctgcctcctg aggagagagc ccagaatgtc actcggcttc tacgaaagca    3420
ggctgaggag gtcaatactg agtgggaaaa attgaacctg cactccgctg actggcagag    3480
```

-continued

```
aaaaatagat gagacccttg aaagactcca ggaacttcaa gaggccacgg atgagctgga    3540
cctcaagctg cgccaagctg aggtgatcaa gggatcctgg cagcccgtgg gcgatctcct    3600
cattgactct ctccaagatc acctcgagaa agtcaaggca cttcgaggag aaattgcgcc    3660
tctgaaagag aacgtgagcc acgtcaatga ccttgctcgc cagcttacca ctttgggcat    3720
tcagctctca ccgtataacc tcagcactct ggaagacctg aacaccagat ggaagcttct    3780
gcaggtggcc gtcgaggacc gagtcaggca gctgcatgaa gcccacaggg actttggtcc    3840
agcatctcag cactttcttt ccacgtctgt ccagggtccc tgggagagag ccatctcgcc    3900
aaacaaagtg ccctactata tcaaccacga gactcaaaca acttgctggg accatcccaa    3960
aatgacagag ctctaccagt ctttagctga cctgaataat gtcagattct cagcttatag    4020
gactgccatg aaactccgaa gactgcagaa ggccctttgc ttggatctct tgagcctgtc    4080
agctgcatgt gatgccttgg accagcacac cctcaagcaa aatgaccagc ccatggatat    4140
cctgcagatt attaattgtt tgaccactat ttatgaccgc ctggagcaag agcacaacaa    4200
tttggtcaac gtccctctct gcgtggatat gtgtctgaac tggctgctga atgtttatga    4260
tacgggacga acagggagga tccgtgtcct gtcttttaaa actggcatca tttccctgtg    4320
taaagcacat ttggaagaca agtacagata ccttttcaag caagtggcaa gttcaacagg    4380
attttgtgac cagcgcaggc tgggcctcct tctgcatgat tctatccaaa ttccaagaca    4440
gttgggtgaa gttgcatcct ttgggggcag taacattgag ccaagtgtcc ggagctgctt    4500
ccaatttgct aataataagc cagagatcga agcggccctc ttcctagact ggatgagact    4560
ggaaccccag tccatggtgt ggctgcccgt cctgcacaga gtggctgctg cagaaactgc    4620
caagcatcag gccaaatgta acatctgcaa agagtgtcca atcattggat tcaggtacag    4680
gagtctaaag cactttaatt atgacatctg ccaaagctgc ttttttttctg gtcgagttgc    4740
aaaaggccat aaaatgcact atcccatggt ggaatattgc actccgacta catcaggaga    4800
agatgttcga gactttgcca aggtactaaa aaacaaattt cgaaccaaaa ggtattttgc    4860
gaagcatccc cgaatgggct acctgccagt gcagactgtc ttagaggggg acaacatgga    4920
aactcccgac acaatgtagt cgagaggcct aataaagagc tcagatgcat cgatcagagt    4980
gtgttggttt tttgtgtgag atctaggaac ccctagtgat ggagttggcc actccctctc    5040
tgcgcgctcg ctcgctcact gaggccgccc gggcaaagcc cgggcgtcgg gcgacctttg    5100
gtcgcccggc tcagtgagc gagcgagcgc gcagagaggg agtggccaa               5149
```

<210> SEQ ID NO 28
<211> LENGTH: 4966
<212> TYPE: DNA
<213> ORGANISM: Homo sapiens

<400> SEQUENCE: 28

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg      120
gccaactcca tcactagggg ttcctagatc tgaattcgag cttgcatgcc cactacgggt     180
ctaggctgcc catgtaagga ggcaaggcct ggggacaccc gagatgcctg gttataatta     240
acccagacat gtggctgccc ccccccccc aacacctgct gcctgagcct cacccccacc     300
ccggtgcctg ggtcttaggc tctgtacacc atggaggaga agctcgctct aaaaataacc     360
ctgtccctgg tggatcccct gcatgcccaa tcaaggctgt gggggactga gggcaggctg    420
```

| | |
|---|---|
| taacaggctt gggggccagg gcttatacgt gcctgggact cccaaagtat tactgttcca | 480 |
| tgttcccggc gaagggccag ctgtcccccg ccagctagac tcagcactta gtttaggaac | 540 |
| cagtgagcaa gtcagccctt ggggcagccc atacaaggcc atggggctgg gcaagctgca | 600 |
| cgcctgggtc cggggtgggc acggtgcccg ggcaacgagc tgaaagctca tctgctctca | 660 |
| ggggcccctc cctggggaca gcccctcctg gctagtcaca ccctgtaggc tcctctatat | 720 |
| aacccagggg cacaggggct gccccgggt cactcgaatt ttcaccatgg tttggtggga | 780 |
| agaagtagag gactgttatg aaagagaaga tgttcaaaag aaaacattca caaaatgggt | 840 |
| aaatgcacaa ttttctaagt ttgggaagca gcatattgag aacctcttca gtgacctaca | 900 |
| ggatgggagg cgcctcctag acctcctcga aggcctgaca gggcaaaaac tgccaaaaga | 960 |
| aaaaggatcc acaagagttc atgccctgaa caatgtcaac aaggcactgc gggttttgca | 1020 |
| gaacaataat gttgatttag tgaatattgg aagtactgac atcgtagatg aaatcataa | 1080 |
| actgactctt ggtttgattt ggaatataat cctccactgg caggtcaaaa atgtaatgaa | 1140 |
| aaatatcatg gctggattgc aacaaaccaa cagtgaaaag attctcctga gctgggtccg | 1200 |
| acaatcaact cgtaattatc cacaggttaa tgtaatcaac ttcaccacca gctggtctga | 1260 |
| tggcctggct ttgaatgctc tcatccatag tcataggcca gacctatttg actggaatag | 1320 |
| tgtggtttgc cagcagtcag ccacacaacg actggaacat gcattcaaca tcgccagata | 1380 |
| tcaattaggc atagagaaac tactcgatcc tgaagatgtt gataccacct atccagataa | 1440 |
| gaagtccatc ttaatgtaca tcacatcact cttccaagtt ttgcctcaac aagtgagcat | 1500 |
| tgaagccatc caggaagtgg aaatgttgcc aaggccacct aaagtgacta agaagaaca | 1560 |
| ttttcagtta catcatcaaa tgcactattc tcaacagatc acggtcagtc tagcacaggg | 1620 |
| atatgagaga acttcttccc ctaagcctcg attcaagagc tatgcctaca cacaggctgc | 1680 |
| ttatgtcacc acctctgacc ctacacggag cccatttcct tcacagcatt tggaagctcc | 1740 |
| tgaagacaag tcatttggca gttcattgat ggagagtgaa gtaaacctgg accgttatca | 1800 |
| aacagcttta gaagaagtat tatcgtggct tctttctgct gaggacacat tgcaagcaca | 1860 |
| aggagagatt tctaatgatg tggaagtggt gaaagaccag tttcatactc atgagggta | 1920 |
| catgatggat ttgacagccc atcagggccg ggttggtaat attctacaat tgggaagtaa | 1980 |
| gctgattgga acaggaaaat tatcagaaga tgaagaaact gaagtacaag agcagatgaa | 2040 |
| tctcctaaat tcaagatggg aatgcctcag ggtagctagc atggaaaaac aaagcaattt | 2100 |
| acatagagtt ttaatggatc tccagaatca gaaactgaaa gagttgaatg actggctaac | 2160 |
| aaaaacagaa gaaagaacaa ggaaaatgga ggaagagcct cttggacctg atcttgaaga | 2220 |
| cctaaaacgc caagtacaac aacataaggt gcttcaagaa gatctagaac aagaacaagt | 2280 |
| cagggtcaat tctctcactc acatggtggt ggtagttgat gaatctagtg gagatcacgc | 2340 |
| aactgctgct ttgaagaac aacttaaggt attgggagat cgatgggcaa acatctgtag | 2400 |
| atggacagaa gaccgctggg ttctttaca agaccagcct gacctagctc ctggactgac | 2460 |
| cactattgga gcctctccta ctcagactgt tactctggtg acacaacctg tggttactaa | 2520 |
| ggaaactgcc atctccaaac tagaaatgcc atcttccttg atgttggagg tacctactca | 2580 |
| tagattactg caacagttcc ccctggacct ggaaaagttt cttgcctggc ttacagaagc | 2640 |
| tgaaacaact gccaatgtcc tacaggatgc tacccgtaag gaaaggctcc tagaagactc | 2700 |
| caagggagta aaagagctga tgaaacaatg gcaagacctc aaggtgaaa ttgaagctca | 2760 |
| cacagatgtt tatcacaacc tggatgaaaa cagccaaaaa atcctgagat ccctggaagg | 2820 |

-continued

```
ttccgatgat gcagtcctgt tacaaagacg tttggataac atgaacttca agtggagtga    2880
acttcggaaa aagtctctca acattaggtc ccatttggaa gccagttctg accagtggaa    2940
gcgtctgcac ctttctctgc aggaacttct ggtgtggcta cagctgaaag atgatgaatt    3000
aagccggcag gcacctattg gaggcgactt tccagcagtt cagaagcaga acgatgtaca    3060
tagggccttc aagagggaat tgaaaactaa agaacctgta atcatgagta ctcttgagac    3120
tgtacgaata tttctgacag agcagccttt ggaaggacta gagaaactct accaggagcc    3180
cagagagctg cctcctgagg agagagccca gaatgtcact cggcttctac gaaagcaggc    3240
tgaggaggtc aatactgagt gggaaaaatt gaacctgcac tccgctgact ggcagagaaa    3300
aatagatgag acccttgaaa gactccagga acttcaagag gccacggatg agctggacct    3360
caagctgcgc caagctgagg tgatcaaggg atcctggcag cccgtgggcg atctcctcat    3420
tgactctctc caagatcacc tcgagaaagt caaggcactt cgaggagaaa ttgcgcctct    3480
gaaagagaac gtgagccacg tcaatgacct tgctcgccag cttaccactt tgggcattca    3540
gctctcaccg tataacctca gcactctgga agacctgaac accagatgga agcttctgca    3600
ggtggccgtc gaggaccgag tcaggcagct gcatgaagcc cacagggact ttggtccagc    3660
atctcagcac tttctttcca cgtctgtcca gggtccctgg gagagagcca tctcgccaaa    3720
caaagtgccc tactatatca accacgagac tcaaacaact tgctgggacc atcccaaaat    3780
gacagagctc taccagtctt tagctgacct gaataatgtc agattctcag cttataggac    3840
tgccatgaaa ctccgaagac tgcagaaggc cctttgcttg gatctcttga gcctgtcagc    3900
tgcatgtgat gccttggacc agcacaacct caagcaaaat gaccagccca tggatatcct    3960
gcagattatt aattgtttga ccactattta tgaccgcctg gagcaagagc acaacaattt    4020
ggtcaacgtc cctctctgcg tggatatgtg tctgaactgg ctgctgaatg tttatgatac    4080
gggacgaaca gggaggatcc gtgtcctgtc ttttaaaact ggcatcattt ccctgtgtaa    4140
agcacatttg gaagacaagt acagatacct tttcaagcaa gtggcaagtt caacaggatt    4200 tgtgaccag cgcaggctgg gcctccttct gcatgattct atccaaattc caagacagtt    4260
gggtgaagtt gcatccttt ggggcagtaa cattgagcca agtgtccgga gctgcttcca    4320
atttgctaat aataagccag agatcgaagc ggccctcttc ctagactgga tgagactgga    4380
accccagtcc atggtgtggc tgcccgtcct gcacagagtg gctgctgcag aaactgccaa    4440
gcatcaggcc aaatgtaaca tctgcaaaga gtgtccaatc attggattca ggtacaggag    4500
tctaaagcac tttaattatg acatctgcca aagctgcttt ttttctggtc gagttgcaaa    4560
aggccataaa atgcactatc ccatggtgga atattgcact ccgactacat caggagaaga    4620
tgttcgagac tttgccaagg tactaaaaaa caaatttcga accaaaaggt attttgcgaa    4680
gcatccccga atgggctacc tgccagtgca gactgtctta gagggggaca acatggaaac    4740
tcccgacaca atgtagtcga gaggcctaat aaagagctca gatgcatcga tcagagtgtg    4800
ttggtttttt gtgtgagatc taggaacccc tagtgatgga gttggccact ccctctctgc    4860
gcgctcgctc gctcactgag gccgcccggg caaagcccgg gcgtcgggcg acctttggtc    4920
gcccggcctc agtgagcgag cgagcgcgca gagagggagt ggccaa            4966
```

<210> SEQ ID NO 29
<211> LENGTH: 4825
<212> TYPE: DNA
<213> ORGANISM: Homo sapiens

<400> SEQUENCE: 29

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctagatc tgaattcgag cttgcatgcc cactacgggt     180
ctaggctgcc catgtaagga ggcaaggcct ggggacaccc gagatgcctg gttataatta     240
acccagacat gtggctgccc ccccccccc aacacctgct gcctgagcct caccccacc      300
ccggtgcctg ggtcttaggc tctgtacacc atggaggaga agctcgctct aaaaataacc     360
ctgtccctgg tggatcccct gcatgcccaa tcaaggctgt gggggactga gggcaggctg     420
taacaggctt gggggccagg gcttatacgt gcctgggact cccaaagtat tactgttcca     480
tgttcccggc gaagggccag ctgtccccg ccagctagac tcagcactta gtttaggaac     540
cagtgagcaa gtcagccctt ggggcagccc atacaaggcc atgggctgg gcaagctgca     600
cgcctgggtc cggggtgggc acggtgcccg ggcaacgagc tgaaagctca tctgctctca     660
ggggcccctc cctggggaca gcccctcctg gctagtcaca ccctgtaggc tcctctatat     720
aacccagggg cacaggggct gccccgggt cactcgaatt ttcaccatgg tttggtggga     780
agaagtagag gactgttatg aaagagaaga tgttcaaaag aaaacattca caaaatgggt     840
aaatgcacaa ttttctaagt ttgggaagca gcatattgag aacctcttca gtgacctaca     900
ggatgggagg cgcctcctag acctcctcga aggcctgaca gggcaaaaac tgccaaaaga     960
aaaaggatcc acaagagttc atgccctgaa caatgtcaac aaggcactgc gggttttgca    1020
gaacaataat gttgatttag tgaatattgg aagtactgac atcgtagatg gaaatcataa    1080
actgactctt ggtttgattt ggaatataat cctccactgg caggtcaaaa atgtaatgaa    1140
aaatatcatg gctggattgc aacaaaccaa cagtgaaaag attctcctga ctgggtccg    1200
acaatcaact cgtaattatc cacaggttaa tgtaatcaac ttcaccacca gctggtctga    1260
tggcctggct ttgaatgctc tcatccatag tcataggcca gacctatttg actggaatag    1320
tgtggtttgc cagcagtcag ccacacaacg actggaacat gcattcaaca tcgccagata    1380
tcaattaggc atagagaaac tactcgatcc tgaagatgtt gataccacct atccagataa    1440
gaagtccatc ttaatgtaca tcacatcact cttccaagtt ttgcctcaac aagtgagcat    1500
tgaagccatc caggaagtgg aaatgttgcc aaggccacct aaagtgacta agaagaaca    1560
ttttcagtta catcatcaaa tgcactattc tcaacagatc acggtcagtc tagcacaggg    1620
atatgagaga acttcttccc ctaagcctcg attcaagagc tatgcctaca cacaggctgc    1680
ttatgtcacc acctctgacc ctacacggag cccatttcct tcacagcatt tggaagctcc    1740
tgaagacaag tcatttggca gttcattgat ggagagtgaa gtaaacctgg accgttatca    1800
aacagcttta gaagaagtat tatcgtggct tcttctgct gaggacacat gcaagcaca     1860
aggagagatt tctaatgatg tggaagtggt gaaagaccag tttcatactc atgagggta    1920
catgatggat ttgacagccc atcagggccg ggttggtaat attctacaat tgggaagtaa    1980
gctgattgga acaggaaaat tatcagaaga tgaagaaact gaagtacaag agcagatgaa    2040
tctcctaaat tcaagatggg aatgcctcag ggtagctagc atggaaaaac aaagcaattt    2100
acatagagtt ttaatggatc tccagaatca gaaactgaaa gagttgaatg actggctaac    2160
aaaaacagaa gaaagaacaa ggaaaatgga ggaagagcct cttggacctg atcttgaaga    2220
cctaaaacgc caagtacaac aacataaggt gcttcaagaa gatctagaac aagaacaagt    2280
cagggtcaat tctctcactc acatggtggt ggtagttgat gaatctagtg gagatcacgc    2340
```

```
aactgctgct tggaagaac aacttaaggt attgggagat cgatgggcaa acatctgtag      2400
atggacagaa gaccgctggg ttcttttaca agacactcat agattactgc aacagttccc      2460
cctggacctg gaaaagtttc ttgcctggct tacagaagct gaaacaactg ccaatgtcct      2520
acaggatgct acccgtaagg aaaggctcct agaagactcc aagggagtaa aagagctgat      2580
gaaacaatgg caagacctcc aagtgaaat tgaagctcac acagatgttt atcacaacct      2640
ggatgaaaac agccaaaaaa tcctgagatc cctggaaggt tccgatgatg cagtcctgtt      2700
acaaagacgt ttggataaca tgaacttcaa gtggagtgaa cttcggaaaa agtctctcaa      2760
cattaggtcc catttggaag ccagttctga ccagtggaag cgtctgcacc tttctctgca      2820
ggaacttctg gtgtggctac agctgaaaga tgatgaatta gccggcagg cacctattgg      2880 aggcgacttt ccagcagttc agaagcagaa cgatgtacat agggccttca agagggaatt      2940
gaaaactaaa gaacctgtaa tcatgagtac tcttgagact gtacgaatat ttctgacaga      3000
gcagcctttg gaaggactag agaaactcta ccaggagccc agagagctgc ctcctgagga      3060
gagagcccag aatgtcactc ggcttctacg aaagcaggct gaggaggtca atactgagtg      3120
ggaaaaattg aacctgcact ccgctgactg gcagagaaaa atagatgaga cccttgaaag      3180
actccaggaa cttcaagagg ccacggatga gctggacctc aagctgcgcc aagctgaggt      3240
gatcaaggga tcctggcagc ccgtgggcga tctcctcatt gactctctcc aagatcacct      3300
cgagaaagtc aaggcacttc gaggagaaat tgcgcctctg aaagagaacg tgagccacgt      3360
caatgacctt gctcgccagc ttaccacttt gggcattcag ctctcaccgt ataacctcag      3420
cactctggaa gacctgaaca ccagatggaa gcttctgcag gtggccgtcg aggaccgagt      3480
caggcagctc catgaagccc acagggactt tggtccagca tctcagcact ttctttccac      3540
gtctgtccag ggtccctggg agagagccat ctcgccaaac aaagtgccct actatatcaa      3600
ccacgagact caaacaactt gctgggacca tcccaaaatg acagagctct accagtcttt      3660
agctgacctg aataatgtca gattctcagc ttataggact gccatgaaaac tccgaagact      3720 gcagaaggcc ctttgcttgg atctcttgag cctgtcagct gcatgtgatg ccttggacca      3780
gcacaacctc aagcaaaatg accagcccat ggatatcctg cagattatta attgtttgac      3840
cactatttat gaccgcctgg agcaagagca caacaatttg gtcaacgtcc ctctctgcgt      3900
ggatatgtgt ctgaactggc tgctgaatgt ttatgatacg ggacgaacag ggaggatccg      3960
tgtcctgtct tttaaaactg gcatcatttc cctgtgtaaa gcacatttgg aagacaagta      4020
cagataccct ttcaagcaag tggcaagttc aacaggattt tgtgaccagc gcaggctggg      4080
cctccttctg catgattcta tccaaattcc aagacagttg ggtgaagttg catcctttgg      4140
gggcagtaac attgagccaa gtgtccggag ctgcttccaa tttgctaata ataagccaga      4200
gatcgaagcg gccctcttcc tagactggat gagactggaa ccccagtcca tggtgtggct      4260
gcccgtcctg cacagagtgg ctgctgcaga aactgccaag catcaggcca atgtaacat      4320 ctgcaaagag tgtccaatca ttggattcag gtacaggagt ctaaagcact ttaattatga      4380
catctgccaa agctgctttt tttctggtcg agttgcaaaa ggccataaaa tgcactatcc      4440
catggtggaa tattgcactc cgactacatc aggagaagat gttcgagact ttgccaaggt      4500
actaaaaaac aaatttcgaa ccaaaaggta ttttgcgaag catccccgaa tgggctacct      4560
gccagtgcag actgtcttag aggggacaa catggaaact cccgacacaa tgtagtcgag      4620
aggcctaata aagagctcag atgcatcgat cagagtgtgt tggtttttg tgtgagatct      4680
```

-continued

| | |
|---|---|
| aggaacccct agtgatggag ttggccactc cctctctgcg cgctcgctcg ctcactgagg | 4740 |
| ccgcccgggc aaagcccggg cgtcgggcga cctttggtcg cccggcctca gtgagcgagc | 4800 |
| gagcgcgcag agagggagtg gccaa | 4825 |

<210> SEQ ID NO 30
<211> LENGTH: 4498
<212> TYPE: DNA
<213> ORGANISM: Homo sapiens

<400> SEQUENCE: 30

| | |
|---|---|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctagatc tgaattcgag cttgcatgcc cactacgggt | 180 |
| ctaggctgcc catgtaagga ggcaaggcct ggggacaccc gagatgcctg gttataatta | 240 |
| acccagacat gtggctgccc cccccccccc aacacctgct gcctgagcct cacccccacc | 300 |
| ccggtgcctg ggtcttaggc tctgtacacc atggaggaga agctcgctct aaaaataacc | 360 |
| ctgtccctgg tggatcccct gcatgcccaa tcaaggctgt gggggactga gggcaggctg | 420 |
| taacaggctt gggggccagg gcttatacgt gcctgggact cccaaagtat tactgttcca | 480 |
| tgttcccggc gaagggccag ctgtcccccg ccagctagac tcagcactta gtttaggaac | 540 |
| cagtgagcaa gtcagcccct ggggcagccc atacaaggcc atgggctgg gcaagctgca | 600 |
| cgcctgggtc cggggtgggc acggtgcccg ggcaacgagc tgaaagctca tctgctctca | 660 |
| ggggcccctc cctggggaca gcccctcctg gctagtcaca ccctgtaggc tcctctatat | 720 |
| aacccagggg cacaggggct gccccgggt cactcgaatt ttcaccatgg tttggtggga | 780 |
| agaagtagag gactgttatg aaagagaaga tgttcaaaag aaaacattca caaaatgggt | 840 |
| aaatgcacaa ttttctaagt ttgggaagca gcatattgag aacctcttca gtgacctaca | 900 |
| ggatgggagg cgcctcctag acctcctcga aggcctgaca gggcaaaaac tgccaaaaga | 960 |
| aaaaggatcc acaagagttc atgccctgaa caatgtcaac aaggcactgc gggttttgca | 1020 |
| gaacaataat gttgatttag tgaatattgg aagtactgac atcgtagatg gaaatcataa | 1080 |
| actgactctt ggtttgattt ggaatataat cctccactgg caggtcaaaa atgtaatgaa | 1140 |
| aaatatcatg gctggattgc aacaaaccaa cagtgaaaag attctcctga gctgggtccg | 1200 |
| acaatcaact cgtaattatc acaggttaa tgtaatcaac ttcaccacca gctggtctga | 1260 |
| tggcctggct ttgaatgctc tcatccatag tcataggcca gacctatttg actggaatag | 1320 |
| tgtggtttgc cagcagtcag ccacacaacg actggaacat gcattcaaca tcgccagata | 1380 |
| tcaattaggc atagagaaac tactcgatcc tgaagatgtt gataccacct atccagataa | 1440 |
| gaagtccatc ttaatgtaca tcacatcact cttccaagtt ttgcctcaac aagtgagcat | 1500 |
| tgaagccatc caggaagtgg aaatgttgcc aaggccacct aaagtgacta agaagaaca | 1560 |
| ttttcagtta catcatcaaa tgcactattc tcaacagatc acggtcagtc tagcacaggg | 1620 |
| atatgagaga acttcttccc ctaagcctcg attcaagagc tatgcctaca cacaggctgc | 1680 |
| ttatgtcacc acctctgacc ctacacggag cccatttcct tcacagcatt ggaagctcc | 1740 |
| tgaagacaag tcatttggca gttcattgat ggagagtgaa gtaaacctgg accgttatca | 1800 |
| aacagcttta gaagaagtat tatcgtggct tctttctgct gaggacacat gcaagcaca | 1860 |
| aggagagatt tctaatgatg tggaagtggt gaaagaccag tttcatactc atgagggta | 1920 |
| catgatggat ttgacagccc atcagggccg ggttggtaat attctacaat gggaagtaa | 1980 |

-continued

```
gctgattgga acaggaaaat tatcagaaga tgaagaaact gaagtacaag agcagatgaa   2040
tctcctaaat tcaagatggg aatgcctcag ggtagctagc atggaaaaac aaagcaattt   2100
acatagaact catagattac tgcaacagtt ccccctggac ctggaaaagt ttcttgcctg   2160
gcttacagaa gctgaaacaa ctgccaatgt cctacaggat gctacccgta aggaaaggct   2220
cctagaagac tccaagggag taaaagagct gatgaaacaa tggcaagacc tccaaggtga   2280
aattgaagct cacacagatg tttatcacaa cctggatgaa aacagccaaa aaatcctgag   2340
atccctggaa ggttccgatg atgcagtcct gttacaaaga cgtttggata acatgaactt   2400
caagtggagt gaacttcgga aaaagtctct caacattagg tcccatttgg aagccagttc   2460
tgaccagtgg aagcgtctgc acctttctct gcaggaactt ctggtgtggc tacagctgaa   2520
agatgatgaa ttaagccggc aggcacctat tggaggcgac tttccagcag ttcagaagca   2580
gaacgatgta cataggcct tcaagaggga attgaaaact aaagaacctg taatcatgag    2640
tactcttgag actgtacgaa tatttctgac agagcagcct ttggaaggac tagagaaact   2700
ctaccaggag cccagagagc tgcctcctga ggagagagcc cagaatgtca ctcggcttct   2760
acgaaagcag gctgaggagg tcaatactga gtgggaaaaa ttgaacctgc actccgctga   2820
ctggcagaga aaaatagatg agacccttga aagactccag gaacttcaag aggccacgga   2880
tgagctggac ctcaagctgc gccaagctga ggtgatcaag ggatcctggc agcccgtggg   2940
cgatctcctc attgactctc tccaagatca cctcgagaaa gtcaaggcac ttcgaggaga   3000
aattgcgcct ctgaaagaga acgtgagcca cgtcaatgac cttgctcgcc agcttaccac   3060
tttgggcatt cagctctcac cgtataacct cagcactctg gaagacctga acaccagatg   3120
gaagcttctg caggtggccg tcgaggaccg agtcaggcag ctgcatgaag cccacaggga   3180
ctttggtcca gcatctcagc actttctttc cacgtctgtc cagggtccct gggagagagc   3240
catctcgcca aacaaagtgc cctactatat caaccacgag actcaaacaa cttgctggga   3300
ccatcccaaa atgacagagc tctaccagtc tttagctgac ctgaataatg tcagattctc   3360
agcttatagg actgccatga aactccgaag actgcagaag gccctttgct tggatctctt   3420
gagcctgtca gctgcatgtg atgccttgga ccagcacaac ctcaagcaaa atgaccagcc   3480
catggatatc ctgcagatta ttaattgttt gaccactatt tatgaccgcc tggagcaaga   3540
gcacaacaat ttggtcaacg tccctctctg cgtggatatg tgtctgaact ggctgctgaa   3600
tgtttatgat acgggacgaa cagggaggat ccgtgtcctg tcttttaaaa ctggcatcat   3660
ttccctgtgt aaagcacatt tggaagacaa gtacagatac ctttttcaagc aagtggcaag   3720 ttcaacagga ttttgtgacc agcgcaggct gggcctcctt ctgcatgatt ctatccaaat   3780
tccaagacag ttgggtgaag ttgcatcctt tgggggcagt aacattgagc caagtgtccg   3840
gagctgcttc caatttgcta ataataagcc agagatcgaa gcggccctct tcctagactg   3900
gatgagactg gaaccccagt ccatggtgtg gctgcccgtc ctgcacagag tggctgctgc   3960
agaaactgcc aagcatcagg ccaaatgtaa catctgcaaa gagtgtccaa tcattggatt   4020
caggtacagg agtctaaagc actttaatta tgacatctgc caaagctgct ttttttctgg   4080
tcgagttgca aaaggccata aaatgcacta tcccatggtg gaatattgca ctccgactac   4140
atcaggagaa gatgttcgag actttgccaa ggtactaaaa aacaaatttc gaaccaaaag   4200
gtattttgcg aagcatcccc gaatgggcta cctgccagtg cagactgtct tagaggggga   4260
caacatggaa actcccgaca caatgtagtc gagaggccta taaagagct cagatgcatc    4320
```

| | |
|---|---|
| gatcagagtg tgttggtttt ttgtgtgaga tctaggaacc cctagtgatg gagttggcca | 4380 |
| ctccctctct gcgcgctcgc tcgctcactg aggccgcccg ggcaaagccc gggcgtcggg | 4440 |
| cgacctttgg tcgcccggcc tcagtgagcg agcgagcgcg cagagaggga gtggccaa | 4498 |

<210> SEQ ID NO 31
<211> LENGTH: 4476
<212> TYPE: DNA
<213> ORGANISM: Homo sapiens

<400> SEQUENCE: 31

| | |
|---|---|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctagatc tgaattcgag cttgcatgcc cactacgggt | 180 |
| ctaggctgcc catgtaagga ggcaaggcct ggggacaccc gagatgcctg gttataatta | 240 |
| acccagacat gtggctgccc ccccccccc aacacctgct gcctgagcct cacccccacc | 300 |
| ccggtgcctg ggtcttaggc tctgtacacc atggaggaga agctcgctct aaaaataacc | 360 |
| ctgtccctgg tggatcccct gcatgcccaa tcaaggctgt gggggactga gggcaggctg | 420 |
| taacaggctt gggggccagg gcttatacgt gcctgggact cccaaagtat tactgttcca | 480 |
| tgttcccggc gaagggccag ctgtcccccg ccagctagac tcagcactta gtttaggaac | 540 |
| cagtgagcaa gtcagcccct ggggcagccc atacaaggcc atgggctgg gcaagctgca | 600 |
| cgcctgggtc cggggtgggc acggtgcccg ggcaacgagc tgaaagctca tctgctctca | 660 |
| ggggcccctc cctggggaca gcccctcctg gctagtcaca ccctgtggct cctctatata | 720 |
| acccaggggc acaggggctg ccccggggtc actcgaattt tcaccatggt ttggtgggaa | 780 |
| gaagtagagg actgttatga aagagaagat gttcaaaaga aaacattcac aaaatgggta | 840 |
| aatgcacaat tttctaagtt tgggaagcag catattgaga acctcttcag tgacctacag | 900 |
| gatgggaggc gcctcctaga cctcctcgaa ggcctgacag ggcaaaaact gccaaaagaa | 960 |
| aaaggatcca caagagttca tgccctgaac aatgtcaaca aggcactgcg ggttttgcag | 1020 |
| aacaataatg ttgatttagt gaatattgga agtactgaca tcgtagatgg aaatcataaa | 1080 |
| ctgactcttg gtttgatttg gaatataatc ctccactggc aggtcaaaaa tgtaatgaaa | 1140 |
| aatatcatgg ctggattgca acaaaccaac agtgaaaaga ttctcctgag ctgggtccga | 1200 |
| caatcaactc gtaattatcc acaggttaat gtaatcaact tcaccaccag ctggtctgat | 1260 |
| ggcctggctt tgaatgctct catccatagt cataggccag acctatttga ctggaatagt | 1320 |
| gtggtttgcc agcagtcagc cacacaacga ctgaacatg cattcaacat cgccagatat | 1380 |
| caattaggca tagagaaact actcgatcct gaagatgttg ataccaccta tccagataag | 1440 |
| aagtccatct taatgtacat cacatcactc ttccaagttt tgcctcaaca agtgagcatt | 1500 |
| gaagccatcc aggaagtgga aatgttgcca aggccaccta agtgactaa agaagaacat | 1560 |
| tttcagttac atcatcaaat gcactattct caacagatca cggtcagtct agcacaggga | 1620 |
| tatgagagaa cttcttcccc taagcctcga ttcaagagct atgcctacac acaggctgct | 1680 |
| tatgtcacca cctctgaccc tacacggagc ccatttcctt cacagcattt ggaagctcct | 1740 |
| gaagacaagt catttggcag ttcattgatg gagagtgaag taaacctgga ccgttatcaa | 1800 |
| acagctttag aagaagtatt atcgtggctt cttttctgctg aggacacatt gcaagcacaa | 1860 |
| ggagagattt ctaatgatgt ggaagtggtg aaagaccagt tcatactca tgagggggtac | 1920 |
| atgatggatt tgacagccca tcagggccgg gttggtaata ttctacaatt gggaagtaag | 1980 |

-continued

```
ctgattggaa caggaaaatt atcagaagat gaagaaactg aagtacaaga gcagatgaat    2040
ctcctaaatt caagatggga atgcctcagg gtagctagca tggaaaaaca aagcaattta    2100
catagagttt taatggatct ccagaatcag aaactgaaag agttgaatga ctggctaaca    2160
aaaacagaag aaagaacaag gaaaatggag aagagcctc ttggacctga tcttgaagac    2220
ctaaaacgcc aagtacaaca acataaggtg cttcaagaag atctagaaca agaacaagtc    2280
agggtcaatt ctctcactca catggtggtg gtagttgatg aatctagtgg agatcacgca    2340
actgctgctt tggaagaaca acttaaggta ttgggagatc gatgggcaaa catctgtaga    2400
tggacagaag accgctgggt tcttttacaa gacagttctg accagtggaa gcgtctgcac    2460
ctttctctgc aggaacttct ggtgtggcta cagctgaaag atgatgaatt aagccggcag    2520
gcacctattg gaggcgactt ccagcagtt cagaagcaga acgatgtaca tagggccttc    2580
aagagggaat tgaaaactaa agaacctgta atcatgagta ctcttgagac tgtacgaata    2640
tttctgacag agcagccttt ggaaggacta gagaaactct accaggagcc cagagagctg    2700
cctcctgagg agagagccca gaatgtcact cggcttctac gaaagcaggc tgaggaggtc    2760
aatactgagt gggaaaaatt gaacctgcac tccgctgact ggcagagaaa aatagatgag    2820
acccttgaaa gactccagga acttcaagag gccacggatg agctggacct caagctgcgc    2880
caagctgagg tgatcaaggg atcctggcag cccgtgggcg atctcctcat tgactctctc    2940
caagatcacc tcgagaaagt caaggcactt cgaggagaaa ttgcgcctct gaaagagaac    3000
gtgagccacg tcaatgacct tgctcgccag cttaccactt tgggcattca gctctcaccg    3060
tataacctca gcactctgga agacctgaac accagatgga agcttctgca ggtggccgtc    3120
gaggaccgag tcaggcagct gcatgaagcc cacagggact ttggtccagc atctcagcac    3180
tttctttcca cgtctgtcca gggtccctgg gagagagcca tctcgccaaa caaagtgccc    3240
tactatatca accacgagac tcaaacaact tgctgggacc atcccaaaat gacagagctc    3300
taccagtctt tagctgacct gaataatgtc agattctcag cttataggac tgccatgaaa    3360
ctccgaagac tgcagaaggc cctttgcttg gatctcttga gcctgtcagc tgcatgtgat    3420
gccttggacc agcacaacct caagcaaaat gaccagccca tggatatcct gcagattatt    3480
aattgtttga ccactattta tgaccgcctg gagcaagagc acaacaattt ggtcaacgtc    3540
cctctctgcg tggatatgtg tctgaactgg ctgctgaatg tttatgatac gggacgaaca    3600
gggaggatcc gtgtcctgtc ttttaaaact ggcatcattt ccctgtgtaa agcacatttg    3660
gaagacaagt acagatacct tttcaagcaa gtggcaagtt caacaggatt ttgtgaccag    3720
cgcaggctgg gcctccttct gcatgattct atccaaattc caagacagtt gggtgaagtt    3780
gcatcctttg ggggcagtaa cattgagcca agtgtccgga gctgcttcca atttgctaat    3840
aataagccag agatcgaagc ggccctcttc ctagactgga tgagactgga accccagtcc    3900
atggtgtggc tgcccgtcct gcacagagtg gctgctgcag aaactgccaa gcatcaggcc    3960
aaatgtaaca tctgcaaaga gtgtccaatc attggattca ggtacaggag tctaaagcac    4020
tttaattatg acatctgcca aagctgcttt ttttctggtc gagttgcaaa aggccataaa    4080
atgcactatc ccatggtgga atattgcact ccgactacat caggagaaga tgttcgagac    4140
tttgccaagg tactaaaaaa caaatttcga accaaaaggt attttgcgaa gcatcccga     4200 atgggctacc tgccagtgca gactgtctta gagggggaca acatggaaac tcccgacaca    4260
atgtagtcga gaggcctaat aaagagctca gatgcatcga tcagagtgtg ttggtttttt    4320
```

-continued

| | |
|---|---|
| gtgtgagatc taggaaccoc tagtgatgga gttggccact ccctctctgc gcgctcgctc | 4380 |
| gctcactgag gccgcccggg caaagcccgg gcgtcgggcg acctttggtc gcccggcctc | 4440 |
| agtgagcgag cgagcgcgca gagagggagt ggccaa | 4476 |

<210> SEQ ID NO 32
<211> LENGTH: 4414
<212> TYPE: DNA
<213> ORGANISM: Homo sapiens

<400> SEQUENCE: 32

| | |
|---|---|
| ttggccactc cctctctgcg cgctcgctcg ctcactgagg ccgggcgacc aaaggtcgcc | 60 |
| cgacgcccgg gctttgcccg ggcggcctca gtgagcgagc gagcgcgcag agagggagtg | 120 |
| gccaactcca tcactagggg ttcctagatc tgaattcgag cttgcatgcc cactacgggt | 180 |
| ctaggctgcc catgtaagga ggcaaggcct ggggacaccc gagatgcctg gttataatta | 240 |
| acccagacat gtggctgccc cccccccccc aacacctgct gcctgagcct caccccccacc | 300 |
| ccggtgcctg ggtcttaggc tctgtacacc atggaggaga agctcgctct aaaaataacc | 360 |
| ctgtccctgg tggatcccct gcatgcccaa tcaaggctgt gggggactga gggcaggctg | 420 |
| taacaggctt gggggccagg gcttatacgt gcctgggact cccaaagtat tactgttcca | 480 |
| tgttcccggc gaagggccag ctgtcccccg ccagctagac tcagcactta gtttaggaac | 540 |
| cagtgagcaa gtcagcccett ggggcagccc atacaaggcc atgggctgg gcaagctgca | 600 |
| cgcctgggtc cggggtgggc acggtgcccg ggcaacgagc tgaaagctca tctgctctca | 660 |
| ggggccctc cctggggaca gccctcctg gctagtcaca ccctgtaggc tcctctatat | 720 |
| aacccagggg cacaggggct gccccgggt cactcgaatt ttcaccatgg tttggtggga | 780 |
| agaagtagag gactgttatg aaagagaaga tgttcaaaag aaaacattca caaaatgggt | 840 |
| aaatgcacaa ttttctaagt ttgggaagca gcatattgag aacctcttca gtgacctaca | 900 |
| ggatgggagg cgcctcctag acctcctcga aggcctgaca gggcaaaaac tgccaaaaga | 960 |
| aaaaggatcc acaagagttc atgccctgaa caatgtcaac aaggcactgc gggttttgca | 1020 |
| gaacaataat gttgatttag tgaatattgg aagtactgac atcgtagatg gaaatcataa | 1080 |
| actgactctt ggtttgattt ggaatataat cctccactgg caggtcaaaa atgtaatgaa | 1140 |
| aaatatcatg gctggattgc aacaaaccaa cagtgaaaag attctcctga gctgggtccg | 1200 |
| acaatcaact cgtaattatc cacaggttaa tgtaatcaac ttcaccacca gctggtctga | 1260 |
| tggcctggct ttgaatgctc tcatccatag tcataggcca gacctatttg actggaatag | 1320 |
| tgtggtttgc cagcagtcag ccacacaacg actggaacat gcattcaaca tcgccagata | 1380 |
| tcaattaggc atagagaaac tactcgatcc tgaagatgtt gataccacct atccagataa | 1440 |
| gaagtccatc ttaatgtaca tcacatcact cttccaagtt ttgcctcaac aagtgagcat | 1500 |
| tgaagccatc caggaagtgg aaatgttgcc aaggccacct aaagtgacta agaagaaca | 1560 |
| ttttcagtta catcatcaaa tgcactattc tcaacagatc acggtcagtc tagcacaggg | 1620 |
| atatgagaga acttcttccc ctaagcctcg attcaagagc tatgcctaca cacaggctgc | 1680 |
| ttatgtcacc acctctgacc ctacacggag cccatttcct tcacagcatt ggaagctcc | 1740 |
| tgaagacaag tcatttggca gttcattgat ggagagtgaa gtaaacctgg accgttatca | 1800 |
| aacagcttta gaagaagtat tatcgtggct tctttctgct gaggacacat gcaagcaca | 1860 |
| aggagagatt tctaatgatg tggaagtggt gaaagaccag tttcatactc atgagggta | 1920 |
| catgatggat ttgacagccc atcagggccg ggttggtaat attctacaat gggaagtaa | 1980 |

```
gctgattgga acaggaaaat tatcagaaga tgaagaaact gaagtacaag agcagatgaa    2040
tctcctaaat tcaagatggg aatgcctcag ggtagctagc atggaaaaac aaagcaattt    2100
acatagagtt ttaatggatc tccagaatca gaaactgaaa gagttgaatg actggctaac    2160
aaaaacagaa gaaagaacaa ggaaaatgga ggaagagcct cttggacctg atcttgaaga    2220
cctaaaacgc caagtacaac aacataaggt gcttcaagaa gatctagaac aagaacaagt    2280
cagggtcaat tctctcactc acatggtggt ggtagttgat gaatctagtg gagatcacgc    2340
aactgctgct ttggaagaac aacttaaggt attgggagat cgatgggcaa acatctgtag    2400
atggacagaa gaccgctggg ttcttttaca agacatcctt ctcaaatggc aacgtcttac    2460
tgaagaacag tgcctttttta gtgcatggct ttcagaaaaa gaagatgcag tgaacaagat    2520
tcacacaact ggctttaaag atcaaaatga aatgttatca agtcttcaaa aactggccgt    2580
tttaaaagcg gatctagaaa agaaaaagca atccatgggc aaactgtatt cactcaaaca    2640
agatcttctt tcaacactga agaataagtc agtgacccag aagacggaag catggctgga    2700
taactttgcc cggtgttggg ataatttagt ccaaaaactt gaaaagagta cagcacagac    2760
ccttgaaaga ctccaggaac ttcaagaggc cacggatgag ctggacctca gctgcgcca    2820 agctgaggtg atcaagggat cctggcagcc cgtgggcgat ctcctcattg actctctcca    2880
agatcacctc gagaaagtca aggcacttcg aggagaaatt gcgcctctga agagaacgt    2940 gagccacgtc aatgaccttg ctcgccagct taccactttg ggcattcagc tctcaccgta    3000
taacctcagc actctggaag acctgaacac cagatgaag cttctgcagg tggccgtcga    3060
ggaccgagtc aggcagctgc atgaagccca cagggacttt ggtccagcat ctcagcactt    3120
tctttccacg tctgtccagg gtccctggga gagccatc tcgccaaaca aagtgcccta    3180
ctatatcaac cacgagactc aaacaacttg ctgggaccat cccaaaatga cagagctcta    3240
ccagtcttta gctgacctga ataatgtcag attctcagct tataggactg ccatgaaact    3300
ccgaagactg cagaaggccc tttgcttgga tctcttgagc ctgtcagctg catgtgatgc    3360
cttggaccag cacaacctca agcaaaatga ccagcccatg gatatcctgc agattattaa    3420
ttgtttgacc actatttatg accgcctgga gcaagagcac aacaatttgg tcaacgtccc    3480
tctctgcgtg gatatgtgtc tgaactggct gctgaatgtt tatgatacgg gacgaacagg    3540
gaggatccgt gtcctgtctt ttaaaactgg catcatttcc ctgtgtaaag cacatttgga    3600
agacaagtac agataccttt tcaagcaagt ggcaagttca acaggatttt gtgaccagcg    3660
caggctgggc ctccttctgc atgattctat ccaaattcca agacagttgg gtgaagttgc    3720
atcctttggg ggcagtaaca ttgagccaag tgtccggagc tgcttccaat ttgctaataa    3780
taagccagag atcgaagcgg ccctcttcct agactggatg agactggaac cccagtccat    3840
ggtgtggctg cccgtcctgc acagagtggc tgctgcagaa actgccaagc atcaggccaa    3900
atgtaacatc tgcaaagagt gtccaatcat tggattcagg tacaggagtc taaagcactt    3960
taattatgac atctgccaaa gctgcttttt ttctggtcga gttgcaaaag gccataaaat    4020
gcactatccc atggtggaat attgcactcc gactacatca ggagaagatg ttcgagactt    4080
tgccaaggta ctaaaaaaca aatttcgaac caaaaggtat tttgcgaagc atccccgaat    4140
gggctaccct ccagtgcaga ctgtcttaga gggggacaac atggaaactc ccgacacaat    4200
gtagtcgaga ggcctaataa agagctcaga tgcatcgatc agagtgtgtt ggtttttttgt    4260 gtgagatcta ggaacccctta gtgatggagt tggccactcc ctctctgcgc gctcgctcgc    4320
```

```
tcactgaggc cgcccgggca aagcccgggc gtcgggcgac ctttggtcgc ccggcctcag    4380
tgagcgagcg agcgcgcaga gagggagtgg ccaa                                4414
```

<210> SEQ ID NO 33
<211> LENGTH: 987
<212> TYPE: DNA
<213> ORGANISM: Homo sapiens

<400> SEQUENCE: 33

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcctagatc tgaattcggt acccgttaca taacttacgg    180
taaatggccc gcctggctga ccgcccaacg accccgcc attgacgtca ataatgacgt    240
atgttcccat agtaacgcca atagggactt tccattgacg tcaatgggtg gagtatttac    300
ggtaaactgc ccacttggca gtacatcaag tgtatcatat gccaagtacg cccctattg    360 acgtcaatga cggtaaatgg cccgcctggc attatgcca gtacatgacc ttatgggact    420
ttcctacttg gcagtacatc tacgtattag tcatcgctat taccatggtg atgcggtttt    480
ggcagtacat caatgggcgt ggatagcggt ttgactcacg gggatttcca agtctccacc    540
ccattgacgt caatgggagt ttgtttttggc accaaaatca acgggacttt ccaaaatgtc    600
gtaacaactc cgccccattg acgcaaatgg gcggtaggcg tgtacggtgg gaggtctata    660
taagcagagc tcgtttagtg aaccgtcaga tcgcctggag acgccatcca cgctgttttg    720
acctccatag aagacaccgg gaccgatcca gcctccggac tctagaggat ccggtactcg    780
agaggcctaa taaagagctc agatgcatcg atcagagtgt gttggttttt tgtgtgagat    840
ctaggaaccc ctagtgatgg agttggccac tccctctctg cgcgctcgct cgctcactga    900
ggccgcccgg gcaaagcccg ggcgtcgggc gacctttggt cgcccggcct cagtgagcga    960
gcgagcgcgc agagagggag tggccaa                                        987
```

<210> SEQ ID NO 34
<211> LENGTH: 4990
<212> TYPE: DNA
<213> ORGANISM: Homo sapiens

<400> SEQUENCE: 34

```
ttggccactc cctctctgcg cgctcgctcg ctcactgagg ccgggcgacc aaaggtcgcc     60
cgacgcccgg gctttgcccg gcggcctca gtgagcgagc gagcgcgcag agagggagtg    120
gccaactcca tcactagggg ttcctagatc tgaattcggt acccgttaca taacttacgg    180
taaatggccc gcctggctga ccgcccaacg accccgcc attgacgtca ataatgacgt    240
atgttcccat agtaacgcca atagggactt tccattgacg tcaatgggtg gagtatttac    300
ggtaaactgc ccacttggca gtacatcaag tgtatcatat gccaagtacg cccctattg    360 acgtcaatga cggtaaatgg cccgcctggc attatgcca gtacatgacc ttatgggact    420
ttcctacttg gcagtacatc tacgtattag tcatcgctat taccatggtg atgcggtttt    480
ggcagtacat caatgggcgt ggatagcggt ttgactcacg gggatttcca agtctccacc    540
ccattgacgt caatgggagt ttgtttttggc accaaaatca acgggacttt ccaaaatgtc    600
gtaacaactc cgccccattg acgcaaatgg gcggtaggcg tgtacggtgg gaggtctata    660
taagcagagc tcgtttagtg aaccgtcaga tcgcctggag acgccatcca cgctgttttg    720
acctccatag aagacaccgg gaccgatcca gcctccggac tctagaggat ccggtactcg    780
```

```
aattttcacc atggtttggt gggaagaagt agaggactgt tatgaaagag aagatgttca    840
aaagaaaaca ttcacaaaat gggtaaatgc acaattttct aagtttggga agcagcatat    900
tgagaacctc ttcagtgacc tacaggatgg gaggcgcctc ctagacctcc tcgaaggcct    960
gacagggcaa aaactgccaa agaaaaagg atccacaaga gttcatgccc tgaacaatgt    1020
caacaaggca ctgcgggttt tgcagaacaa taatgttgat ttagtgaata ttggaagtac    1080
tgacatcgta gatggaaatc ataaactgac tcttggtttg atttggaata taatcctcca    1140
ctggcaggtc aaaaatgtaa tgaaaaatat catggctgga ttgcaacaaa ccaacagtga    1200
aaagattctc ctgagctggg tccgacaatc aactcgtaat tatccacagg ttaatgtaat    1260
caacttcacc accagctggt ctgatggcct ggctttgaat gctctcatcc atagtcatag    1320
gccagaccta tttgactgga atagtgtggt ttgccagcag tcagccacac aacgactgga    1380
acatgcattc aacatcgcca gatatcaatt aggcatagag aaactactcg atcctgaaga    1440
tgttgatacc acctatccag ataagaagtc catcttaatg tacatcacat cactcttcca    1500
agttttgcct caacaagtga gcattgaagc catccaggaa gtggaaatgt tgccaaggcc    1560
acctaaagtg actaaagaag aacattttca gttacatcat caaatgcact attctcaaca    1620
gatcacggtc agtctagcac agggatatga gagaacttct tcccctaagc ctcgattcaa    1680
gagctatgcc tacacacagg ctgcttatgt caccacctct gaccctacac ggagcccatt    1740
tccttcacag catttggaag ctcctgaaga caagtcattt ggcagttcat tgatggagag    1800
tgaagtaaac ctggaccgtt atcaaacagc tttagaagaa gtattatcgt ggcttctttc    1860
tgctgaggac acattgcaag cacaaggaga gatttctaat gatgtggaag tggtgaaaga    1920
ccagtttcat actcatgagg ggtacatgat ggatttgaca gcccatcagg gccgggttgg    1980
taatattcta caattgggaa gtaagctgat tggaacagga aaattatcag aagatgaaga    2040
aactgaagta caagagcaga tgaatctcct aaattcaaga tgggaatgcc tcagggtagc    2100
tagcatggaa aaacaaagca atttacatag agttttaatg gatctccaga atcagaaact    2160
gaaagagttg aatgactggc taacaaaaac agaagaaaga acaaggaaaa tggaggaaga    2220
gcctcttgga cctgatcttg aagacctaaa acgccaagta caacaacata aggtgcttca    2280
agaagatcta gaacaagaac aagtcagggt caattctctc actcacatgg tggtggtagt    2340
tgatgaatct agtggagatc acgcaactgc tgctttggaa gaacaactta aggtattggg    2400
agatcgatgg gcaaacatct gtagatggac agaagaccgc tgggttcttt tacaagacca    2460
gcctgaccta gctcctggac tgaccactat tggagcctct cctactcaga ctgttactct    2520
ggtgacacaa cctgtggtta ctaaggaaac tgccatctcc aaactagaaa tgccatcttc    2580
cttgatgttg gaggtaccta ctcatagatt actgcaacag ttcccctggg acctggaaaa    2640
gtttcttgcc tggcttacag aagctgaaac aactgccaat gtcctacagg atgctacccg    2700
taaggaaagg ctcctagaag actccaaggg agtaaaagag ctgatgaaac aatggcaaga    2760
cctccaaggt gaaattgaag ctcacacaga tgtttatcac aacctggatg aaaacagcca    2820
aaaaatcctg agatccctgg aaggttccga tgatgcagtc ctgttacaaa gacgtttgga    2880
taacatgaac ttcaagtgga gtgaacttcg gaaaaagtct ctcaacatta ggtcccattt    2940
ggaagccagt tctgaccagt ggaagcgtct gcaccttcct ctgcaggaac ttctggtgtg    3000
gctacagctg aaagatgatg aattaagccg gcaggcacct attggaggcg actttccagc    3060
agttcagaag cagaacgatg tacatagggc cttcaagagg gaattgaaaa ctaaagaacc    3120
```

-continued

```
tgtaatcatg agtactcttg agactgtacg aatatttctg acagagcagc ctttggaagg      3180
actagagaaa ctctaccagg agcccagaga gctgcctcct gaggagagag cccagaatgt      3240
cactcggctt ctacgaaagc aggctgagga ggtcaatact gagtgggaaa aattgaacct      3300
gcactccgct gactggcaga gaaaaataga tgagacccct gaaagactcc aggaacttca      3360
agaggccacg gatgagctgg acctcaagct gcgccaagct gaggtgatca agggatcctg      3420
gcagcccgtg ggcgatctcc tcattgactc tctccaagat cacctcgaga aagtcaaggc      3480
acttcgagga gaaattgcgc ctctgaaaga gaacgtgagc cacgtcaatg accttgctcg      3540
ccagcttacc actttgggca ttcagctctc accgtataac ctcagcactc tggaagacct      3600
gaacaccaga tggaagcttc tgcaggtggc cgtcgaggac cgagtcaggc agctgcatga      3660
agcccacagg gactttggtc cagcatctca gcactttctt tccacgtctg tccagggtcc      3720
ctgggagaga gccatctcgc caaacaaagt gccctactat atcaaccacg agactcaaac      3780
aacttgctgg gaccatccca aaatgacaga gctctaccag tctttagctg acctgaataa      3840
tgtcagattc tcagcttata ggactgccat gaaactccga agactgcaga aggcccttg      3900 cttggatctc ttgagcctgt cagctgcatg tgatgccttg gaccagcaca acctcaagca      3960
aaatgaccag cccatggata tcctgcagat tattaattgt ttgaccacta tttatgaccg      4020
cctggagcaa gagcacaaca atttggtcaa cgtccctctc tgcgtggata tgtgtctgaa      4080
ctggctgctg aatgtttatg atacgggacg aacagggagg atccgtgtcc tgtcttttaa      4140
aactggcatc atttccctgt gtaaagcaca tttggaagac aagtacagat acctttcaa      4200 gcaagtggca agttcaacag gattttgtga ccagcgcagg ctgggcctcc ttctgcatga      4260
ttctatccaa attccaagac agttgggtga agttgcatcc tttgggggca gtaacattga      4320
gccaagtgtc cggagctgct tccaatttgc taataataag ccagagatcg aagcggccct      4380
cttcctagac tggatgagac tggaacccca gtccatggtg tggctgcccg tcctgcacag      4440
agtggctgct gcagaaactg ccaagcatca ggccaaatgt aacatctgca aagagtgtcc      4500
aatcattgga ttcaggtaca ggagtctaaa gcactttaat tatgacatct gccaaagctg      4560 cttttttttct ggtcgagttg caaaaggcca taaaatgcac tatcccatgg tggaatattg      4620
cactccgact acatcaggag aagatgttcg agactttgcc aagtactaa aaaacaaatt      4680 tcgaaccaaa aggtatttg cgaagcatcc ccgaatgggc tacctgccag tgcagactgt      4740
cttagagggg gacaacatgg aaactcccga cacaatgtag tcgagaggcc taataaagag      4800
ctcagatgca tcgatcagag tgtgttggtt ttttgtgtga gatctaggaa ccctagtga      4860 tggagttggc cactccctct ctgcgcgctc gctcgctcac tgaggccgcc gggcaaagc      4920 ccgggcgtcg ggcgaccttt ggtcgcccgg cctcagtgag cgagcgagcg cgcagagagg      4980
gagtggccaa                                                            4990
```

<210> SEQ ID NO 35
<211> LENGTH: 4848
<212> TYPE: DNA
<213> ORGANISM: Homo sapiens

<400> SEQUENCE: 35

```
tggccactcc ctctctgcgc gctcgctcgc tcactgaggc cgggcgacca aggtcgccc       60 gacgcccggg ctttgcccgg gcggcctcag tgagcgagcg agcgcgcaga gagggagtgg     120
ccaactccat cactagggt tcctagatct gaattcggta cccgttacat aacttacggt     180
aaatggcccg cctggctgac cgcccaacga cccccgccca ttgacgtcaa taatgacgta     240
```

```
tgttcccata gtaacgccaa tagggacttt ccattgacgt caatgggtgg agtatttacg      300
gtaaactgcc cacttggcag tacatcaagt gtatcatatg ccaagtacgc ccctattga       360 cgtcaatgac ggtaaatggc ccgcctggca ttatgcccag tacatgacct tatgggactt     420
tcctacttgg cagtacatct acgtattagt catcgctatt accatggtga tgcggttttg      480
gcagtacatc aatgggcgtg gatagcggtt tgactcacgg ggatttccaa gtctccaccc     540
cattgacgtc aatgggagtt tgttttggca ccaaaatcaa cgggactttc caaaatgtcg      600
taacaactcc gccccattga cgcaaatggg cggtaggcgt gtacggtggg aggtctatat     660
aagcagagct cgtttagtga accgtcagat cgcctggaga cgccatccac gctgttttga     720
cctccataga agacaccggg accgatccag cctccggact ctagaggatc cggtactcga     780
attttcacca tggtttggtg ggaagaagta gaggactgtt atgaaagaga agatgttcaa     840
aagaaaacat tcacaaaatg ggtaaatgca aattttcta gtttgggaa gcagcatatt       900 gagaacctct tcagtgacct acaggatggg aggcgcctcc tagacctcct cgaaggcctg     960
acagggcaaa aactgccaaa agaaaaagga tccacaagag ttcatgccct gaacaatgtc    1020
aacaaggcac tgcgggtttt gcagaacaat aatgttgatt tagtgaatat tggaagtact   1080
gacatcgtag atgaaaatca taaactgact cttggtttga tttggaatat aatcctccac    1140
tggcaggtca aaaatgtaat gaaaaatatc atggctggat tgcaacaaac caacagtgaa    1200
aagattctcc tgagctgggt ccgacaatca actcgtaatt atccacaggt taatgtaatc    1260
aacttcacca ccagctggtc tgatggcctg gctttgaatg ctctcatcca tagtcatagg   1320
ccagacctat ttgactggaa tagtgtggtt tgccagcagt cagccacaca acgactggaa    1380
catgcattca acatcgccag atatcaatta ggcatagaga aactactcga tcctgaagat   1440
gttgatacca cctatccaga taagaagtcc atcttaatgt acatcacatc actcttccaa    1500
gttttgcctc aacaagtgag cattgaagcc atccaggaag tggaaatgtt gccaaggcca   1560
cctaaagtga ctaaagaaga acattttcag ttacatcatc aaatgcacta ttctcaacag    1620
atcacggtca gtctagcaca gggatatgag agaacttctt cccctaagcc tcgattcaag    1680
agctatgcct acacacaggc tgcttatgtc accacctctg accctacacg gagcccattt    1740
ccttcacagc atttggaagc tcctgaagac aagtcatttg gcagttcatt gatggagagt    1800
gaagtaaacc tggaccgtta tcaaacagct ttagaagaag tattatcgtg gcttctttct    1860
gctgaggaca cattgcaagc acaaggagag atttctaatg atgtggaagt ggtgaaagac    1920
cagtttcata ctcatgaggg gtacatgatg gatttgacag cccatcaggg ccgggttggt    1980
aatattctac aattgggaag taagctgatt ggaacaggaa aattatcaga agatgaagaa    2040
actgaagtac aagagcagat gaatctccta aattcaagat gggaatgcct cagggtagct    2100
agcatggaaa acaaagcaa tttacataga gttttaatgg atctccagaa tcagaaactg    2160
aaagagttga atgactggct aacaaaaaca gaagaaagaa caaggaaaat ggaggaagag    2220
cctcttggac ctgatcttga agacctaaaa cgccaagtac aacaacataa ggtgcttcaa    2280
gaagatctag aacaagaaca agtcagggtc aattctctca ctcacatggt ggtggtagtt    2340
gatgaatcta gtggagatca cgcaactgct gctttggaag aacaacttaa ggtattggga    2400
gatcgatggg caaacatctg tagatggaca gaagaccgct gggttctttt acaagacact    2460
catagattac tgcaacagtt cccccctggac ctggaaaagt ttcttgcctg gcttacagaa    2520
gctgaaacaa ctgccaatgt cctacaggat gctacccgta aggaaaggct cctagaagac    2580
```

```
tccaagggag taaaagagct gatgaaacaa tggcaagacc tccaaggtga aattgaagct    2640
cacacagatg tttatcacaa cctggatgaa aacagccaaa aaatcctgag atccctggaa    2700
ggttccgatg atgcagtcct gttacaaaga cgtttggata acatgaactt caagtggagt    2760
gaacttcgga aaaagtctct caacattagg tcccatttgg aagccagttc tgaccagtgg    2820
aagcgtctgc acctttctct gcaggaactt ctggtgtggc tacagctgaa agatgatgaa    2880
ttaagccggc aggcacctat tggaggcgac tttccagcag ttcagaagca gaacgatgta    2940
catagggcct tcaagaggga attgaaaact aaagaacctg taatcatgag tactcttgag    3000
actgtacgaa tatttctgac agagcagcct ttggaaggac tagagaaact ctaccaggag    3060
cccagagagc tgcctcctga ggagagagcc cagaatgtca ctcggcttct acgaaagcag    3120
gctgaggagg tcaatactga gtgggaaaaa ttgaacctgc actccgctga ctggcagaga    3180
aaaatagatg agaccttga aagactccag gaacttcaag aggccacgga tgagctggac    3240
ctcaagctgc gccaagctga ggtgatcaag ggatcctggc agcccgtggg cgatctcctc    3300
attgactctc tccaagatca cctcgagaaa gtcaaggcac ttcgaggaga aattgcgcct    3360
ctgaaagaga acgtgagcca cgtcaatgac cttgctcgcc agcttaccac tttgggcatt    3420
cagctctcac cgtataacct cagcactctg aagacctga acaccagatg gaagcttctg    3480
caggtggccg tcgaggaccg agtcaggcag ctgcatgaag cccacaggga ctttggtcca    3540
gcatctcagc actttctttc cacgtctgtc cagggtccct gggagagagc catctcgcca    3600
aacaaagtgc cctactatat caaccacgag actcaaacaa cttgctggga ccatcccaaa    3660
atgacagagc tctaccagtc tttagctgac ctgaataatg tcagattctc agcttatagg    3720
actgccatga aactccgaag actgcagaag gcccttgct tggatctctt gagcctgtca    3780
gctgcatgtg atgccttgga ccagcacaac ctcaagcaaa atgaccagcc catggatatc    3840
ctgcagatta ttaattgttt gaccactatt tatgaccgcc tggagcaaga gcacaacaat    3900
ttggtcaacg tccctctctg cgtggatatg tgtctgaact ggctgctgaa tgtttatgat    3960
acgggacgaa cagggaggat ccgtgtcctg tcttttaaaa ctggcatcat ttccctgtgt    4020
aaagcacatt tggaagacaa gtacagatac cttttcaagc aagtggcaag ttcaacagga    4080 tttttgtgacc agcgcaggct gggcctcctt ctgcatgatt ctatccaaat tccaagacag    4140
ttgggtgaag ttgcatcctt tgggggcagt aacattgagc aagtgtccg gagctgcttc    4200 caatttgcta ataataagcc agagatcgaa gcggccctct tcctagactg gatgagactg    4260
gaaccccagt ccatggtgtg gctgcccgtc ctgcacagag tggctgctgc agaaactgcc    4320
aagcatcagg ccaaatgtaa catctgcaaa gagtgtccaa tcattggatt caggtacagg    4380
agtctaaagc actttaatta tgacatctgc caaagctgct ttttttctgg tcgagttgca    4440
aaaggccata aaatgcacta tcccatggtg gaatattgca ctccgactac atcaggagaa    4500
gatgttcgag acttttgccaa ggtactaaaa acaaatttc gaaccaaaag gtattttgcg    4560
aagcatcccc gaatgggcta cctgccagtg cagactgtct tagagggga caacatggaa    4620 actcccgaca caatgtagtc gagaggccta ataaagagct cagatgcatc gatcagagtg    4680
tgttggtttt ttgtgtgaga tctaggaacc cctagtgatg gagttggcca ctccctctct    4740
gcgcgctcgc tcgctcactg aggccgcccg ggcaaagccc gggcgtcggg cgacctttgg    4800
tcgcccggcc tcagtgagcg agcgagcgcg cagagaggga gtggccaa                 4848
```

<210> SEQ ID NO 36
<211> LENGTH: 5060

<212> TYPE: DNA
<213> ORGANISM: Homo sapiens

<400> SEQUENCE: 36

| | | | | |
|---|---|---|---|---|
| ttggccactc | cctctctgcg | cgctcgctcg | ctcactgagg | ccgggcgacc aaaggtcgcc | 60 |
| cgacgcccgg | gctttgcccg | ggcggcctca | gtgagcgagc | gagcgcgcag agagggagtg | 120 |
| gccaactcca | tcactagggg | ttcctagatc | tgaattcggt | accactacgg gtctaggctg | 180 |
| cccatgtaag | gaggcaaggc | ctggggacac | ccgagatgcc | tggttataat taacccagac | 240 |
| atgtggctgc | cccccccccc | ccaacacctg | ctgcctgagc | ctcaccccca ccccggtgcc | 300 |
| tgggtcttag | gctctgtaca | ccatggagga | gaagctcgct | ctaaaataa ccctgtccct | 360 |
| ggtggatcgg | tacccgttac | ataacttacg | gtaaatggcc | cgcctggctg accgcccaac | 420 |
| gacccccgcc | cattgacgtc | aataatgacg | tatgttccca | tagtaacgcc aatagggact | 480 |
| ttccattgac | gtcaatgggt | ggagtattta | cggtaaactg | cccacttggc agtacatcaa | 540 |
| gtgtatcata | tgccaagtac | gccccctatt | gacgtcaatg | acggtaaatg gcccgcctgg | 600 |
| cattatgccc | agtacatgac | cttatgggac | tttcctactt | ggcagtacat ctacgtatta | 660 |
| gtcatcgcta | ttaccatggt | gatgcggttt | tggcagtaca | tcaatgggcg tggatagcgg | 720 |
| tttgactcac | ggggatttcc | aagtctccac | cccattgacg | tcaatgggag tttgttttgg | 780 |
| caccaaaatc | aacgggactt | tccaaaatgt | cgtaacaact | ccgccccatt gacgcaaatg | 840 |
| ggcggtaggc | gtgtacggtg | ggaggtctat | ataagcagag | ctcgtttagt gaaccgtcag | 900 |
| atcgcctgga | gacgccatcc | acgctgtttt | gacctccata | aagacaccg ggaccgatcc | 960 |
| agcctccgga | ctctagagga | tccggtactc | gaattttcac | catggtttgg tgggaagaag | 1020 |
| tagaggactg | ttatgaaaga | gaagatgttc | aaaagaaaac | attcacaaaa tgggtaaatg | 1080 |
| cacaattttc | taagtttggg | aagcagcata | ttgagaacct | cttcagtgac ctacaggatg | 1140 |
| ggaggcgcct | cctagacctc | ctcgaaggcc | tgacagggca | aaaactgcca aaagaaaaag | 1200 |
| gatccacaag | agttcatgcc | ctgaacaatg | tcaacaaggc | actgcgggtt ttgcagaaca | 1260 |
| ataatgttga | tttagtgaat | attggaagta | ctgacatcgt | agatggaaat cataaactga | 1320 |
| ctcttggttt | gatttggaat | ataatcctcc | actggcaggt | caaaaatgta atgaaaaata | 1380 |
| tcatggctgg | attgcaacaa | accaacagtg | aaaagattct | cctgagctgg gtccgacaat | 1440 |
| caactcgtaa | ttatccacag | gttaatgtaa | tcaacttcac | caccagctgg tctgatggcc | 1500 |
| tggctttgaa | tgctctcatc | catagtcata | ggccagacct | atttgactgg aatagtgtgg | 1560 |
| tttgccagca | gtcagccaca | caacgactgg | aacatgcatt | caacatcgcc agatatcaat | 1620 |
| taggcatag | gaaactactc | gatcctgaag | atgttgatac | cacctatcca gataagaagt | 1680 |
| ccatcttaat | gtacatcaca | tcactcttcc | aagttttgcc | tcaacaagtg agcattgaag | 1740 |
| ccatccagga | agtggaaatg | ttgccaaggc | cacctaaagt | gactaaagaa gaacattttc | 1800 |
| agttacatca | tcaaatgcac | tattctcaac | agatcacggt | cagtctagca cagggatatg | 1860 |
| agagaacttc | ttcccctaag | cctcgattca | agagctatgc | ctacacacag gctgcttatg | 1920 |
| tcaccacctc | tgaccctaca | cggagcccat | ttccttcaca | gcatttggaa gctcctgaag | 1980 |
| acaagtcatt | tggcagttca | ttgatggaga | gtgaagtaaa | cctggaccgt atcaaacag | 2040 |
| ctttagaaga | agtattatcg | tggcttcttt | ctgctgagga | cacattgcaa gcacaaggag | 2100 |
| agatttctaa | tgatgtggaa | gtggtgaaag | accagtttca | tactcatgag ggtacatga | 2160 |
| tggatttgac | agcccatcag | ggccggggttg | gtaatattct | acaattggga agtaagctga | 2220 |

-continued

| | |
|---|---|
| ttggaacagg aaaattatca gaagatgaag aaactgaagt acaagagcag atgaatctcc | 2280 |
| taaattcaag atgggaatgc ctcagggtag ctagcatgga aaaacaaagc aatttacata | 2340 |
| gagtttaat ggatctccag aatcagaaac tgaaagagtt gaatgactgg ctaacaaaaa | 2400 |
| cagaagaaag aacaaggaaa atggaggaag agcctcttgg acctgatctt gaagacctaa | 2460 |
| aacgccaagt acaacaacat aaggtgcttc aagaagatct agaacaagaa caagtcaggg | 2520 |
| tcaattctct cactcacatg gtggtggtag ttgatgaatc tagtggagat cacgcaactg | 2580 |
| ctgctttgga agaacaactt aaggtattgg gagatcgatg ggcaaacatc tgtagatgga | 2640 |
| cagaagaccg ctgggttctt ttacaagaca ctcatagatt actgcaacag ttcccctgg | 2700 |
| acctggaaaa gtttcttgcc tggcttacag aagctgaaac aactgccaat gtcctacagg | 2760 |
| atgctacccg taaggaaagg ctcctagaag actccaaggg agtaaagag ctgatgaaac | 2820 |
| aatggcaaga cctccaaggt gaaattgaag ctcacacaga tgtttatcac aacctggatg | 2880 |
| aaaacagcca aaaaatcctg agatccctgg aaggttccga tgatgcagtc ctgttacaaa | 2940 |
| gacgtttgga taacatgaac ttcaagtgga gtgaacttcg gaaaaagtct ctcaacatta | 3000 |
| ggtcccattt ggaagccagt tctgaccagt ggaagcgtct gcaccttct ctgcaggaac | 3060 |
| ttctggtgtg gctacagctg aaagatgatg aattaagccg gcaggcacct attggaggcg | 3120 |
| actttccagc agttcagaag cagaacgatg tacataggc cttcaagagg gaattgaaaa | 3180 |
| ctaaagaacc tgtaatcatg agtactcttg agactgtacg aatatttctg acagagcagc | 3240 |
| ctttggaagg actagagaaa ctctaccagg agcccagaga gctgcctcct gaggagagag | 3300 |
| cccagaatgt cactcggctt ctacgaaagc aggctgagga ggtcaatact gagtgggaaa | 3360 |
| aattgaacct gcactccgct gactggcaga gaaaaataga tgagacccctt gaaagactcc | 3420 |
| aggaacttca agaggccacg gatgagctgg acctcaagct gcgccaagct gaggtgatca | 3480 |
| agggatcctg gcagcccgtg ggcgatctcc tcattgactc tctccaagat cacctcgaga | 3540 |
| aagtcaaggc acttcgagga gaaattgcgc ctctgaaaga gaacgtgagc cacgtcaatg | 3600 |
| accttgctcg ccagcttacc actttgggca ttcagctctc accgtataac ctcagcactc | 3660 |
| tggaagacct gaacaccaga tggaagcttc tgcaggtggc cgtcgaggac cgagtcaggc | 3720 |
| agctgcatga agcccacagg gactttggtc cagcatctca gcactttctt ccacgtctg | 3780 |
| tccagggtcc ctgggagaga gccatctcgc caaacaaagt gccctactat atcaaccacg | 3840 |
| agactcaaac aacttgctgg gaccatccca aaatgacaga gctctaccag tctttagctg | 3900 |
| acctgaataa tgtcagattc tcagcttata ggactgccat gaaactccga agactgcaga | 3960 |
| aggccctttg cttggatctc ttgagcctgt cagctgcatg tgatgccttg gaccagcaca | 4020 |
| acctcaagca aaatgaccag cccatggata tcctgcagat tattaattgt ttgaccacta | 4080 |
| tttatgaccg cctggagcaa gagcacaaca atttggtcaa cgtccctctc tgcgtggata | 4140 |
| tgtgtctgaa ctggctgctg aatgtttatg atacgggacg aacagggagg atccgtgtcc | 4200 |
| tgtcttttaa aactggcatc atttccctgt gtaaagcaca tttggaagac aagtacagat | 4260 |
| accttttcaa gcaagtggca agttcaacag gattttgtga ccagcgcagg ctgggcctcc | 4320 |
| ttctgcatga ttctatccaa attccaagac agttgggtga agttgcatcc tttgggggca | 4380 |
| gtaacattga gccaagtgtc cggagctgct tccaatttgc taataataag ccagagatcg | 4440 |
| aagcggccct cttcctagac tggatgagac tggaacccca gtccatggtg tggctgcccg | 4500 |
| tcctgcacag agtggctgct gcagaaactg ccaagcatca ggccaaatgt aacatctgca | 4560 |
| aagagtgtcc aatcattgga ttcaggtaca ggagtctaaa gcactttaat tatgacatct | 4620 |

```
gccaaagctg cttttttct ggtcgagttg caaaaggcca taaaatgcac tatcccatgg     4680
tggaatattg cactccgact acatcaggag aagatgttcg agactttgcc aaggtactaa    4740
aaaacaaatt tcgaaccaaa aggtattttg cgaagcatcc ccgaatgggc tacctgccag    4800
tgcagactgt cttagagggg gacaacatgg aaactcccga cacaatgtag tcgagaggcc    4860
taataaagag ctcagatgca tcgatcagag tgtgttggtt ttttgtgtga gatctaggaa    4920
cccctagtga tggagttggc cactccctct ctgcgcgctc gctcgctcac tgaggccgcc    4980
cgggcaaagc ccgggcgtcg ggcgaccttt ggtcgcccgg cctcagtgag cgagcgagcg    5040
cgcagagagg gagtggccaa                                                5060
```

DNA SEQUENCES COMPRISING DYSTROPHIN MINIGENES AND METHODS OF USE THEREOF

This application claims the priority of U.S. Provisional Patent application No. 60/200,777, filed Apr. 28, 2000.

TECHNICAL FIELD

The present invention relates to novel dystrophin minigenes that retain the essential biological functions of a full length dystrophin gene, and methods of treatment for Duchenne muscular dystrophy (DMD) and Becker muscular dystrophy (BMD) in a mammalian subject using the dystrophin minigenes.

BACKGROUND OF INVENTION

Duchenne muscular dystrophy (DMD) is an X-linked genetic muscle disease affecting 1 of every 3,500 newborn males (Kunkel et al. *Nature* (London) 322, 73–77 [1986]). The progressive muscle degeneration and weakness usually confine the patients to wheelchairs by their early teens, and lead to death by their early twenties. DMD is caused by recessive mutations in the dystrophin gene, the largest gene known to date, which spans nearly 3 million base-pairs on the X-chromosome with 79 exons, a coding sequence of about 11 kb, and a high rate of de novo mutations. (Koenig et al. *Cell* 50, 509–517 [1987]).

Dystrophin is an enormous rod-like protein of 3,685 amino acids (aa) localized beneath the inner surface of muscle cell membrane (Watkins, S. C. et al. *Nature* 333, 863–866 [1988]). It functions through four major structural domains: a N-terminal domain (1–756 aa), a central rod domain (757–3122 aa), a cysteine rich (CR) domain (3123–3409aa), and a distal C-terminal domain (3410–3685 aa). The N-terminal domain binds to the F-actin of cytoskeletal structures, while the CR domain along with the distal C-terminal domain anchors to the cell membrane via dystrophin-associated protein (DAP) complexes, thus, dystrophin crosslinks and stabilizes the muscle cell membrane and cytoskeleton. The central rod domain contains 24 triple-helix rod repeats (R1-R24) and 4 hinges (H1–H4). Each repeat is approximately 109 aa long. (Koenig et al. *J Biol Chem* 265, 4560–4566 [1990]). The central rod domain presumably functions as a "shock absorber" during muscle contraction. Dystrophin crosslinks and stabilizes the muscle cell membrane and cytoskeleton. The absence of a functional dystrophin results in the loss of DAP complexes and causes instability of myofiber plasma membrane. These deficiencies in turn lead to chronic muscle damage and degenerative pathology.

The vast majority of DMD mutations disrupt the dystrophin mRNA reading frame or introduce a stop codon that prematurely ends protein translation (Monaco et al. *Genomics* 2, 90–95 [1988]). In the less severe allelic form of the disease, Becker muscular dystrophy (BMD), dystrophin gene mutations are usually such that the mRNA reading frame is maintained. Thus in BMD patients, some functional gene product, albeit of reduced quantity and/or quality, is synthesized that contributes to the milder phenotype (Hoffman et al. *N. Engl. J Med.* 318, 1363–1368 [1988]).

The mdx mouse (Bulfield et al. *Proc. Natl. Acad. Sci. USA* 81, 1189–1192 [1984]) is an animal model of DMD. The genetic lesion in the mdx dystrophin gene is a nonsense mutation at base 3185 of the mRNA that causes premature termination of translation within exon 23. This nonsense mutation precludes synthesis of a functional protein.

Due to the lack of effective treatment for DMD, novel genetic approaches including cell therapy and gene therapy have been actively explored. However, clinical trials of myoblast transplantation have met with little success owing to the poor survival of the transplanted cells (Gussoni et al., *Nature Med* 3, 970–977 [1997]). It was recently reported that gentamicin treatment in mdx mice led to the suppression of the premature stop codon in the dystrophin gene, and the subsequent expression and localization of functional dystrophin to the cell membrane (Barton-Davis et al. *J Clin Invest.* 104, 375–381 [1999]). This treatment could prove effective in up to 15% of patient with DMD.

Somatic gene transfer offers a new approach to replace the defective dystrophin gene. A preferred approach for introducing genetic material encoding a gene product into an organ or a tissue is by use of a viral vector. In this situation, the genetic material encoding the gene product is inserted into the viral genome (or a partial viral genome). The regulatory elements directing the expression of the gene product can be included with the genetic material inserted into the viral genome (i.e., linked to the gene inserted into the viral genome) or can be provided by the viral genome itself, for example, a retrovirus long terminal repeat (LTR) or an adeno-associated virus (AAV) inverted terminal repeat (ITR). Infection of cells with a viral vector has the advantage that molecules encoded within the viral vector, e.g., by a cDNA contained in the viral vector, are expressed efficiently in cells which have taken up viral vector nucleic acid and viral vector systems can be used in vivo. Different viral vectors are described separately in the subsections below.

1. Adenovirus vectors: The genome of an adenovirus can be manipulated such that it encodes and expresses a gene product of interest but is inactivated in terms of its ability to replicate in a normal lytic viral life cycle (Curiel, *Ann N Y Acad Sci* 886, 158–71 [1999]). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells and muscle cells. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Haj-Ahmand et al. J. Virol. 57, 267–273 [1986]). Most replication-defective adenoviral vectors currently in use are deleted for all or parts of the viral E1 and E3 genes but retain as much as 80% of the adenoviral genetic material. Adenoviral vectors deleted for all viral coding regions are also described by Kochanek et al. and Chamberlain et al. (U.S. Pat. Nos. 5,985,846 and 6,083,750).

Adenovirus vectors have been successfully tested in dystrophic animal models (Ragot et al. *Nature* 361, 647–50 [1993]; Howell et al. *Hum Gene Ther* 9, 629–34 [1998]). Nonetheless, the immunogenicity and inefficiency of infecting mature muscle cells remain major hurdles to overcome before the adenovirus vectors can be safely used in humans.

2. Herpes simplex virus (HSV) vectors: The main feature of an HSV vector is that it has very large packaging capacity, is usually replication defective and does not integrate into the host genome. HSV infects cells of the nervous system (Fink et al. *Annu Rev Neurosci* 19, 265–287, [1996]). The virus contains more than 80 genes, one of which (IE3) can be replaced to create the vector. The generation of HSV vectors with deletions in many of the immediate early gene products has resulted in vectors with reduced toxicity and antigenicity, as well as prolonged expression in vivo. However, these modifications also result in a lower virus yield. Construction of HSV vectors is described in U.S. Pat. No. 5,661,033.

3. Retrovirus vectors: Defective retroviruses are well characterized for use in gene transfer for gene therapy purposes (Miller A D *Blood* 76, 271–278 [1990]). The members of the family Retroviridae are characterized by the presence of reverse transcriptase in their virions. There are several genera included within this family, including Cisternavirus A, Oncovirus A, Oncovirus B, Oncovirus C, Oncovirus D, Lentivirus, and Spumavirus.

A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in "Current Protocols in Molecular Biology, Ausubel, F. M. et al. (eds.) Greene Publishing Associates, (1989), Sections 9.10–9.14" and other standard laboratory manuals. Examples of suitable retroviruses include pLJ, pZIP, pWE and pEM which are well known to those skilled in the art. Examples of suitable packaging virus cell lines include .psi.Crip, .psi.Cre, .psi.2 and .psi.Am.

Retroviruses have been used to introduce a variety of genes into many different cell types, including epithelial cells, endothelial cells, lymphocytes, myoblasts, hepatocytes, hematopoietic stem cells, in vitro, and/or in vivo (U.S. Pat. Nos. 4,868,116; 5,449,614 and 6,207,455). Retroviral vectors require target cell division in order to be integrated into the host genome to stably introduce nucleic acid into the cell. Thus, it may be necessary to stimulate replication of the target cell. Successful transductions of hematopoietic stem or progenitor cells with retroviral vectors in an ex vivo setting have been reported. However, Recombinant retroviral vectors can only accommodate about 8 kb to 10 kb of foreign DNA. This packaging capacity also limits its use in the genetic treatment of DMD.

4. Lentivirus vectors. Lentiviruses also belong to the retrovirus family, but they can infect both dividing and non-dividing cells. The best-known lentivirus is the human immunodeficiency virus (HIV), which has been disabled and developed as a vector for in vivo gene delivery. Like the simple retroviruses, HIV has three genes termed gag, pol and env, it also carries genes for six accessory proteins termed tat, rev, vpr, vpu, nef and vif. Using the retrovirus vectors as a model, lentivirus vectors have been made, with the transgene enclosed between the LTRs and a packaging sequence (Naldni et al. *Science* 272, 263–267 [1996]). Some of the accessory proteins can be eliminated without affecting production of the vector or efficiency of infection.

When lentiviral vectors are injected into rodent brain, liver, muscle, eye or pancreatic islet cells, they give sustained expression for over six months. Little is known about the possible immune problems associated with lentiviral vectors. Furthermore, there seems to be no potent antibody response. A major concern about lentiviral vector is its safety in human applications. However, recent development in producing the third generation lentiviral vectors with more deletion in viral genes and improved safety may allow for the general application of lentiviral vectors to in vivo gene therapy.

5. Adeno-associated viruses (AAV) vectors: AAV is a naturally occurring defective virus that requires another virus, such as an adenovirus or a herpes virus, as a helper virus for efficient replication and a productive life cycle (Muzyczka et al. *Curr. Topics in Micro. and Immunol.* 158, 97–129 [1992]). AAV vector is the only viral vector system that is based on a non-pathogenic and replication defective virus. It is also one of the few viruses that may integrate its DNA into non-dividing cells, and exhibits a high frequency of stable integration (Flotte et al. *Am. J Respir. Cell. Mol. Biol.* 7, 349–356 [1992]; Samulski et al. *J. Virol.* 63, 3822–3828 [1989]). Vectors containing as little as 300 base pairs of AAV DNA can be packaged.

AAV vectors have been successfully used to establish efficient and long-term gene expression in vivo in a variety of tissues without significant immune response or toxicity (Xiao et al. *J. Virol.* 70, 8098–108 [1996]; Kessler et al. *Proc Natl Acad Sci USA* 93, 14082–7 [1996]; Xiao et al. *J Virol* 72, 10222–6 [1998]). Unlike other viral vectors, AAV readily bypasses extracellular barriers due to its small viral particle size (20 nm) that facilitates efficient transduction of muscle myofibers of various maturity (Pruchnic et al. *Hum Gene Ther* 11, 521–36 [2000]). AAV can also be delivered into a large number of muscle groups via the blood vessels (Greelish et al. *Nat. Med.* 5, 439–443 [1999]) The unparalleled efficiency and safety have led to an increasing interest in AAV-mediated gene therapy for genetic muscle disorders, as well as for metabolic diseases. However, a major obstacle for AAV vectors is the limited packaging size that only allows for genes smaller than 4.7 kb (Song et al. *Proc Natl Acad Sci USA* 95, 14384–8 [1998]; Kay et al. *Nat Genet* 24, 257–261 [2000]), therefore precludes such large gene as dystrophin with a cDNA of 14 kb.

Other viral vector systems that may have application in the subject invention have been derived from vaccinia virus (Chen et al. *J Immunother* 24, 46–57 [2001]), and several RNA viruses. The plus-strand RNA viridae, such as polio (Bledsoe et al. *Nat Biotechnol.* 18, 964–9 [2000]), hepatitis A (Romano G. *Stem Cells;* 18, 19–39 [2000]), and sindbis virus (Wahlfors et al. *Gene Ther* 7, 472–80 [2000]) are being developed for high-level gene expression, following either viral infection or delivery of nucleic acids using a nonviral system. These viruses express a replicase protein that can specifically replicate the viral RNA. By inserting a transgene in place of the viral capsid gene(s), it is possible to generate a chimeric RNA that replicates autonomously in the cell and expresses a high level of protein from the plus-coding strand of RNA. These viral vectors are well suited for immunization strategies in which high, transient gene expression is needed to induce an immune response to the transduced cells.

In addition to the viral gene transfer vectors, powerful non-viral gene transfer vectors have also become available for clinical application in the past several years (Ropert et al. *Braz J Med Biol Res.* 32, 163–9 [1999]; Lee R J et al. *Crit Rev Ther Drug Carrier Syst* 14, 173–206 [1997]). These vectors rely on normal mechanisms used by mammalian cells for the uptake and intracellular transport of macromolecules to deliver genetic materials into cells. These vectors include cationic and other liposomes, DNA-viral conjugates, RNA/DNA oligonucleotides and, surprisingly, naked DNA molecules. Physical procedures, such as hydrodynamics-based and electroporation-based procedures have been used to improve gene transfer efficiency of some non-viral vectors (Zhang G. et al. *Gene Ther* 7, 1344–9 [2000]; Yamashita et al. *Cancer Res.* 61, 1005–12 [2001]). Recently, it was also reported that intraperitoneal injection of a β-galactosidase fused to the protein transduction domain from the human immunodeficiency virus TAT protein resulted in delivery of the fusion protein to all tissues in mice (Schwarze et al. *Science*, 3, 1569–1572 [1999]).

Somatic gene transfer using non-viral vectors carrying dystrophin gene have been attempted [Acsadi et al. *Nature* 352, 815–818 [1991]; Rando et al. *Proc. Natl. Acad. Sci USA* 97, 5363–5368 [2000]). Transgene expression was achieved with only very limited efficiency.

Previous attempts to generate dystrophin minigenes that were shorter than ½ of the full-length dystrophin failed to preserve the essential protective functions. Cox et al. and Greenberg et al. reported that expression of Dp 71, a 71 kD non-muscle product of the dystrophin gene that consists of the cysteine-rich and C-terminal domains of dystrophin (exon 63–79), in the skeletal muscle of dystrophin deficient mdx mice restored normal levels dystrophin associated proteins (DAPs). However, expression of Dp71 failed to alleviate symptoms of muscle degeneration [Cox et al. *Nature Genet* 8, 333–339 [1994]; Greenburg et al. *Nature Genet* 8, 340–344 [1994]). Similarly, Yuasa et al (Yuasa et al. *FEBS Lett* 425, 329–336 [1998]; Yamamoto et al. *Hum Gene Ther* 11, 669–80 [2000]) demonstrated that expression of dystrophin minigenes with both intact N- and C-terminal domains and 1 to 3 central rod repeats in mouse skeletal muscle was sufficient to restore DAP complexes but insufficient to restore myofiber morphology and to prevent dystrophic pathology.

SUMMARY OF THE INVENTION

The present invention provides dystrophin minigenes that are significantly reduced in size without compromising essential functions in protecting muscles from dystrophic phenotypes. The present invention also provides viral vectors carrying the dystrophin minigenes that are capable of mediating efficient and stable correction of both biochemical and physiological defects in a mammalian subject. Furthermore, the present invention provides a method that is more convenient and less time-consuming to discern the dystrophin functional domains in vivo and to optimize the minigenes for DMD gene therapy. Finally, the present invention provides a method for treatment of muscular dystrophy.

BRIEF DESCRIPTION OF THE DRAWINGS

FIG. 2b shows IF analysis of the dystrophin and DAP complexes in gastrocnemius muscle from 15-week old normal C57/B10 mice, from mdx mice treated either with vector AAV-MCK-Δ3849, AAV-MCK-Δ3990 or AAV-MCK-Δ4173, or from untreated mdx mice.

FIG. 4a shows protection of muscle plasma membrane integrity by dystrophin minigenes in mdx mice treated at 10 days of age.

DETAILED DESCRIPTION AND PREFERRED EMBODIMENTS OF THE INVENTION

Figure 1:
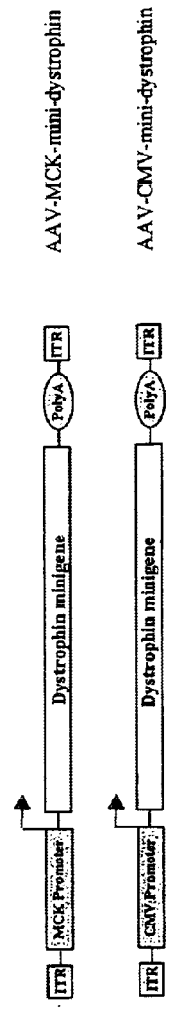
FIG. 1 shows the construction of highly truncated dystrophin minigenes and AAV vectors carrying the dystrophin minigene.

The practice of the present invention will employ, unless other wise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

As used in this specification and the appended claims, the singular forms "a," "an" and "the" include plural references unless the content clearly dictates other wise.

A. Definitions

In describing the present invention, the following terms will be employed, and are intended to be defined as indicated below.

"Gene transfer" or "gene delivery" refers to methods or systems for reliably introducing a particular nucleotide sequence (e.g., DNA) into targeted cells. The introduced nucleotide sequences may persist in vivo in episomal forms or integrate into the genome of the target cells. Gene transfer provides a unique approach for the treatment of acquired and inherited diseases, and a number of systems have been developed in the art for gene transfer into mammalian cells. See, e.g., U.S. Pat. No. 5,399,346.

As used herein, the term "effective amount" refers to a level of infection which brings about at least partially a desired therapeutic or prophylactic effect in an organ or tissue infected by the method of the present invention. The infection with an effective amount of the vector carrying genetic material of interest can then result in the modification of the cellular activities, e.g., a change in phenotype, in an organ or a tissue that has been infected by the method of the present invention. In a preferred embodiment, the infection with an effective amount of the vector carrying genetic material of interest results in modulation of cellular activity in a significant number of cells of an infected organ or a tissue.

A gene transfer "vector" refers to any agent, such as a plasmid, phage, transposon, cosmid, chromosome, liposome, DNA-viral conjugates, RNA/DNA oligonucleotides, virus, bacteria, etc., which is capable of transferring gene sequences into cells. Thus, the term includes cloning and expression vehicles, as well as viral and non-viral vectors. A vector may be targeted to specific cells by linking a target molecule to the vector. A targeting molecule is any agent that is specific for a cell or tissue type of interest, including for example, a ligand, antibody, sugar, receptor, or other binding molecule. The invention is also intended to include such other forms of vectors which serve equivalent functions and which become known in the art subsequently hereto.

An "AAV vector" refers to vectors derived from an adeno-associated virus serotype, including human AAV-1, AAV-2, AAV-3, AAV-4, AAV-5, AAV-6, avian AAV, ovian AAV, etc., and to vectors derived from more than one AAV serotype (hybrid AAV vectors). For example, a hybrid AAV vector may contain DNA sequences derived from both AAV-1 and AAV-2. An AAV vectors can have one or more of the AAV wild-type genes deleted in whole or part, preferably the rep and/or cap genes, but retain functional flanking ITR sequences. AAV vectors can be constructed using recombinant techniques that are known in the art to include one or more heterologous nucleotide sequences flanked on both ends (5' and 3') with functional AAV ITRs. In the practice of the invention, an AAV vector can include at least one AAV ITR and a suitable promoter sequence positioned upstream of the heterologous nucleotide sequence and at least one AAV ITR positioned downstream of the heterologous sequence.

A "recombinant AAV vector plasmid" refers to one type of recombinant AAV vector wherein the vector comprises a plasmid. As with AAV vectors in general, 5' and 3' ITRs flank the selected heterologous nucleotide sequence. AAV vectors can also include transcription sequences such as polyadenylation sites, as well as selectable markers or reporter genes, enhancer sequences, and other control elements which allow for the induction of transcription. Such control elements are described more fully below. In addition, an "AAV vector" can be stably introduced into a cell line or cell lines for the purpose of viral particle production. Such a cell line is usually termed as AAV packaging cell line.

As used herein, the term "recombinant AAV", "recombinant AAV particle" or "recombinant AAV virion" is defined as an infectious, replication-defective virus composed of an AAV protein shell encapsidating (i.e., surrounding with a protein coat) a heterologous nucleotide sequence, which in turn is flanked 5' and 3' by AAV ITRs. In this regard, single-stranded AAV nucleic acid molecules (either the sense/coding strand or the antisense/anticoding strand as those terms are generally defined) can be packaged into an AAV virion; both the sense and the antisense strands are equally infectious. When the recombinant AAV DNA is equal to or smaller than 50% of the full length viral genome (about 5,000 nucleotides), it can also be packaged as double-stranded hairpin-like DNA into AAV virion. Such virion is also fully infectious.

The term "recombinant AAV particle" or "recombinant AAV virion" also refers to a hybrid AAV particle in which the AAV protein shell and the encapsulated nucleotide sequence may be derived from AAVs of different serotype. For example, a hybrid AAV particle may contain AAV-1 capsid proteins and AAV-2 ITRs, or vice versa. It is also possible to create hybrid AAV capsid proteins using coding sequences from two or more AAV capsid genes. In addition, the capsid protein of a recombinant AAV may be manipulated by mutation, deletion, and/or insertion of amino acid sequence in order to modify the tropism of the recombinant AAV (Wu et al. *J. Virol* 74, 8635–47 [2000]; Girod et al. *Nat Med* 5, 1052–1056 [1999]).

A number of techniques for constructing recombinant AAV are known in the art. See, e.g., U.S. Pat. No. 5,173,414, Lebkowski et al. *Mol Cell Biol* 8, 3988–3996 [1988]; Carter B J, *Current Opinion in Biotechnology* 3, 533–539 [1992]; Muzyczka N, cited supra; and Zhou et al. *J. Exp. Med.* 179, 1867–1875 [1994]; Xiao et al. *J. Virol.* 72, 2224–32 [1998].

The term "expression control element" or "regulatory element" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. The term "promoter" is used herein in its ordinary sense to refer to a DNA regulatory sequence that are sufficient for RNA polymerase recognition, binding and transcription initiation. Additionally, a promoter includes sequences that modulate the recognition, binding and transcription initiation activity of RNA polymerase. Such sequences may be cis acting or may be responsive to trans acting factors. Depending upon the nature of the regulation, promoters may be constitutive or regulated. Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, muscle creatine kinase (MCK) promoter, myosin promoter, α-actin promoter and the like. Alternatively, the modified versions of the above promoters and even the synthetic muscle promoters (Li et al. *Nat Biotechnol* 17, 241–245, [1999]) may be included. Finally, the promoter may be an endogenous AAV promoter or AAV inverted terminal repeat (ITR).

The term "transduction" denotes the delivery of a DNA molecule to a recipient cell either in vivo or in vitro, via a replication-defective viral vector, such as via a recombinant AAV virion.

The term "muscle cell" or "tissue" refers to a cell or group of cells derived from muscle, including but not limited to cells and tissue derived from skeletal muscle; cardiac muscle, smooth muscle, e.g., from the digestive tract, urinary bladder and blood vessels. The term captures muscle cells both in vitro and in vivo. Thus, for example, an isolated cardiomyocyte would constitute a "muscle cell" for purposes of the present invention, as would a muscle cell as it exists in muscle tissue present in a subject in vivo. The term also encompasses both differentiated and nondifferentiated muscle cells, such as myocytes, myotubes, myoblasts, cardiomyocytes and cardiomyoblasts, and progenitor cells, for example, the muscle derived stem cells or the bone marrow derived stem cells that can become muscle cells after differentiation "Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "dystrophin minigene" refers to the novel dystrophin constructs created by extensive deletions in the central rod domain plus extensive deletion in the C-terminal domain of the human dystrophin cDNA. In addition, the dystrophin minigenes may contain a modified N-terminal domain in which DNA sequences surrounding the original protein translation initiation codon ATG are modified. The modified sequences enhance the mini-dystrophin protein synthesis. Alternatively, the dystrophin minigene may be a hybrid gene in which some of the domains are substituted with homologous domains from utrophin or spectrin genes (Tinsley et al, Nature 360, 591–593 [1992]; Koenig et al. Cell 53, 219–216 [1988]). In particular, utrophin is highly homologous to dystrophin in both structure and functions, so that their major domains should be interchangeable (Tinsley et al, Nature. 384, 349–353 [1996]; Deconinck et al, Nat Med. 3, 1216–21 [1997]; Rafael et al Nat Genet. 19, 79–82 [1998];). For example, the N-terminal and/or the C-terminal domains of dystrophin may be substituted with the utrophin counterparts in the dystrophin minigenes. Similarly, the central rod domain may consist of rod repeats from utrophin or spectrin genes. The dystrophin minigenes are smaller than the 5 kb packaging limit of AAV viral vectors. Furthermore, it is also plausible to construct a minigene of utrophin in a similar fashion as of the dystrophin minigene described in this invention. Because some DMD patients completely lack the dystrophin protein, the dystrophin minigene product may be a neo-antigen. Substitution of dystrophin domains with those of utrophin may lower immune responses.

The term "mini-dystrophin" refers to the polypeptides encoded by the dystrophin minigenes. Most importantly, the mini-dystrophins harbor biological functions that can protect the muscle from dystrophic pathology and symptoms.

The symbol "Δ" (delta) is a prefix for the dystrophin minigenes that contain deletions as described above.

By "mammalian subject" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

The term "expression cassette" refers to a construct of genetic material that contains coding sequences and enough regulatory information to direct proper transcription and translation of the coding sequences in a recipient cell.

B. Detailed Description of the Invention

To explore the feasibility of using viral vectors for DMD gene therapy, we have devised strategies to create novel dystrophin minigenes, which are small enough to be packaged into retrovirus or AAV vectors, and yet retain the essential functions needed for protecting muscle from the pathological symptoms. We have created minigenes in which up to 75% of the central rod domain (20 of the 24 rods; 2 of the 4 hinges), as well as nearly all the C-terminal domain (exons 71–78), are deleted (FIG. 1). These novel dystrophin minigenes, as small as only one third (⅓) of the 11 kb full-length dystrophin coding sequence, are significantly smaller than the 6.3 kb Becker-form mini-dystrophin gene (England et al. Nature 343, 180–2 [1990]) that was widely used in transgenic and gene therapy studies in mdx mice. The minigene comprises the N-terminus sequence of the dystrophin gene, the C-terminal cysteine-rich (CR) domain of the dystrophin gene, at least hinges H1 and H4 of dystrophin gene, and at least four rod repeats. The rod repeats may be chosen from the rod repeats of dystrophin, utrophin or spectrin genes, preferably from the 24 rod repeats of dystrophin gene, and most preferably from the group consisting of rod repeats R1, R2, R3, R22, R23 and R24 of dystrophin gene. The N-terminus of the dystryphin minigene may be modified to improve expression efficiency without affecting the functionality of the gene product. For example, the original sequence surrounding the translation initiation ATG codon of the dystrophin gene may be substituted by the Kozak sequence to increase the efficiency of protein synthesis. In one embodiment of the current invention, the three nucleotides upstream of the coding sequence may be changed from "AAA" to "CCA" and the fourth nucleotide in the coding sequence may be changes from "C" to "G". In addition, a portion or the entire N-terminus may be substituted by its counterpart of the utrophin gene. Similarly, the CR domain of the dystrophin minigene can also be substituted by its counterpart of the utrophin gene.

The dystrophin minigenes may be introduced into a mammalian subject using a variety of methods. It may be introduced into the subject in an expression cassette as a naked DNA with or without hydrodynamic-based or electroporation-based proceduces. It may be introduced into the subject using non-viral vectors such as liposomes or virus-liposome complexes, or with viral vectors such as adenovirus, HSV, baculovirus, retrovirus, lentivirus, and preferably AAV. Expression of the dystrophin minigenes may be controlled by a number of regulatory elements, including but not limited to, AAV inverted terminal repeat (ITR), retrovirus long terminal repeat (LTR), cytomeglovirus (CMV) immediate early promoter and/or enhancer, CMV enhancer and chicken β-actin promoter (CB promoter), α-actin promoter, myosin promoter, muscle-specific creatine kinase (MCK) promoter and/or enhancer, and the like. Alternatively, the modified versions of the above promoters and the synthetic muscle promoters (Li et al. cited supra) etc. may also be used.

Expression of dystrophin minigene may be detected by immunofluorescent staining and immunoblotting (Western blotting). The functionality of mini-dystrophin may be examined by determining whether the mini-dystrophins are capable of restoring the missing DAP complexes on the myofiber plasma membrane, including the sarcoglycan complex which is not found in untreated dystrophic muscle due to the primary deficiency of dystrophin. To further investi gate the functionality of the novel mini-dystrophins, it is essential to demonstrate that they can protect muscle from the pathological phenotypes. The onset of the pathology in mdx mice starts at around three weeks of age with massive waves of myofiber degeneration/regeneration. This process is characterized by the presence of central nuclei in myofibers, a primary pathological sign of muscular dystrophies. The absence or reduction of central nucleation after gene therapy would suggest that the therapy is successful. The position of nuclei in a muscle fiber may be determined by DAPI staining or H & E staining.

Muscle cryosections of 8 μm thickness may be immunofluorescently stained with the Mouse-on-Mouse Kit from the Vector Laboratories (Burlingame, Calif.) according to the manufacturer's protocol, except that the cryosections may be immediately treated with the blocking buffer without the fixation step (Li et al. *Gene Ther* 6, 74–82 [1999]). Monoclonal antibodies against dystrophin (NCL-Dys3 and NCL-Dys2) and against α-, β-, and γ-sarcoglycans (NCL-α-SARC, NCL-β-SARC and NCL-γ-SARC) may be purchased from Novocastra Laboratories Ltd (Burlingame, Calif.). Muscle cell nuclei may be counterstained with 0.01% DAPI (Sigma, St. Louis, Mo.) for 10 minutes. Photographs may be taken with a Nikon TE-300 fluorescent microscope.

Plasma membrane damage and leakage in dystrophic muscle is a major physiological defect and also a major pathological cause. To determine whether AAV mini-dystrophin treatment would be effective in protecting plasma membrane from mechanical damage, myofiber membrane integrity test may be performed by intravenous injection of Evans Blue dye. Evans Blue is a widely used vital red-fluorescent dye that is excluded by the healthy myofibers, but is taken up by the dystrophic myofibers containing leaky cell membrane due to contractile damages. A previous study of mdx mice revealed that the apoptotic myonuclei were mostly found in Evans Blue dye positive myofibers, thus correlating plasma membrane leakage and muscle cell apoptosis (Matsuda et al. *J Biochem* (*Tokyo*) 118, 959–64 [1995]).

Evans Blue dye (10 mg/ml in PBS) may be injected into the tail vein of C57/B10 mice, mdx mice, and AAV vector-treated mdx mice at the dose of 0.1 mg/gram of body weight. Following dye injection, mice may be allowed continuous swimming for 20 minutes. At 15 hours after Evans Blue injection, muscles may be collected and cryosectioned. Evans Blue dye positive myofibers may be observed under the fluorescent microscope with Rhodamine filters.

Muscle constrctile force improvement was evaluated in the mdx mice after treatment with AAV vectors containing the dystrophin minigene. Tibialis anterior (TA) muscles of 2 to 3 month old mdx mice were injected with AAV-MCK-3990 vector. The injection was given in such a way that one leg was treated while the other leg in the same animal was left untreated. The latter was used as a control. At 6 months after AAV treatment, the mdx mice were anesthetized with pentobarbital sodium (70 mg/kg, i.p.) and the entire TA muscle was removed and mounted in a vertical tissue chamber for in vitro force measurement. The muscle was stimulated (Grass model S-88 stimulator and current amplifier) by use of monophasic rectangular pulses of cathodal current (1.0-ms duration). Maximum tetanic force ($P_o$) was assessed using a stimulation frequency of 75 pps delivered in a 500 ms duration train. Following the determination of $P_o$, the ability of the TA muscle to sustain force generation during repetitive lengthening activations (which should induce maximal damage to the muscle) was assessed. Peak force measured prior to lengthening was termed $P_{ISO}$. Subsequently, the muscle was lengthened at a constant velocity of 1.0 $L_o$/s from 100 to 110% $L_o$. Stimulus trains were repeated every 2-min (duty cycle 0.004) for a total of 10 cycles. Changes in $P_{ISO}$ were used to index impairment of muscle function associated with the damages caused by lengthening activations.

C. Preferred Embodiments

The following examples are meant merely to exemplify several embodiments, and should not be interpreted as limiting the scope of the claims, which are delimited only by the specification.

EXAMPLE 1

Dystrophin Minigenes and AAV Vectors Carrying the Minigenes

This example describes the construction of highly truncated dystrophin minigenes and AAV vectors carrying the minigenes. The dystrophin minigene constructs were made mainly by PCR cloning method using Pfu polymerase (Stratagene, CA) and human dystrophin cDNA (GenBank # NM 004006) as the template. For consistency, the numbering of the nucleotide only includes the 11,058 bp dystrophin protein coding sequence (SEQ ID NO:1).

As depicted in FIG. 1, dystrophin minigene Δ4173 (SEQ ID NO:2) contains nucleotides 1-1992 (N-terminus, hinge H1 and rods R1, R2 & R3, SEQ ID NO:3) and 8059-10227 (rods R22, R23 & R24, hinge H4 and CR domain, SEQ ID NO:4) and 11047-11058 (the last 3 amino acids of dystrophin, SEQ ID NO:5).

Dystrophin minigene Δ3990 (SEQ ID NO:6) contains nucleotides 1-1668 (N-terminus, hinge H1 and rods R1 & R2, SEQ ID NO:7), 7270-7410 (hinge H3, SEQ ID NO:8), 8059-10227 (rods R22, R23 & R24, hinge H4 and CR domain, SEQ ID NO:4) and 11047-11058 (the last 3 amino acids of dystrophin, SEQ ID NO:5).

Dystrophin minigene Δ3849 (SEQ ID NO:9) contains nucleotides 1-1668 (N-terminus, hinge H1 and rods R1 & R2, SEQ ID NO:7), 8059-10227 (rods R22, R23 & R24, hinge H4 and CR domain, SEQ ID NO:4), and 11047-11058 (the last 3 amino acids of dystrophin, SEQ ID NO:5).

Dystrophin minigene Δ3531 (SEQ ID NO:10) contains nucleotide 1-1341 (N-terminus, hinge H1 and rods R1, SEQ ID NO:11), 8059-10277 (rods R22, R23 & R24, hinge H4 and CR domain, SEQ ID NO:4), and 11047-11058 (the last 3 amino acids of dystrophin, SEQ ID NO:5).

Dystrophin minigene Δ3510 (SEQ ID NO:12) contains nucleotide 1-1668 (N-terminus, hinge H1 and rods R1 & R2, SEQ ID NO:7), 8407-10277 (rods R23 & R24, hinge H4 and CR domain, SEQ ID NO:13) and 11047-11058 (the last 3 amino acids of dystrophin, SEQ ID NO:5).

Dystrophin minigene Δ3447 (SEQ ID NO:14) contains nucleotide 1-1992 (N-terminus, hinge H1 and rods R1, R2 & R3, SEQ ID NO:3), 8794-10277 (rod R24, hinge H4 and CR domain, SEQ ID NO:15) and 11047-11058 (the last 3 amino acids of dystrophin, SEQ ID NO:5).

The above constructs were made by blunt-end ligation of the Pfu amplified PCR products of each individual segment, so that all the protein coding sequences are precisely spliced together in frame. The PCR primers used in the reactions are listed in Table 1:

TABLE 1

PCR primers used in the cloning of dystrophin fragments

| Primer Names | Primer Sequence (5'-3') | Sequence position | | | |
|---|---|---|---|---|---|
| Forward primers: | | | | | |
| F1 (ATG-A) | ATTTTCACCATGGTTTGGTGGGAAGAAG | 1-19 | (28 bp) | SEQ ID NO:16 | |
| F2 (H3-1) | CAGCCTGACCTAGCTCCTGGACTGA | 7270-7294 | (25 bp) | SEQ ID NO:17 | |
| F3 (R22-1) | ACTCATAGATTACTGCAACAGTTCC | 8059-8083 | (25 bp) | SEQ ID NO:18 | |
| F4 (R23-1) | AGTTCTGACCAGTGGAAGCG | 8407-8427 | (20 bp) | SEQ ID NO:19 | |
| F5 (R24-1) | ACCCTTGAAAGACTCCAGGAAC | 8794-8816 | (22 bp) | SEQ ID NO:20 | |
| Reverse primers: | | | | | |
| R1 (R1-2) | TCTATGTAAATTGCTTTGTT | 1341-1361 | (20 bp) | SEQ ID NO:21 | |
| R2 (R2-2) | GTCTTGTAAAAGAACCCAGCGGTCT | 1668-1644 | (25 bp) | SEQ ID NO:22 | |
| R3 (R3-2) | CTGTGCTGTACTCTTTTCAAGTTTT | 1992-1968 | (25 bp) | SEQ ID NO:23 | |
| R4 (H3-2) | AGGTACCTCCAACATCAAGGAAGAT | 7410-7386 | (25 bp) | SEQ ID NO:24 | |
| R5 (Tail-2A) | CTACATTGTGTCGGGAGTTTCCATGTTGTC | 11058-11047, 10227-10210 | (30 bp) | SEQ ID NO:25 | |

The dystrophin minigenes were then subcloned into an AAV vector plasmid (SEQ ID NO:26) containing an MCK promoter, a 595 bp Hind III/BstE II fragment from plasmid p(+enh206) 358MCKCAT (Shield et al. *Mol Cell Biol* 16, 5058–68 [1996]), and a 60 bp small polyA signal sequence, resulting in AAV vector constructs AAV-MCK-Δ4173 (SEQ ID NO:27), AAV-MCK-Δ3990 (SEQ ID NO:28), AAV-MCK-Δ3849 (SEQ ID NO:29), AAV-MCK-3531 (SEQ ID NO:30), AAV-MCK-3510 (SEQ ID NO:31) and AAV-MCK-3447 (SEQ ID NO:32).

Similarly, the dystrophin minigenes were also cloned into an AAV vector plasmid (SEQ ID NO:33) containing a CMV promoter (620 bp) and the small polyA signal sequence, resulting in AAV vector constructs AAV-CMV-Δ3990 (SEQ ID NO:34), AAV-CMV-Δ3849 (SEQ ID NO:35). In addition, the dystrophin minigene Δ3849 was cloned into an AAV vector plasmid containing an MCK enhancer, a CMV promoter, and the small polyA signal sequence, resulting AAV vector construct AAV-E-CMV-3849 (SEQ ID NO:36).

The recombinant viral vector stocks were produced precisely according to the three-plasmid co-transfection method as described by Xiao et al. (cited supra). The AAV viral vectors were subsequently purified twice through CsCl density gradient ultracentrifugation using the previously published protocols (Snyder et al. in *Current Protocols in Human Genetics*, eds. Dracopoli et al. [John Wiley & Sons Ltd., New York], pp. 12.1.1–12.2.23. [1996]). The vector titers of viral particle number were determined by DNA dot blot method (Snyder et al. cited supra), and were approximately $5 \times 10^{12}$ genome copies (GC) per ml.

EXAMPLE 2
Restoration of DAP Complexes

This example describes whether dystrophin minigene products still retain the major biochemical functionality including submembrane localization and interaction with dystrophin associated protein (DAP) complexes. Healthy C57/B10 mice and dystrophic mdx mice were purchased from The Jackson Laboratory (Bar Harbor, Me.). Ten-day old mdx pups or 50-day old mdx adult mice were injected into the hindleg gastrocnemius muscle with 50 μl ($5 \times 10^{10}$ GC) of different AAV mini-dystrophin vectors.

Figure 2A:
FIG. 2a shows immunofluorescent (IF) analysis of the dystrophin and DAP complexes in gastrocnemius muscle of mdx muscle at 3-months after treatment with construct AAV-MCK-Δ3849 or AAV-MCK-Δ3990.
Figure 2A:
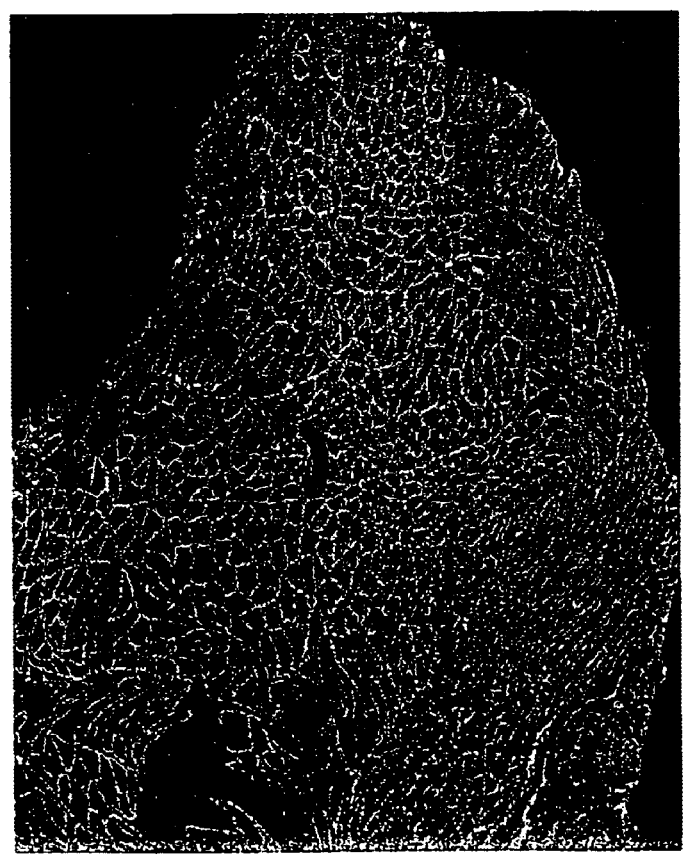
Figure 3:
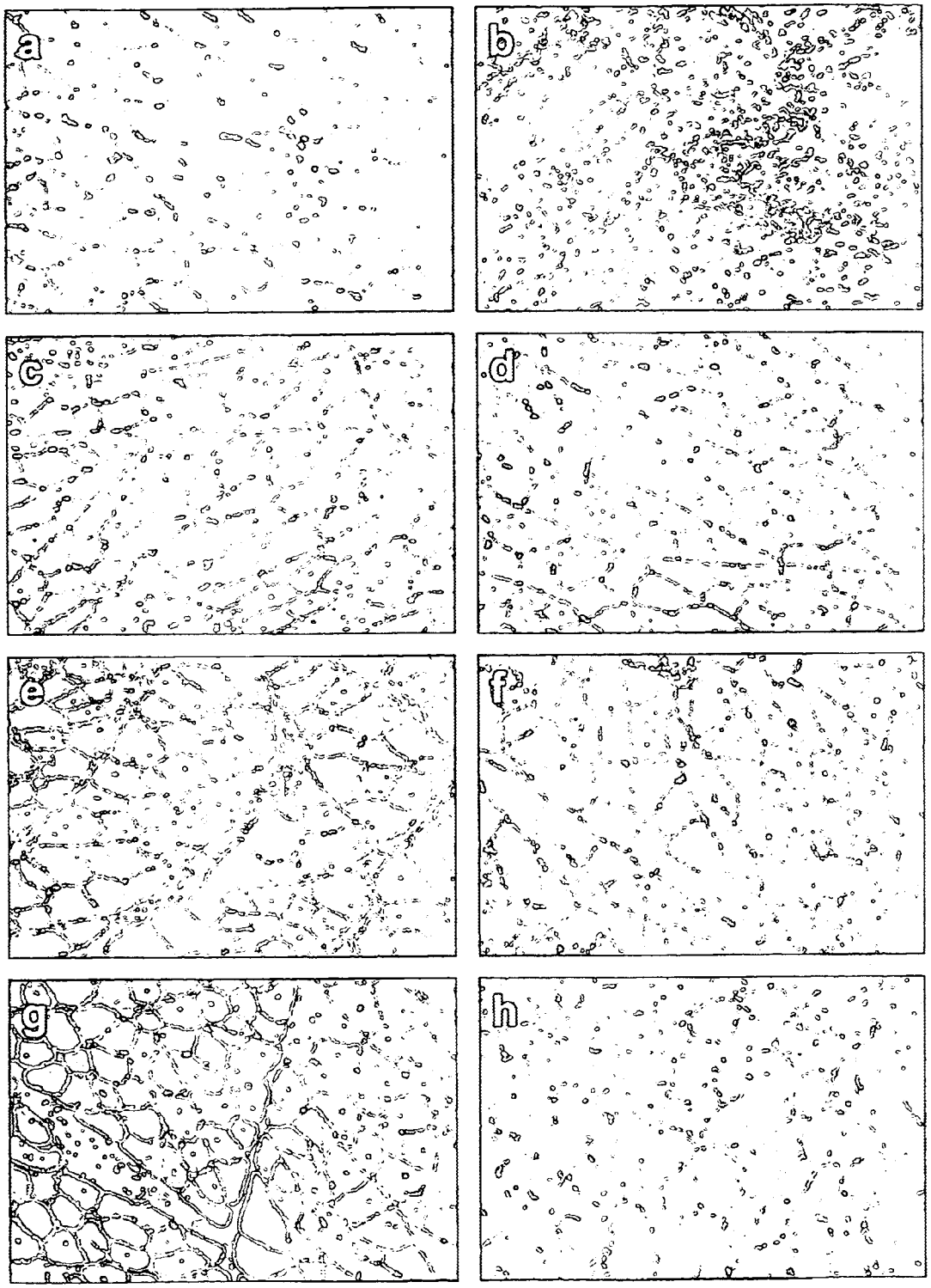
FIG. 3a shows mini-dystrophin expression in mdx mice treated with AAV-MCK-Δ3849 at 10 days of age. The animals were sacrificed 6 months post viral injection.
FIG. 3b shows dystrophin expression in untreated 6-month-old mdx mice.
FIG. 3c shows mini-dystrophin expression in mdx mice treated with AAV-MCK-Δ3849 as adult. The animals were sacrificed 2-months post viral injection.
FIG. 3d shows mini-dystrophin expression in mdx mice treated with AAV-MCK-Δ3990 as adult. The animals were sacrificed 2 months post viral injection.
FIG. 3e shows mini-dystrophin expression in mdx mice treated with AAV-MCK-Δ3849 as adult. The animals were sacrificed 4 months post viral injection.
FIG. 3f shows mini-dystrophin expression in mdx mice treated with AAV-MCK-Δ3990 as adult. The animals were sacrificed 4 months post viral injection.
FIG. 3g shows mini-dystrophin expression in mdx mice treated with AAV-CMV-Δ3849 as adult. The animals were sacrificed 6 months post viral injection.
FIG. 3h shows mini-dystrophin expression in mdx mice treated with AAV-CMV-Δ3990 as adult. The animals were sacrificed 6 months post viral injection.

At three months and six months after vector injection, the muscles were collected for evaluation of mini-dystrophin expression and biochemical restoration of the DAP complexes, which were absent due to the primary deficiency of dystrophin. IF staining on thin sections of AAV treated muscles, using an antibody (Dys3) specific to human dystrophin, revealed widespread vector transduction and correct submembrane location of the mini-dystrophins in a majority of the myofibers, especially in muscles treated with AAV vectors containing dystrophin minigene Δ3849 or Δ3990 (FIGS. 2a & 2b; FIG. 3a). As expected, the equivalent muscle from the age-matched healthy C57/B10 mice showed indistinguishable dystrophin staining pattern, when stained with an antibody (Dys2) that recognizes both mouse and human dystrophin C-terminal region (FIG. 2b). As expected, this antibody (Dys2) failed to stain the AAV treated mdx muscle due to deletion of the C-terminal region in our dystrophin minigenes (data not shown). This result further confirmed the identity of mini-dystrophins that were derived from the AAV vectors. Consistently, the untreated mdx control muscle showed no dystrophin staining (FIG. 2b) except the very few somatic revertant myofibers recognized by Dys2 antibody. Furthermore, injection of AAV mini-dystrophin vectors into the adult mdx muscle (gastrocnemius) showed similar results when examined for dystrophin expression at 2 and 4 months after injection of AAV MCK vectors (FIGS. 3c–3f), or at 6 months after injection of AAV CMV vectors (FIGS. 3g and 3h). Importantly, there was no cytotoxic T-lymphocyte (CTL) destruction against the myofibers that persistently expressed mini-dystrophins of human origin from AAV vectors, either driven by a CMV promoter or by a muscle-specific MCK promoter.

Immunofluorescent staining using three antibodies against α, β, and γ sarcoglycans respectively, showed positive results in all of the consecutive thin sections adjacent to those stained with dystrophin antibodies (FIG. 2b). These results provided evidence of biochemical functionality of the mini-dystrophins, which lack the C-terminal domain but are still capable of interacting with the DAP complexes.

EXAMPLE 3
Amelioration of Dystrophic Pathology

This example demonstrates that dystrophin minigene products can protect muscle from the pathological phenotypes. The onset of the pathology in mdx mice starts at around three weeks of age with massive waves of myofiber degeneration/regeneration. This process is characterized by the presence of central nuclei in myofibers, a primary pathological sign of muscular dystrophies. The absence or reduction of central nucleation after gene therapy would suggest that the therapy is successful. Therefore, we initially chose to test the AAV mini-dystrophin constructs in young mdx mice (10-day old) before the onset of central nucleation, to see whether muscle degeneration/regeneration can be prevented.

Figure 5A:
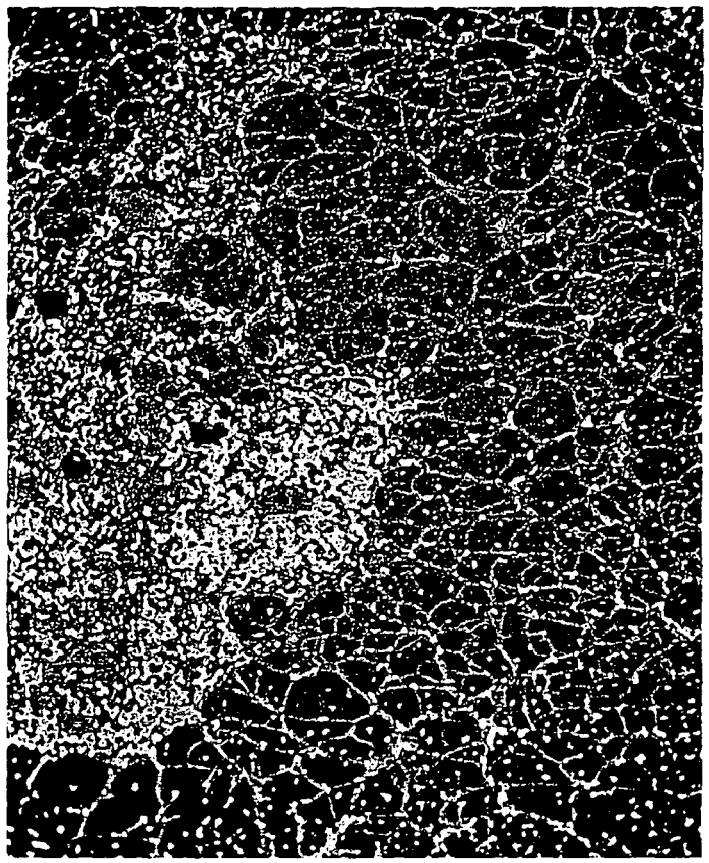
FIG. 5a shows the IF analysis of mini-dystrophin expression from construct Δ2796, which contains two rods (rod1 & rod24, see FIG. 1). Note that the muscle cell morphology and central nucleation were not improved after its injection into young mdx mice.
Figure 5B:
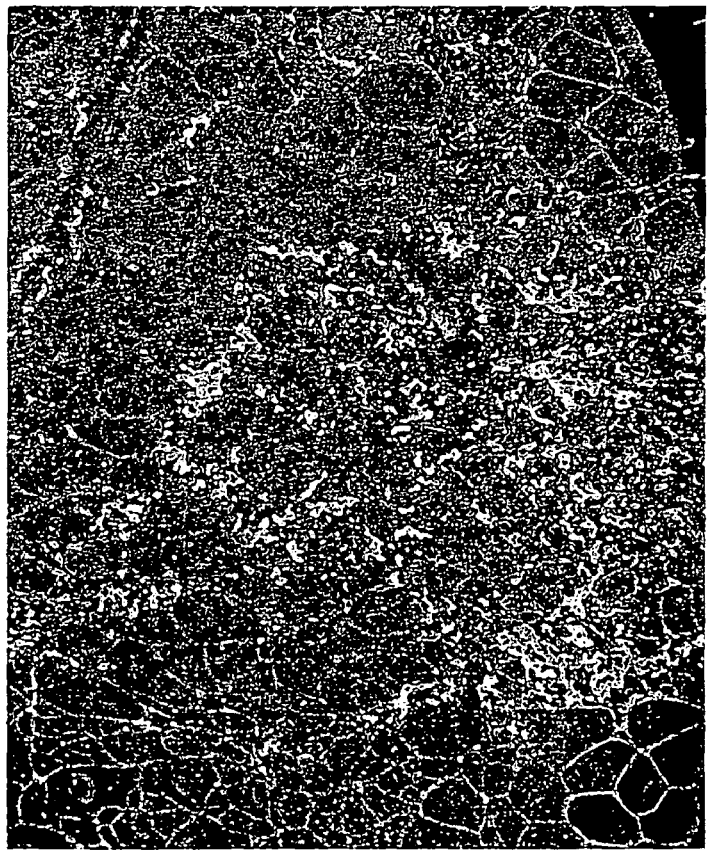
FIG. 5b shows the IF analysis of mini-dystrophin expression from construct CMV-M3, which contains 1 rod (a hybrid rod between rod R1 & rod R24, see FIG. 1 and Yuasa et al). Note that the muscle cell morphology and central nucleation were not improved after its injection into young mdx mice.

Histological examination of the mdx muscles at 3 and 6 months after AAV mini-dystrophin (containing more than 2 rod domains) treatment, which was prior to the onset of central nucleation, showed nearly exclusive (~98%) peripheral nucleation in the mini-dystrophin positive myofibers, as revealed by dystrophin immunostaining and myonuclei counterstaining with DAPI (FIG. 2a, FIG. 2b first column; FIG. 3a and Table 2). The mutual exclusivity between mini-dystrophin expression and central nucleation in the vector treated mdx muscle precisely mirrored that of the normal muscle (FIG. 2b and Table 2). In addition, the myofibers positive for mini-dystrophin expression also exhibited consistent myofiber sizes and polygonal shapes indistinguishable from those of the normal muscle (FIGS. 2a and 2b). By contrast, the untreated mdx muscle showed extensive (75.4%) central nucleation (Table 2)), with additional signs of dystrophic pathology including wide variation of myofiber sizes, round myofiber shapes, and fibrosis (FIG. 2b). Noticeably, the mdx muscle treated with constructs Δ2796 and M3 (containing 2 rods and 1 rod, respectively, see FIG. 1.) showed the same morphology as the untreated mdx muscle, except for the positive IF staining of the mini-dystrophin, which is not functional in terms of improving muscle morphology, pathology and preventing muscle degeneration/regeneration and central nucleation (FIGS. 5a & 5b and Table 2). Hence, treatment of dystrophic muscle by AAV vector with minigenes containing more than 2 rods (See FIG. 1.) prevented dystrophic pathology and led to normal histology in terms of peripheral nucleation, consistent myofiber size and lack of fibrosis in the mini-dystrophin positive areas. These results unequivocally demonstrated the absence of muscle degeneration due to the therapeutic effects of the novel mini-dystrophins in young mdx mice.

We subsequently tested AAV vectors containing dystrophin minigenes with more than 2 rods in treating adult mdx mice (45 days of age) after the onset of massive waves of degeneration/regeneration, to see whether the pathological process can be stopped or reversed. At the time of vector injection, a majority (~75%) of the myofibers already underwent degeneration/regeneration process and displayed central nucleation. At 2 months, 4 months and 6 months after AAV mini-dystrophin injection, widespread dystrophin expression was observed accompanied by normal myofiber morphology and lack of fibrosis in the dystrophin positive areas (FIGS. 3a and 3b). By contrast, muscle of untreated mdx mice (FIG. 3b), or areas of treated muscle without successful vector gene transfer, manifested progressive degeneration and fibrosis. In addition, a reduction of central nucleation in mini-dystrophin positive myofibers was observed (from approximately 75% before vector treatment to 35–50% after vector treatment; see Table 2). The partial reversal of central nucleation was also observed in healthy mouse muscle, where a majority of the myonuclei remained centrally located once experiencing a transient pathology such as myotoxin treatment (Martin et al. *Muscle Nerve* 11:588–96 [1988]). Persistence of central nucleation was also observed after treatment of adult mdx muscle with a gutless adenovirus vector containing the full-length dystrophin cDNA. Based on the above observations, our novel mini-dystrophin genes (containing more than 2 rods) demonstrated therapeutic effects in ameliorating dystrophic pathology in both young and adult mdx muscles.

EXAMPLE 4

Protection of Myofiber Membrane Integrity

Figure 4B:
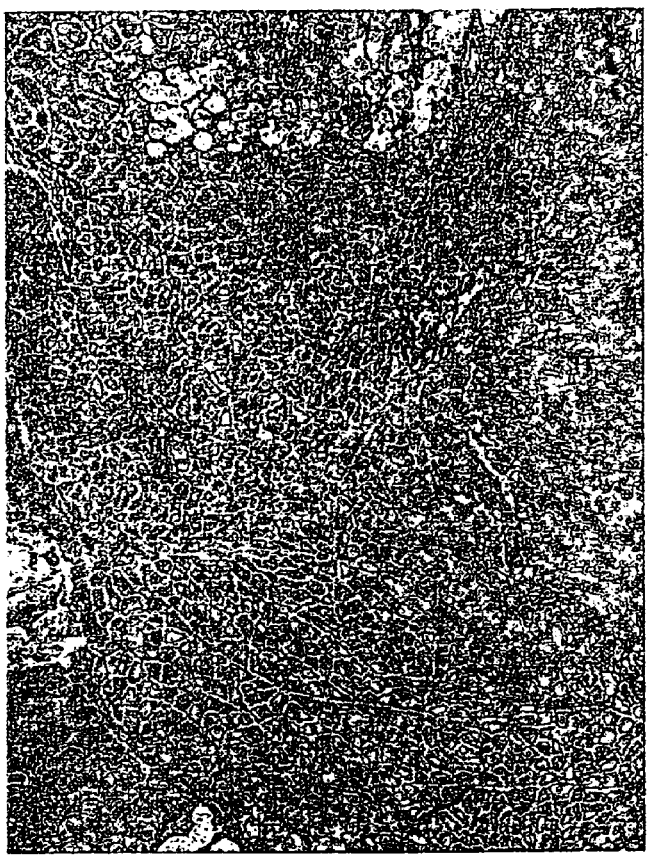
FIG. 4b shows protection of muscle plasma membrane integrity by dystrophin minigenes in mdx mice treated as adult.
Figure 4B:

This example demonstrates that mini-dystrophins containing more than 2 rods (see FIG. 1.) are capable of protect myofiber membrane integrity. Initially, Evans Blue was administered into the tail vein of mdx mice that were treated at young age (10-day old) with AAV vectors three months before. The age-matched untreated mdx mice and healthy C57/B10 mice were used as controls. To induce mechanical stress, the mice were allowed to exercise by continuous swimming for 20 minutes. Muscles were then collected and examined for dystrophin expression as well as for Evans Blue dye uptake. As expected, muscle from healthy mice revealed uniform dystrophin staining across the muscle sections and no uptake of the dye by the myofibers (FIG. 4a, top row). The AAV vector treated mdx muscle showed results consistent with the healthy muscle, thus mutual exclusivity of dystrophin expression and dye uptake (FIG. 4a, second to fourth rows). Dye uptake (red fluorescence) was found only in myofibers that lacked mini-dystrophin expression in the areas not transduced by AAV vectors (FIG. 4a, $2^{nd}$, $3^{rd}$ & $4^{th}$ rows). By contrast, the untreated mdx muscle revealed absence of dystrophin and extensive dye uptake (FIG. 4a, bottom row). More importantly, AAV mini-dystrophin treatment of adult mdx muscle also achieved similar results in protecting myofibers from plasma membrane leakage when analyzed at 2 months and 6 months after vector injection (FIG. 4b). These results unequivocally demonstrated the physiological functionality of the novel mini-dystrophins in maintaining membrane integrity and protecting myofibers from mechanical damages in both young and adult mdx mice.

TABLE 2

AAV mini-dystrophin gene transfer in young and adult mdx mice

| Animals* & vectors | n | Age at Vector injection | Months post injection | % Dystrophin positive fibers | % Central nuclei** |
|---|---|---|---|---|---|
| mdx + Δ3510 | 4 | 12 days | 3 | 35~80 | 1.06 (68/6413) |
| mdx + Δ3531 | 4 | 12 days | 3 | 25~40 | 1.72 (37/2140) |
| mdx + Δ3849 | 4 | 10 days | 3 | 56~88 | 1.02 (72/7098) |
| mdx + Δ3990 | 4 | 10 days | 3 | 50~80 | 0.99 (56/5652) |
| mdx + Δ4173 | 4 | 10 days | 3 | 15~25 | 0.93 (26/2791) |
| mdx + Δ3849 | 4 | 10 days | 6 | 40~60 | 2.80 (51/1824) |
| mdx + Δ3990 | 2 | 10 days | 6 | 35~45 | 2.30 (34/1478) |
| mdx + Δ3849 | 2 | 50 days | 2 | 35~50 | 34.76 (510/1467) |
| mdx + Δ3990 | 2 | 50 days | 2 | 35~40 | 34.18 (685/2004) |

TABLE 2-continued

AAV mini-dystrophin gene transfer in young and adult mdx mice

| Animals* & vectors | n | Age at Vector injection | Months post injection | % Dystrophin positive fibers | % Central nuclei** |
|---|---|---|---|---|---|
| mdx + Δ3849 | 4 | 50 days | 4 | 20~25 | 44.24 (615/1390) |
| mdx + Δ3990 | 4 | 50 days | 4 | 20~30 | 46.18 (695/1505) |
| C57/B10 | 4 | No injection | N/A | 100 | 1.45 (56/3860) |
| mdx | 4 | No injection | N/A | <1 | 75.4 (2382/3160) |
| mdx + Δ2796 | 4 | 12 days | 3 | 30~45 | 72 (3888/5400) |
| mdx + M3 | 8 | 10–12 days | 3 | 20~65 | 81 (5589/6900) |

Note:
*Untreated control mdx and C57/B10 mice were about 3 months old at the endpoints of experiments. AAV vectors were driven by a MCK promoter.
**All numbers were collected from dystrophin-positive myofibers which were photographed following immunofluorescent staining and DAPI counterstaining, except in untreated mdx mice which had extensive central nucleation and very few dystrophin-positive

EXAMPLE 5

Restoration of Muscle Strength

Figure 6:
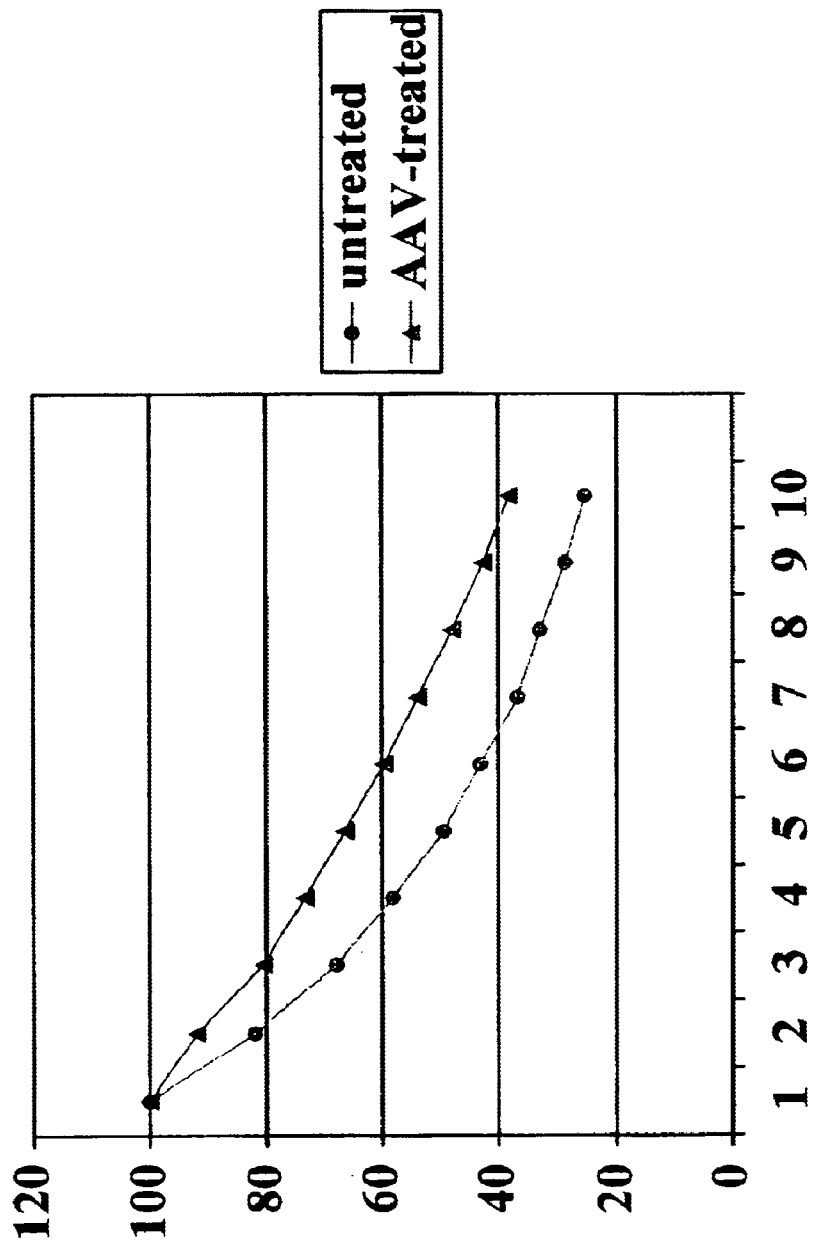
FIG. 6 shows muscle force improvement after AAV-MCK-Δ3990 vector injection into the TA muscle of adult mdx mice. After 10 cycles of lengthening activation the untreated mdx TA muscles (n=8) had only 23% of the force output remaining, while the AAV treated mdx TA muscles (n=8) had nearly 40% of the force output remaining.

This example demonstrates that mini-dystrophins restore muscle strength in mdx mice. Muscle constrctile force improvement was evaluated in the mdx mice after treatment with AAV vectors containing the dystrophin minigene. Tibialis anterior (TA) muscles of 2 to 3 month old mdx mice were injected with AAV-MCK-3990 vector. The injection was given in such a way that one leg was treated while the other leg in the same animal was left untreated. The latter was used as a control. At 6 months after AAV treatment, the mdx mice were anesthetized and the entire TA muscle was removed and mounted in a vertical tissue chamber for in vitro force measurement. The muscle was stimulated by the use of monophasic rectangular pulses of cathodal current (1.0-ms duration). Maximum tetanic force ($P_o$) was assessed using a stimulation frequency of 75 pps delivered in a 500 ms duration train. Following the determination of $P_o$, the ability of the TA muscle to sustain force generation during repetitive lengthening activations (which should induce maximal damage to the muscle) was assessed. Peak force measured prior to lengthening was termed $P_{ISO}$. Subsequently, the muscle was lengthened at a constant velocity of 1.0 $L_o$/s from 100 to 110% $L_o$. Stimulus trains were repeated every 2-min (duty cycle 0.004) for a total of 10 cycles. Changes in $P_{ISO}$ were used to index impairment of muscle function associated with the damages caused by lengthening activations. As shown in FIG. 6, after 10 cycles of lengthening activations the untreated TA muscles (n=8) had only 23% of the force output remaining, while the AAV treated TA muscles (n=8) had nearly 40% of the force output remaining. This result strongly indicates that the dystrophin minigene can protect the muscle from mechanical force induced damage, therefore, restore the muscle strength.

In summary, these examples demonstrate that dystrophin gene can be successfully reduced to one third (⅓) of its 11 kb full-length coding sequence, without compromising essential functions in protecting muscles from dystrophic phenotypes. Moreover, we have demonstrated for the first time that intramuscular injection of AAV vectors carrying the novel human dystrophin minigenes can achieve efficient and long-term therapeutic effects in a mammalian animal model. Long-term correction of both biochemical and physiological defects in the dystrophic muscles was realized by the persistent mini-dystrophin expression from AAV vectors, and the apparent lack of CTL immune response against myofibers expressing human dystrophin.

EXAMPLE 6

Construction and Testing of Retroviral Vectors

Retrovirus based gene transfer vectors are widely used to introduce transgenes permanently into the in vitro cultured cells. Those target cells may be stable cell lines or primary cell cultures derived from freshly isolated tissues or bone marrow. Some of the primary cell cultures may contain progenitor cells or stem cells, for example, hematopoietic stem cells and muscle derived stem cells. Those stem cells possess the capability of differentiating into mature muscle cells, i.e. myotubes and myofibers. Therefore, ex vivo gene transfer of the dystrophin minigenes via the retroviral vector may be a useful method to treat muscular dystrophin by infecting the stem cells isolated from the patients, who lack the dystrophin protein due to mutations in the dystrophin gene. To examine the usefulness of retroviral vectors, we cloned dystrophin minigene Δ3990 or Δ3849 (PCR product) into the Stu I site of a retroviral vector plasmid pLNCX (Clontech, California, USA). Two retroviral vector plasmids were obtained respectively carrying dystrophin minigene Δ3990 or Δ3849 under the control of a CMV promoter. The retroviral vector particles were produced by transfecting the vector plasmid pLNCXΔ3990 or pLNCXΔ3849 into the packaging cell line AmphoPack 293 (Clontech, California, USA). The above retrovirus particles were used to infect the myoblast cells isolated from the muscle tissue of mdx mice. Selection drug G418 was used to kill the cells not infected by the retroviral vector, which carried a $Neo^r$ gene to confer the G418 resistance. The G418 resistant myoblast cells containing the A3990 or A3849 minigene were induced to differentiation into myotubes by culturing with 2% horse serum in DMED media. The differentiated myotubes were subjected to immunofluorescent staining using monoclonal antibody (Dys-3) against the minigene protein product. A majoristy of the myotubes were stained positive for the dystrophin minigene expression, demonstrating the minigene can be successfully introduced into muscle progenitor cells by retroviral vectors. Such retroviral vector infected progenitor cells or stem cells may be used for the purpose of ex vivo gene therapy for Duchenne and Becker muscular dystrophies.

What is claimed is:

1. An isolated nucleotide sequence comprising a dystrophin minigene encoding a protein or the complement of the dystrophin minigene, wherein the protein comprises:
   (a) a N-terminal domain of a dystrophin protein or a modified N-terminal domain of the dystrophin protein;
   (b) five rod repeats of the dystrophin protein;
   (c) an H1 domain of a dystrophin gene and an H4 domain of the dystrophin protein; and
   (d) a cysteine-rich domain of the dystrophin protein, wherein said nucleotide sequence has fewer than 5,000 nucleotides.

2. An isolated nucleotide sequence comprising a dystrophin mingene encoding a protein or the complement of the dystrophin minigene, wherein the protein comprises:
   (a) a N-terminal domain of a dystrophin protein or a modified N-terminal domain of the dystrophin protein;
   (b) six rod repeats of the dystrophin protein;
   (c) an H1 domain of a dystrophin protein and an H4 domain of the dystrophin protein; and
   (d) a cysteine-rich domain of the dystrophin protein, wherein said nucleotide sequence has fewer than 5,000 nuclotides.

3. An isolated nucleotide sequence consisting of SEQ ID NO:2, or which is the complement of SEQ ID NO:2.

4. An isolated nucleotide sequence consisting of SEQ ID NO:6, or which is the complement of SEQ ID NO:6.

5. An isolated nucleotide sequence consisting of SEQ ID NO:9, or which is the complement of SEQ ID NO:9.

6. An isolated nucleotide sequence consisting of SEQ ID NO:10, or which is the complement of SEQ ID NO:10.

7. An isolated nucleotide sequence consisting of SEQ ID NO:12, or which is the complement of SEQ ID NO:12.

8. An isolated nucleotide sequence consisting of SEQ ID NO:14, or which is the complement of SEQ ID NO:14.

9. A recombinant adeno-associated virus vector, comprising any one of the nucleotide sequences of claims 3, 4, 5, 6, 7 and 8, operably linked to an expression control element.

10. The recombinant adeno-associated virus vector of claim 9, wherein the control element is an MCK promoter or a CMV promoter.

11. A recombinant adeno-associated virus vector, comprising the nucleotide sequence of claim 4, operably linked to an expression control element.

12. A recombinant adeno-associated virus vector, comprising the nucleotide sequence of claim 5, operably linked to an expression control element.

13. A recombinant adeno-associated virus vector, comprising the nucleotide sequence of claim 6, operably linked to an expression control element.

14. A recombinant adeno-associated virus vector, comprising the nucleotide sequence of claim 7, operably linked to an expression control element.

15. A recombinant adeno-associated virus vector, comprising the nucleotide sequence of claim 8, operably linked to an expression control element.

* * * * *

UNITED STATES PATENT AND TRADEMARK OFFICE
CERTIFICATE OF CORRECTION

| | |
|---|---|
| PATENT NO. | : 7,001,761 B2 |
| APPLICATION NO. | : 09/845416 |
| DATED | : February 21, 2006 |
| INVENTOR(S) | : Xiao Xiao |

It is certified that error appears in the above-identified patent and that said Letters Patent is hereby corrected as shown below:

Column 18, line 61, "majoristy" should be -- majority --.

Signed and Sealed this

Twenty-first Day of November, 2006

JON W. DUDAS
*Director of the United States Patent and Trademark Office*